United States Patent
Ogawa et al.

(10) Patent No.: US 9,671,860 B2
(45) Date of Patent: Jun. 6, 2017

(54) MANIPULATION INPUT DEVICE AND MANIPULATOR SYSTEM HAVING THE SAME

(71) Applicant: OLYMPUS CORPORATION, Tokyo (JP)

(72) Inventors: Ryohei Ogawa, Tokyo (JP); Masaru Yanagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 637 days.

(21) Appl. No.: 14/169,825

(22) Filed: Jan. 31, 2014

(65) Prior Publication Data

US 2014/0160015 A1 Jun. 12, 2014

Related U.S. Application Data

(63) Continuation of application No. PCT/JP2012/070418, filed on Aug. 3, 2012.
(Continued)

(30) Foreign Application Priority Data

May 18, 2012 (JP) ................................. 2012-114610

(51) Int. Cl.
| | | |
|---|---|---|
| G06F 3/01 | (2006.01) | |
| B25J 13/02 | (2006.01) | |
| A61B 17/29 | (2006.01) | |
| A61B 17/32 | (2006.01) | |
| A61B 18/14 | (2006.01) | |
| B25J 9/16 | (2006.01) | |
| A61B 34/30 | (2016.01) | |

(Continued)

(52) U.S. Cl.
CPC .............. G06F 3/01 (2013.01); A61B 17/29 (2013.01); A61B 17/32002 (2013.01);
(Continued)

(58) Field of Classification Search
None
See application file for complete search history.

(56) References Cited

U.S. PATENT DOCUMENTS

| | | |
|---|---|---|
| 3,139,990 A | 7/1964 | Jelatis et al. |
| 3,923,166 A | 12/1975 | Fletcher et al. |
| | (Continued) | |

FOREIGN PATENT DOCUMENTS

| | | |
|---|---|---|
| CN | 101027010 A | 8/2007 |
| CN | 101167658 A | 4/2008 |
| | (Continued) | |

OTHER PUBLICATIONS

Chinese Office Action dated Jun. 3, 2015 from related Chinese Application No. 201280035926.3, together with an English language translation.
(Continued)

Primary Examiner — Nicholas Lee
(74) Attorney, Agent, or Firm — Scully, Scott, Murphy & Presser, P.C.

(57) ABSTRACT

A manipulation input device includes a master grip having a grip part and manipulation handles movably supported on the grip part, a spring configured to generate manipulation resistance in response to a displacement amount of the manipulation handles when the manipulation handles are manipulated, and a force magnitude adjusting unit configured to adjust the force magnitude of the manipulation resistance relative to the displacement amount.

23 Claims, 31 Drawing Sheets

Related U.S. Application Data

(60) Provisional application No. 61/515,203, filed on Aug. 4, 2011.

(51) Int. Cl.
| | |
|---|---|
| *A61B 46/10* | (2016.01) |
| *A61B 34/37* | (2016.01) |
| *A61B 34/00* | (2016.01) |
| A61B 17/00 | (2006.01) |
| A61B 17/068 | (2006.01) |
| *A61B 46/23* | (2016.01) |
| *A61B 90/90* | (2016.01) |
| *A61B 90/00* | (2016.01) |

(52) U.S. Cl.
CPC .......... *A61B 18/1402* (2013.01); *A61B 34/30* (2016.02); *A61B 34/37* (2016.02); *A61B 34/74* (2016.02); *A61B 34/76* (2016.02); *A61B 34/77* (2016.02); *A61B 46/10* (2016.02); *B25J 9/1689* (2013.01); *B25J 13/02* (2013.01); A61B 17/068 (2013.01); A61B 46/23 (2016.02); A61B 90/90 (2016.02); A61B 2017/00119 (2013.01); A61B 2017/00477 (2013.01); A61B 2017/00482 (2013.01); A61B 2090/0803 (2016.02); A61B 2090/0814 (2016.02); Y10S 901/08 (2013.01); Y10S 901/09 (2013.01); Y10S 901/30 (2013.01); Y10T 29/49826 (2015.01); Y10T 74/18056 (2015.01)

(56) References Cited

U.S. PATENT DOCUMENTS

| | | | |
|---|---|---|---|
| 4,672,281 A | 6/1987 | Yagusic et al. |
| 4,830,569 A | 5/1989 | Jannborg |
| 4,872,803 A | 10/1989 | Asakawa |
| 5,214,969 A | 6/1993 | Adkins et al. |
| 5,603,723 A | 2/1997 | Aranyi et al. |
| 5,632,432 A | 5/1997 | Schulze et al. |
| 5,649,956 A | 7/1997 | Jensen et al. |
| 5,656,903 A | 8/1997 | Shui et al. |
| 5,712,543 A | 1/1998 | Sjostrom |
| 5,760,530 A | 6/1998 | Kolesar |
| 5,762,458 A | 6/1998 | Wang et al. |
| 5,784,542 A | 7/1998 | Ohm et al. |
| 5,817,119 A | 10/1998 | Klieman et al. |
| 5,836,869 A | 11/1998 | Kudo et al. |
| 5,855,583 A | 1/1999 | Wang et al. |
| 5,871,493 A | 2/1999 | Sjostrom et al. |
| 5,876,325 A | 3/1999 | Mizuno et al. |
| 6,007,550 A | 12/1999 | Wang et al. |
| 6,039,748 A | 3/2000 | Savage et al. |
| 6,063,095 A | 5/2000 | Wang et al. |
| 6,082,797 A | 7/2000 | Antonette |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 | 3/2001 | Ramans |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Wang et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 | 6/2014 | Sakai et al. |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 | 3/2016 | Hager et al. |
| 9,308,009 B2 | 4/2016 | Madan et al. |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033024 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |

(56) References Cited

U.S. PATENT DOCUMENTS

| | | |
|---|---|---|
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | H10-502265 A | 3/1998 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |
| JP | 2005-312991 A | 11/2005 |
| JP | 2006-061272 A | 3/2006 |

(56) References Cited

FOREIGN PATENT DOCUMENTS

| | | | |
|---|---|---|---|
| JP | 2006-167867 A | 6/2006 | |
| JP | 2006-288955 A | 10/2006 | |
| JP | 2006-321027 A | 11/2006 | |
| JP | 2007-029274 A | 2/2007 | |
| JP | 2007-038315 A | 2/2007 | |
| JP | 2007-98507 A | 4/2007 | |
| JP | 2007-105485 A | 4/2007 | |
| JP | 3999816 B2 | 10/2007 | |
| JP | 2008-000282 A | 1/2008 | |
| JP | 2008-036793 A | 2/2008 | |
| JP | 4058113 B2 | 3/2008 | |
| JP | 2008-093270 A | 4/2008 | |
| JP | 2008-104854 A | 5/2008 | |
| JP | 2008-514357 A | 5/2008 | |
| JP | 2008-173724 A | 7/2008 | |
| JP | 2008-188109 A | 8/2008 | |
| JP | 4129313 B2 | 8/2008 | |
| JP | 4176126 B2 | 11/2008 | |
| JP | 2009-028157 A | 2/2009 | |
| JP | 2009-056164 A | 3/2009 | |
| JP | 2009-512514 A | 3/2009 | |
| JP | 2009-520573 A | 5/2009 | |
| JP | 2009-178230 A | 8/2009 | |
| JP | 2009-178541 A | 8/2009 | |
| JP | 2009-530037 A | 8/2009 | |
| JP | 2009-195694 A | 9/2009 | |
| JP | 2009-226029 A | 10/2009 | |
| JP | 2009-226093 A | 10/2009 | |
| JP | 2009-269127 A | 11/2009 | |
| JP | 2010-504127 A | 2/2010 | |
| JP | 2010-076012 A | 4/2010 | |
| JP | 2010-524548 A | 7/2010 | |
| JP | 2011-509112 A | 3/2011 | |
| JP | 2011-206213 A | 10/2011 | |
| JP | 2012-000199 A | 1/2012 | |
| JP | 2012-091310 A | 5/2012 | |
| WO | 96/00044 A1 | 1/1996 | |
| WO | 97/16123 A1 | 5/1997 | |
| WO | 97/16124 A1 | 5/1997 | |
| WO | 97/29690 A1 | 8/1997 | |
| WO | 98/25666 A1 | 6/1998 | |
| WO | 00/51486 A1 | 9/2000 | |
| WO | 00/60421 A2 | 10/2000 | |
| WO | 03/049596 A2 | 6/2003 | |
| WO | 2006/039092 A2 | 4/2006 | |
| WO | 2006/111966 A2 | 10/2006 | |
| WO | 2007/047782 A2 | 4/2007 | |
| WO | 2007/075864 A1 | 7/2007 | |
| WO | 2007/111955 A2 | 10/2007 | |
| WO | 2007/126443 A2 | 11/2007 | |
| WO | 2007/138674 A1 | 12/2007 | |
| WO | 2008/038184 A2 | 4/2008 | |
| WO | 2008/108289 A1 | 9/2008 | |
| WO | 2009/034477 A2 | 3/2009 | |
| WO | 2009/089614 A1 | 7/2009 | |
| WO | 2010/006057 A1 | 1/2010 | |
| WO | 2010/093152 A2 | 8/2010 | |
| WO | 2010/109932 A1 | 9/2010 | |
| WO | 2010/126127 A1 | 11/2010 | |
| WO | 2011/025786 A1 | 3/2011 | |
| WO | 2011/060139 A2 | 5/2011 | |
| WO | 2011/060185 A1 | 5/2011 | |
| WO | 2011/060187 A1 | 5/2011 | |
| WO | 2011/085815 A1 | 7/2011 | |
| WO | 2012/042949 A1 | 4/2012 | |

OTHER PUBLICATIONS

Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Japanese Office Action dated Jan. 19, 2016 from related Japanese Patent Application No. 2012-036226, together with an English language translation.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.
European Patent Office Communication dated May 23, 2016 in related European Application No. 12 819 877.7.
Japanese Office Action dated Jun. 14, 2016 in related Japanese Patent Application No. 2012-012104.
Office Action dated Jun. 16, 2016 received in related U.S. Appl. No. 14/169,742.
Office Action dated Oct. 19, 2015 received in related U.S. Patent Application, namely U.S. Appl. No. 14/168,525.
Office Action dated Oct. 22, 2015 received in related U.S. Patent Application, namely U.S. Appl. No. 14/151,987.
Office Action dated Sep. 15, 2015 received in related U.S. Patent Application, namely U.S. Appl. No. 13/566,012.
office Action dated Nov. 19, 2015 received in related U.S. Patent Application, namely U.S. Appl. No. 14/157,920.
Office Action dated Feb. 22, 2016 received in related U.S. Appl. No. 14/168,496.
Office Action dated Mar. 10, 2016 received in related U.S. Appl. No. 13/566,012.
Office Action dated Mar. 24, 2016 received in related U.S. Appl. No. 13/566,047.
Office Action dated May 9, 2016 received in related U.S. Appl. No. 14/170,856.
Japanese Office Action dated Jun. 28, 2016 in related Japanese Patent Application No. 2013-526973.
U.S. Office Action dated Apr. 9, 2015 received in related U.S. Patent Application, namely U.S. Appl. No. 14/169,675.
U.S. Office Action dated May 8, 2015 received in related U.S. Patent Application, namely U.S. Appl. No. 14/157,920.
English Abstract of JP 01-234140 dated Sep. 19, 1989.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
Notice of Allowance dated Jan. 20, 2015 from related U.S. Appl. No. 13/566,023.
Notice of Allowance dated Jan. 29, 2015 from related U.S. Appl. No. 14/168,551.

(56) References Cited

OTHER PUBLICATIONS

Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Patent Application, namely U.S. Appl. No. 14/169,321.
Extended Supplementary European Search Report dated Mar. 27, 2015 from related European Application No. 12 82 0056.5.
Japanese Office Action dated Jan. 4, 2017 received in Japanese Patent Application No. 2012-012104.
Office Action dated Feb. 28, 2017 received in U.S. Appl. No. 14/168,496.

FIG. 3A
FIG. 3B
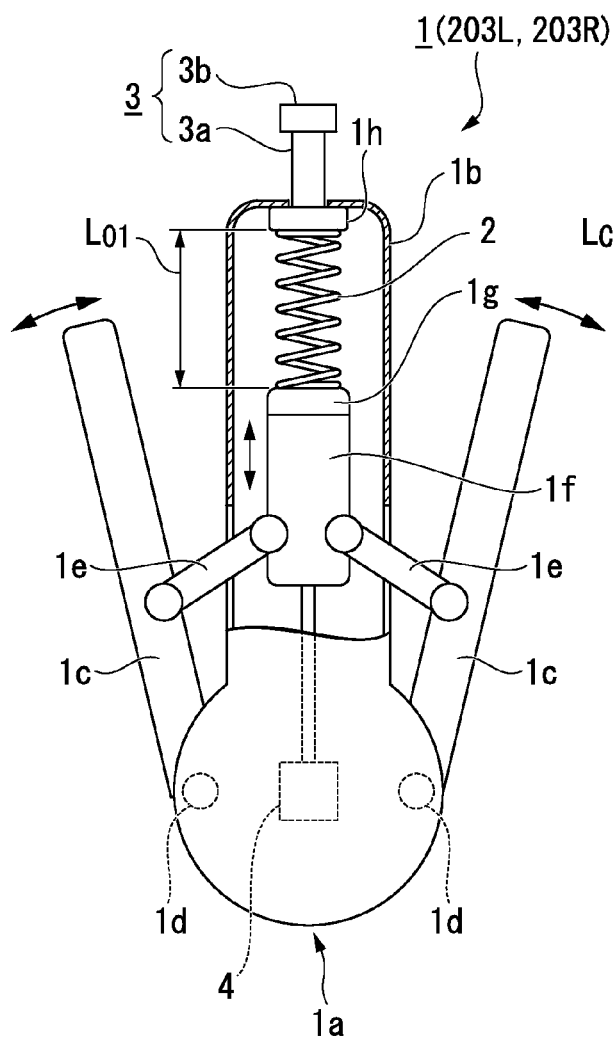
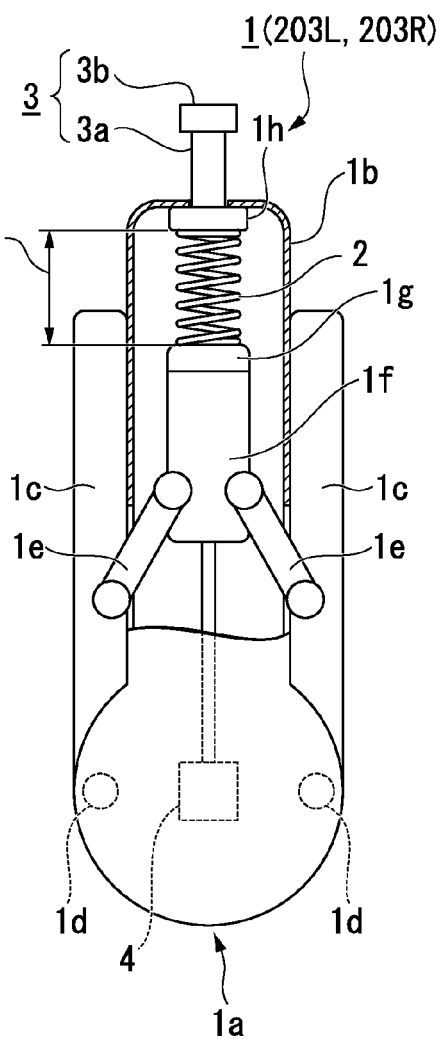

FIG. 4A
FIG. 4B
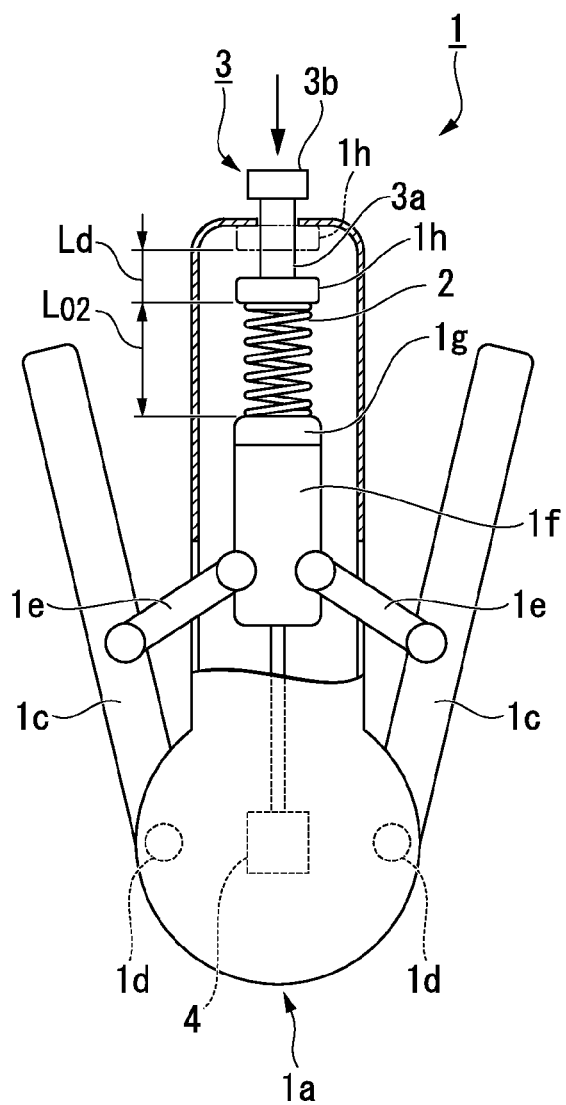
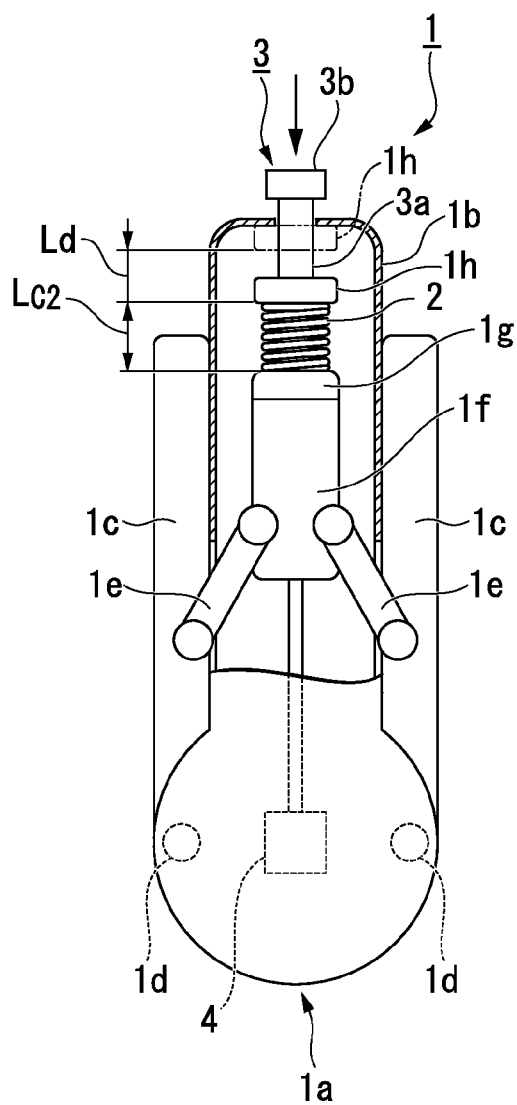

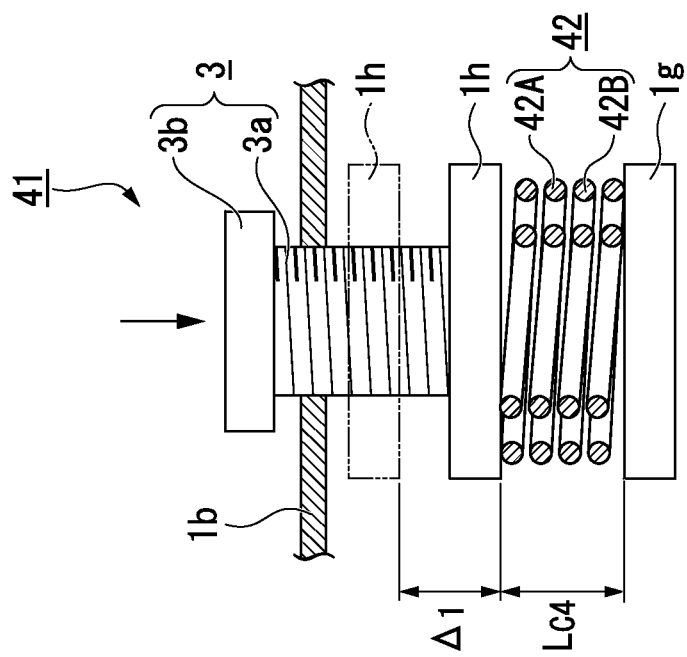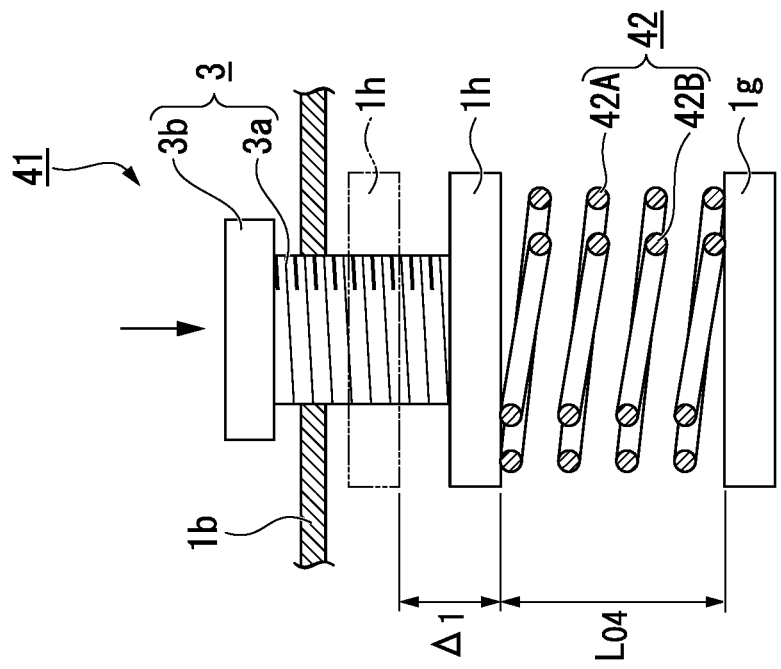

FIG. 36A
FIG. 36B
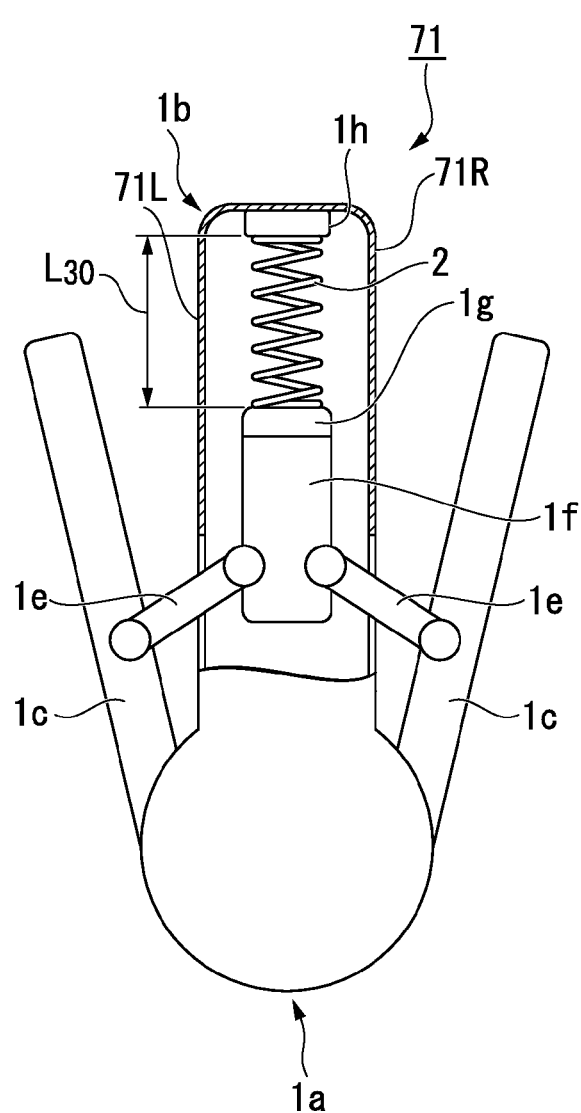
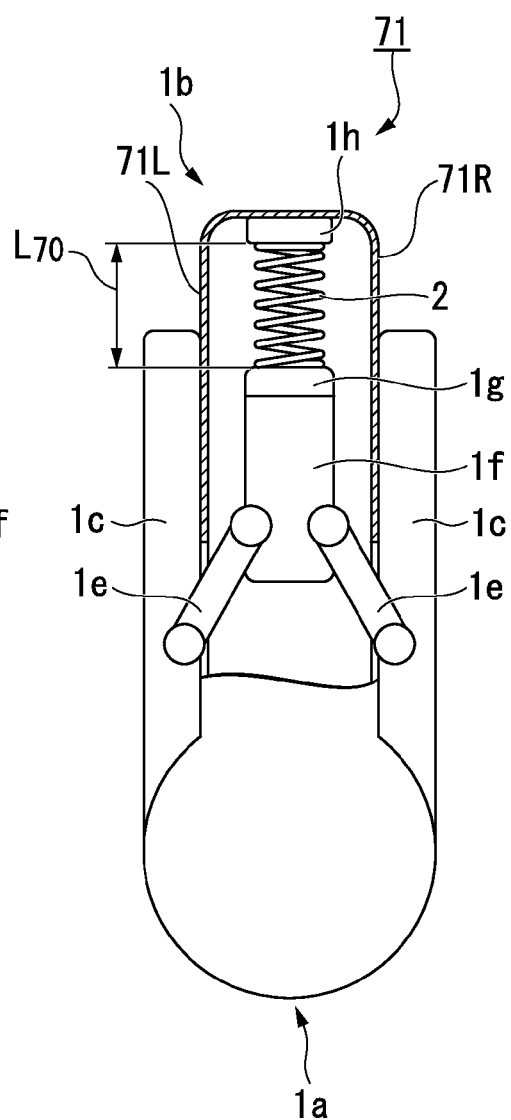

MANIPULATION INPUT DEVICE AND MANIPULATOR SYSTEM HAVING THE SAME

This application is a continuation application based on a PCT Patent Application No. PCT/JP2012/070418, filed on Aug. 3, 2012, whose priority is claimed on U.S. Provisional Application Ser. No. 61/515,203, filed on Aug. 4, 2011 and Japanese Patent Application No. 2012-114610, filed on May 18, 2012. The contents of all of the PCT application, the U.S. Provisional application and the Japanese Application are incorporated herein by reference.

BACKGROUND OF THE INVENTION

Technical Field

The present invention relates to a manipulation input device and a manipulator system having the same, and more particularly, to a manipulation input device that is capable of being used in a master-slave type medical manipulator system, and a manipulator system having the same.

Description of Related Art

Generally, as a medical manipulator for assisting an operation in surgery, a master-slave type manipulator system is known. This medical manipulator is equipped with a master grip that performs manipulation input on an operation of an instrument, such as a forceps or a needle holder, which is mounted on a slave manipulator and is used for surgery. A surgeon who is an operator manipulates the master grip, thereby transferring an operation of the master grip to this instrument.

The master grip configured so that, when an operator opens/closes a manipulation handle so as to be able to have a sense of actually grasping a target with a forceps or a needle holder, manipulation resistance is transferred from the master grip to the operator, is known.

For example, in a removable master grip handle described in U.S. Pat. No. 6,587,750, a bias spring compressed by gradually closing the handle is connected at a distal end side (which is a front side of an operator and is a side moving away from the operator) of a movable rod coupled to the handle via a link. Thereby, manipulation resistance is configured to be generated.

Further, in a manipulator system described in Japanese Unexamined Patent Application, First Publication No. 2010-76012, manipulation input is performed by an operator pulling a trigger protruding on a side of a manipulation pole with his or her finger. In that case, a spring mounted in the trigger is compressed, and manipulation resistance is configured to be generated.

SUMMARY OF THE INVENTION

According to a first aspect of the present invention, a manipulation input device includes: a manipulation unit having a manipulation unit main body and manipulation handles movably supported on the manipulation unit main body; a manipulation resistance generator configured to generate manipulation resistance in response to a displacement amount of the manipulation handles when the manipulation handles are manipulated; and a force magnitude adjusting unit configured to adjust the force magnitude of the manipulation resistance relative to the displacement amount.

According to a second aspect of the present invention, in the manipulation input device according to the first aspect, the manipulation handles may be rotatably supported on the manipulation unit main body and be installed to permit opening/closing manipulation.

According to a third aspect of the present invention, in the manipulation input device according to the first aspect or the second aspect, the force magnitude adjusting unit may fix a change rate characteristic of the force magnitude of the manipulation resistance relative to the displacement amount, and change a reference force magnitude value of the force magnitude of the manipulation resistance relative to a reference value of the displacement amount.

According to a fourth aspect of the present invention, in the manipulation input device according to any one of the first aspect to the third aspect, the manipulation resistance generator may include an elastic member deformed by displacement manipulation of the manipulation handles and configured to generate the manipulation resistance, and the force magnitude adjusting unit may deform the elastic member, and adjust a deformation amount of the elastic member to change the reference force magnitude value.

According to a fifth aspect of the present invention, in the manipulation input device according to the fourth aspect, the force magnitude adjusting unit may include an actuator configured to change the reference force magnitude value.

According to a sixth aspect of the present invention, in the manipulation input device including the actuator according to the fifth aspect, a manipulation input control unit configured to control an operation of the actuator may be further provided.

According to a seventh aspect of the present invention, in the manipulation input device including the manipulation input control unit according to the sixth aspect, the manipulation input control unit may acquire identification information about a manipulated device from the manipulated device and control the operation of the actuator based on the identification information.

According to an eighth aspect of the present invention, in the manipulation input device including the manipulation input control unit according to the sixth aspect or the seventh aspect, the manipulation unit may include an identification information part that is detachably installed on a manipulation input device main body and transfers identification information about the manipulation unit to the manipulation input control unit when mounted.

According to a ninth aspect of the present invention, in the manipulation input device including the manipulation input control unit according to any one of the sixth aspect to the eighth aspect, the manipulation input control unit may include a procedure mode input unit through which the operator selects a procedure mode to be performed by the manipulated device, and control the operation of the actuator based on the procedure mode input by the procedure mode input unit.

According to a tenth aspect of the present invention, in the manipulation input device including the manipulation input control unit according to any one of the sixth aspect to the ninth aspect, the manipulation input control unit may include a time-dependent change detection unit configured to detect a time-dependent change of the manipulation resistance, and control the operation of the actuator to correct the time-dependent change of the manipulation resistance when the time-dependent change of the manipulation resistance is detected by the time-dependent change detection unit.

According to an eleventh aspect of the present invention, in the manipulation input device including the time-dependent change detection unit according to the tenth aspect, the time-dependent change detection unit may determine the time-dependent change of the manipulation resistance based on a number of times of manipulation of the manipulation resistance generator.

According to a twelfth aspect of the present invention, in the manipulation input device including the time-dependent change detection unit according to the tenth aspect, the time-dependent change detection unit may determine the time-dependent change of the manipulation resistance based on a manipulation time of the manipulation resistance generator.

According to a thirteenth aspect of the present invention, in the manipulation input device including the time-dependent change detection unit according to the tenth aspect, a force detection unit configured to detect a reaction force of the manipulation resistance generator may be provided, and the time-dependent change detection unit may determine the time-dependent change of the manipulation resistance based on a force magnitude of the reaction force of the manipulation resistance generator.

According to a fourteenth aspect of the present invention, in the manipulation input device according to the third aspect or the fourth aspect, the force magnitude adjusting unit may include a manual adjustment mechanism configured to manually adjust the reference force magnitude value.

According to a fifteenth aspect of the present invention, in the manipulation input device including the manual adjustment mechanism according to the fourteenth aspect, an adjustment target setting means configured to set an adjustment target value of the reference force magnitude value, and an adjustment detection unit configured to detect a difference of the reference force magnitude value from the adjustment target value when the manual adjustment mechanism operates, and inform of whether or not the reference force magnitude value is identical to the adjustment target value may be provided.

According to a sixteenth aspect of the present invention, in the manipulation input device including the manual adjustment mechanism according to the fourteenth aspect, an adjustment detection unit configured to detect a difference of the reference force magnitude value from a preset adjustment target value when the manual adjustment mechanism operates, and inform of whether or not the reference force magnitude value is identical to the adjustment target value may be provided.

According to a seventeenth aspect of the present invention, in the manipulation input device including the manual adjustment mechanism according to any one of the fourteenth aspect to the sixteenth aspect, a time-dependent change detection unit configured to detect a time-dependent change of the manipulation resistance, and a time-dependent change warning unit configured to give a warning when the time-dependent change of the manipulation resistance is detected by the time-dependent change detection unit may be provided.

According to an eighteenth aspect of the present invention, in the manipulation input device according to the seventeenth aspect, the time-dependent change detection unit determines the time-dependent change of the manipulation resistance based on a number of times of manipulation of the manipulation resistance generator.

According to a nineteenth aspect of the present invention, in the manipulation input device according to the seventeenth aspect, the time-dependent change detection unit determines the time-dependent change of the manipulation resistance based on a manipulation time of the manipulation resistance generator.

According to a twentieth aspect of the present invention, in the manipulation input device according to the seventeenth aspect, a force detection unit is configured to detect a reaction force of the manipulation resistance generator, wherein the time-dependent change detection unit determines the time-dependent change of the manipulation resistance based on a force magnitude of the reaction force of the manipulation resistance generator.

According to a twenty-first aspect of the present invention, in the manipulation input device according to the first aspect or the second aspect, the manipulation resistance generator may include a resistance generating actuator configured to generate a reaction force by displacement manipulation of the manipulation handles to generate the manipulation resistance, and the force magnitude adjusting unit may adjust a resistance force magnitude of the resistance generating actuator corresponding to a reference value of the displacement amount.

According to an twenty-second aspect of the present invention, in the manipulation input device according to the first aspect or the second aspect, the force magnitude adjusting unit may change a change rate characteristic of the force magnitude of the manipulation resistance relative to the displacement amount, and thereby change a reference force magnitude value of the force magnitude of the manipulation resistance relative to a reference value of the displacement amount.

According to a twenty-third aspect of the present invention, in the manipulation input device changing the change rate characteristic of the force magnitude of the manipulation resistance according to the twenty-second aspect, the manipulation resistance generator may include an elastic member, a spring constant of which is changed depending on the displacement amount.

According to a twenty-fourth aspect of the present invention, in the manipulation input device changing the change rate characteristic of the force magnitude of the manipulation resistance according to the twenty-second aspect, the manipulation resistance generator may include a resistance generating actuator that generates a reaction force by displacement manipulation of the manipulation handles to generate the manipulation resistance and that makes the reaction force adjustable.

According to a twenty-fifth aspect of the present invention, a manipulator system includes the manipulation input device according to any one of the first aspect to the twenty-fourth aspect.

BRIEF DESCRIPTION OF THE DRAWINGS

FIG. 3A is a schematic partial cross-sectional view showing configurations of an opened state of the manipulation input device according to the first embodiment of the present invention.

FIG. 3B is a schematic partial cross-sectional view showing configurations of a closed state of the manipulation input device according to the first embodiment of the present invention.

FIG. 4A is a schematic partial cross-sectional view showing an opened state when performing force magnitude adjustment of the manipulation input device according to the first embodiment of the present invention.

FIG. 4B is a schematic partial cross-sectional view showing a closed state when performing force magnitude adjustment of the manipulation input device according to the first embodiment of the present invention.

FIG. 31A is a schematic cross-sectional view showing an operation of the manipulation input device according to the second embodiment of the present invention when a force magnitude is adjusted.

FIG. 31B is a schematic cross-sectional view showing an operation of the manipulation input device according to the second embodiment of the present invention when a force magnitude is adjusted.

FIG. 36A is a schematic view showing a first configuration example for regulating a use range of an elastic member.

FIG. 36B is a schematic view showing the first configuration example for regulating the use range of the elastic member.

DETAILED DESCRIPTION OF THE INVENTION

Hereinafter, embodiments of the present invention will be described with reference to the attached drawings. In all the drawings, even when the embodiments are different from each other, the same or equivalent members are assigned the same symbols, and so a common description will be omitted.

First Embodiment

A manipulation input device according to a first embodiment of the present invention and a manipulator system having the same will be described.

Figure 1:
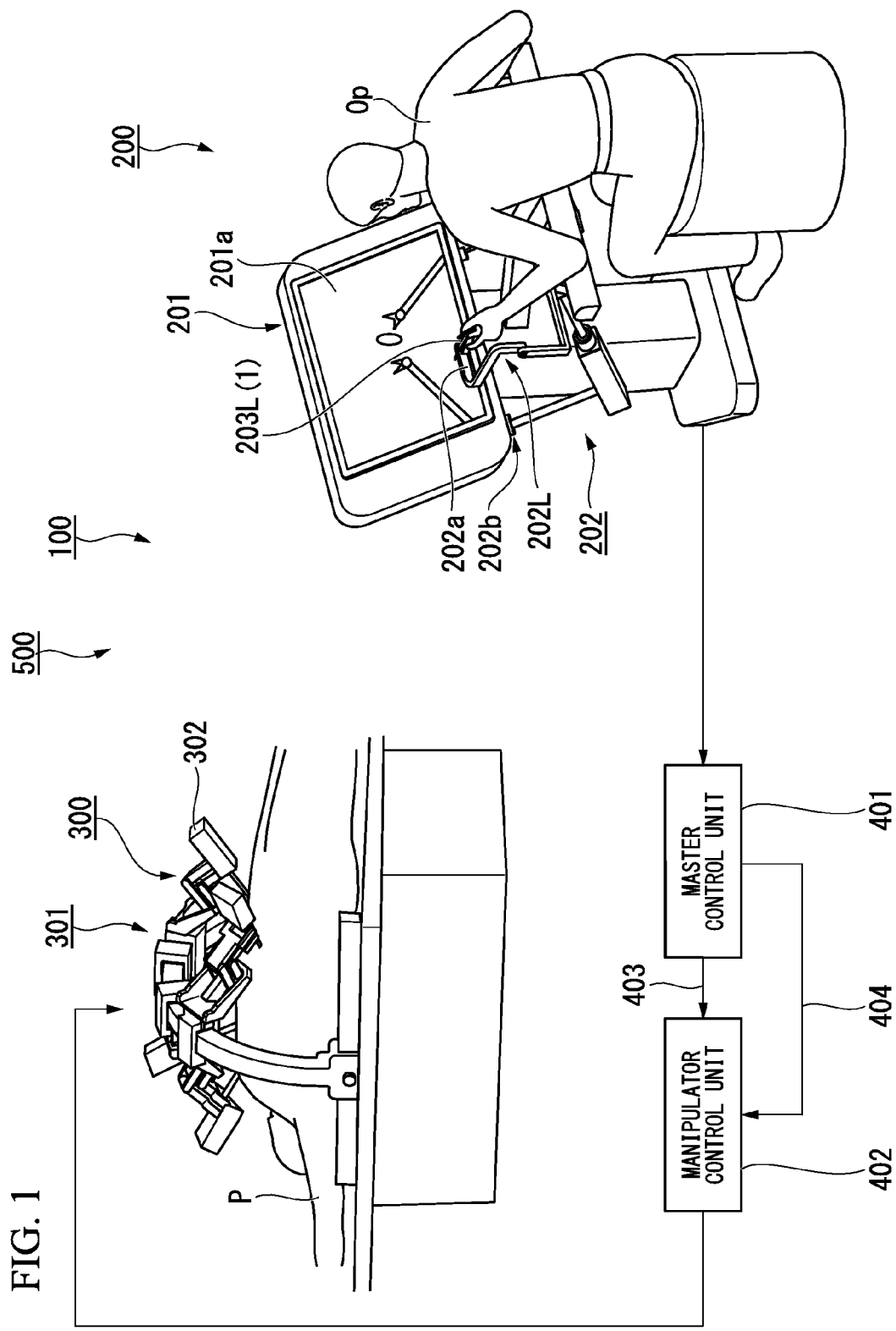
FIG. 1 is a schematic perspective view showing an appearance of a manipulator system having a manipulation input device according to a first embodiment of the present invention.
Figure 2A:
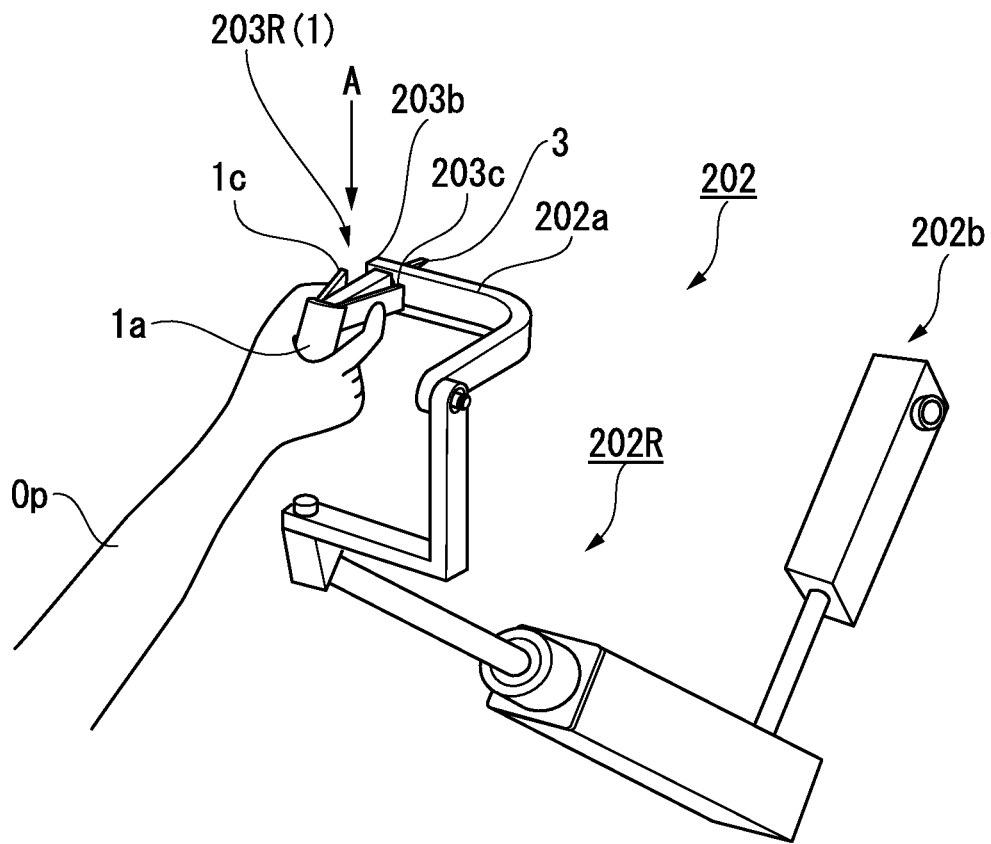
FIG. 2A is a schematic perspective view showing another manipulation input device in the manipulator system of FIG. 1.
Figure 2B:
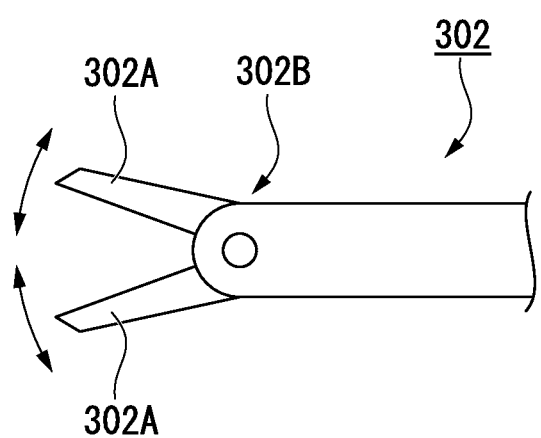
FIG. 2B is a schematic partial enlarged view showing a distal end of a treatment tool in the manipulator system of FIG. 1.

FIG. 1 is a schematic perspective view showing an appearance of a manipulator system having a manipulation input device according to a first embodiment of the present invention. FIG. 2A is a schematic perspective view showing another manipulation input device in the manipulator system of FIG. 1. FIG. 2B is a schematic partial enlarged view showing a distal end of a treatment tool. FIGS. 3A and 3B are schematic partial cross-sectional views showing configurations of opened and closed states of the manipulation input device according to the first embodiment of the present invention.

As shown in FIG. 1 (a partial configuration of which is shown in FIGS. 2A and 2B), a master-slave manipulator (manipulator system) 500 of the present embodiment is, for instance, a medical manipulator for performing surgery. The master-slave manipulator 500 includes a slave manipulator (manipulated device) 300 and a manipulation input device 100 that receives manipulation input from an operator Op to remotely control operation of the slave manipulator 300.

The slave manipulator 300 includes a plurality of treatment tools 302, slave arms 301 that movably support the treatment tools 302 around a patient P, and a manipulator control unit 402 that controls operation of movable parts of each treatment tool 302 and each slave arm 301.

A variety of surgical instruments and treatment tools used for surgery may be adopted as the treatment tools 302. However, as shown in FIG. 2B, the treatment tool such as a forceps or a needle holder for which opened/closed parts 302A opened/closed at a distal end thereof and an opening/closing drive part 302B closing/opening the opened/closed parts 302A are provided will be described by way of example.

Further, each treatment tool 302 is detachably installed on a distal end of each slave arm 301 (an end directed toward a body cavity of the patient P), and can be exchanged as needed.

The slave arm 301 is configured of an articulated arm that holds the treatment tool 302 at a proper position and in a proper orientation. The slave arm 301 is electrically connected to the manipulator control unit 402, and thus is configured so that operation thereof is controlled in response to a control signal from the manipulator control unit 402.

Based on a control signal from a master control unit 401 to be described below, the manipulator control unit 402 controls the slave manipulator 300, and receives position information about each movable part and a detection signal required to control each movable part from the slave manipulator 300. To this end, the manipulator control unit 402 is electrically connected with the master control unit 401 to be described below and each movable part of the slave manipulator 300.

As shown in FIG. 1, the manipulation input device 100 includes a master input unit 200 and the master control unit (manipulation input control unit) 401.

The master input unit 200 functions as a master that transfers manipulation from the operator Op to the slave manipulator 300. The master input unit 200 includes a display unit 201, a master arm 202, and master grips (manipulation units) 203L and 203R.

The display unit 201 is electrically connected to an endoscope (not shown) and the master control unit 401. The display unit 201 displays information from the endoscope and the master control unit 401, thereby enabling the operator Op to watch the information.

As a type of the information displayed by the display unit 201, for instance, pictures of a surgical spot and its surroundings of the patient P which are photographed by the endoscope, a manipulation input screen in which an input operation is performed by an input means (not shown) such as a foot switch, a variety of pieces of information for the operator OP, and text and images, such as, guidance, and warning messages, may be enumerated.

The master arm 202 transfers manipulation of the operator Op to manipulates a position and a orientation of the slave arm 301 in the slave manipulator 300, to the slave manipulator 300. The master arm 202 is connected to be able to communicate with the master control unit 401.

The master arm 202 of the present embodiment is configured of two articulated arms 202L (see FIG. 1) and 202R (see FIG. 2A), arm proximal ends 202b of which are coupled in the master input unit 200, for instance, below the display unit 201 in place.

The articulated arms 202L and 202R are disposed in front of the display unit 201 such that the operator Op can manipulate the articulated arms while watching the display unit 201.

Further, the articulated arms 202L and 202R correspond to the manipulation inputs caused by left and right hands of the operator Op, respectively.

Arm distal ends 202a of the articulated arms 202L and 202R on the side of the operator Op are provided with master grips 203L and 203R which the operator Op grasps to perform the manipulation input.

Each of the articulated arms 202L and 202R is equipped with encoders in each joint, each of which detects an amount of operation of each joint. The articulated arms 202L and 202R are configured to allow an output of each encoder to be sent to the master control unit 401 as a manipulation signal of each joint.

The master grips 203L and 203R are manipulated by the left and right hands of the operator Op, respectively, thereby performing manipulation inputs for the slave arms 301 corresponding to the articulated arms 202L and 202R and for the treatment tools 302 installed on the slave arms 301.

The master grips 203L and 203R may be formed in planarly symmetrical shapes so as to be easily grasped and manipulated by the respective left and right hands. However, as shown in FIGS. 3A and 3B, the following description will be made regarding an example in which any one of the master grips 203L and 203R configuring a master grip (manipulation unit) 1 of the same shape. FIGS. 3A and 3B are depicted as plan views when viewed from the arrow A of FIG. 2A.

As shown in FIGS. 3A and 3B, the master grip 1 is generally configured of a grip part (manipulation unit main body) 1a, a casing unit 1b, manipulation handles 1c, a displacement shaft 1f, a spring 2 (manipulation resistance generator), a force magnitude adjusting unit 3, and an angle detector 4. Further, the force magnitude adjusting unit 3 is configured of a force magnitude adjusting member 3a and a rotation manipulation unit 3b.

As shown FIG. 2A, the grip part 1a is a cylindrical body which the operator Op grasps with one hand. The grip part 1a is provided with the casing unit 1b at one end thereof which extends toward the arm distal end 202a.

The casing unit 1b is coupled with the arm distal end 202a at a distal end thereof.

Further, as shown in FIG. 3A, a pair of manipulation handles 1c are movably supported at one end of the grip part 1a so as to be able to change an opening/closing angle in a V-shaped opened state with the casing unit 1b sandwiched therebetween.

In the present first embodiment of the present invention, one end of each manipulation handle 1c is pivotally supported by a rotation shaft 1d installed in the grip part 1a, and the displacement shaft 1f is installed in the casing unit 1b to be able to move forward or backward in an extending direction of the casing unit 1b. The displacement shaft 1f is coupled with middle portions of the manipulation handles 1c by links 1e.

For this reason, when the displacement shaft 1f is caused to move forward or backward, the manipulation handles 1c move in response to an amount of forward/backward movement, and the opening/closing angle of the manipulation handles 1c is configured to be changed.

As shown in FIG. 3B, when the opening/closing angle of the manipulation handles 1c becomes minimum, an inner side of each manipulation handle 1c comes into contact with a side of the casing unit 1b. In this case, the displacement shaft 1f moves backward to a position spaced apart from the grip part 1a to the utmost.

Hereinafter, for convenience of directional reference in the master grip 1, a side of the casing unit 1b moving toward the grip part 1a in a displacement direction of the displacement shaft 1f may be called a proximal end, whereas a side of the casing unit 1b moving away from the grip part 1a may be called a distal end.

In the casing unit 1b, the spring 2 (manipulation resistance generator or elastic member) configured of a compression coil spring is coupled to an end of the distal end of the displacement shaft 1f via, for instance, a planar spring coupling part 1g.

Further, the other end of the spring 2 is engaged on a planar spring holding part 1h, which is supported to be able to move forward or backward in the displacement direction of the displacement shaft 1f, by the force magnitude adjusting member 3a installed to be able to move forward or backward from the distal end toward the proximal end of the casing unit 1b.

The forward or backward movement of the force magnitude adjusting member 3a may be configured to be performed manually or automatically. In the present first embodiment of the present invention, the manual adjustment is adopted. For this reason, the force magnitude adjusting member 3a of the present first embodiment of the present invention configures a manual adjustment mechanism.

That is, in the present first embodiment of the present invention, a screw member screwed on the distal end of the casing unit 1b is used as the force magnitude adjusting member 3a. The rotation manipulation unit 3b that is provided outside the distal end of the casing unit 1b and is connected with the distal end of the force magnitude adjusting member 3a is manually rotated, and thus the force magnitude adjusting member 3a moves forward or backward with respect to the casing unit 1b. Thereby, a position of the spring holding part 1h can move forward or backward in the displacement direction of the displacement shaft 1f.

In the present first embodiment of the present invention, as shown in FIG. 2A, the force magnitude adjusting unit 3 is configured to protrude through the arm distal end 202a in an outward direction in a state in which the casing unit 1b is coupled to the arm distal end 202a. For this reason, even when the casing unit 1b is coupled to the arm distal end 202a, the manipulation by the operator Op is possible.

The angle detector 4 detects an amount of displacement of each manipulation handle 1c, and transmits information about the displacement amount to the master control unit 401. The angle detector 4 is installed in the grip part 1a, and is electrically connected with the master control unit 401 by wiring (not shown).

The angle detector 4 is not particularly limited in the configuration. For example, the angle detector 4 may be configured to detect the information on the displacement amount of each manipulation handle 1c from an amount of rotating around each rotation shaft 1d. In the present first embodiment of the present invention, the configuration of detecting the forward/backward movement amount of the displacement shaft 1f is adopted. Further, the angle detector 4 may be disposed outside the grip part 1a. In this case, a shaft moving forward or backward in response to the opening/closing of the manipulation handles 1c is guided into the master arm 202, and is detected by the angle detector 4 inside the master arm 202.

Further, an example of the angle detector 4 may include a rotary encoder or a linear encoder. When the rotary encoder is adopted in the present first embodiment of the present invention, the rotary encoder is engaged with the displacement shaft 1f via a conversion mechanism such as a rack and pinion that convert an amount of linear movement of the displacement shaft 1f into an angle of rotation.

In addition, the angle detector 4 may include an absolute type or an increment type. Further, the angle detector 4 is not limited by the type as long as it is a potentiometer other than the encoder or a sensor capable of detecting its other angles. When the increment type is adopted, a proper reference position correcting means is provided. Thereby, displacement or a displacement angle is configured to be able to be detected from a given reference position.

The master control unit 401 receives the manipulation signal sent from the master input unit 200, analyzes a driving amount of each movable part serving as a control target of the slave manipulator 300 for realizing an operation based on the manipulation signal, and sends a movable part selection signal 404 and a command value 403 for the movable part selected by the movable part selection signal 404 to the manipulator control unit 402.

Here, the movable part selection signal 404 is independently assigned to each movable part, such as a joint, of the slave arm 301 and each movable part of the treatment tool 302 held by the slave arm 301.

The master control unit 401 may analyze the manipulation signal from each joint from the master arm 202, calculate positions and orientations of the master grips 203L and 203R, and generate a command value 403 of each movable part of the slave arm 301 required to control the position and orientation of the distal end of the treatment tool 302 supported on the slave arm 301 according to this calculation. The command value 403 is sent to the manipulator control unit 402 along with the movable part selection signal 404 corresponding to each movable part.

Further, based on the output signal that is sent from each angle detector 4 corresponding to each of the master grips 203L and 203R to the master control unit 401, the master control unit 401 may also generate the command value 403 corresponding to the movable part such as a forceps that conducts an opening/closing operation and is installed on the distal end of each treatment tool 302. This command value 403 is sent to the manipulator control unit 402 along with the movable part selection signal 404 corresponding to this movable part.

Here, a correspondence relation between the output signal of the angle detector 4 and the command value 403 is stored in a storage unit (not shown) of the master control unit 401, for instance, as a table or transform data. This correspondence relation may be set as needed. For example, the opening/closing angle of the master grip 1 and that of the distal end of each treatment tool 302 may be identical correspondence, linear correspondence based on an appropriate scale factor, or correspondence with non linearity.

In order to realize an operation of the command value 403 sent from the master control unit 401, the manipulator control unit 402 communicates with each movable part of the slave manipulator 300 which is selected by the movable part selection signal 404, thereby controlling the operation of each movable part.

In the present first embodiment of the present invention, the master control unit 401 adopts a computer, which is configured of a central processing unit (CPU), a memory, an input/output interface, and an external storage, as a device configuration. This computer is configured to execute a control program realizing the aforementioned control function.

Next, an operation of the master-slave manipulator 500 of the present first embodiment of the present invention will be described based on the operation of the master grip 1.

Figure 5A:
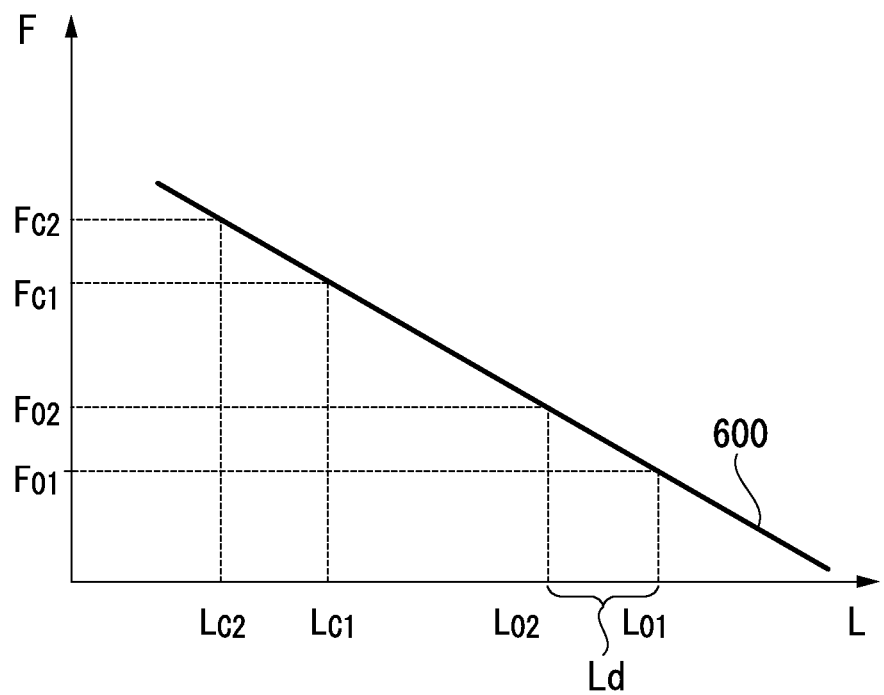
FIG. 5A is a graph for describing a principle of the force magnitude adjustment.
Figure 5B:
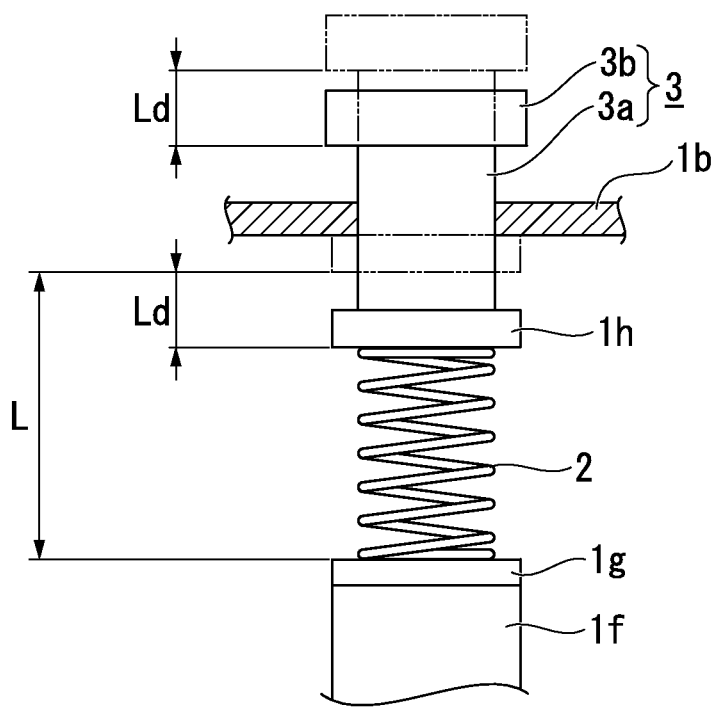
FIG. 5B is a schematic view for describing the principle of the force magnitude adjustment.

FIGS. 4A and 4B are schematic partial cross-sectional views showing opened and closed states of the manipulation input device according to the first embodiment of the present invention when performing force magnitude adjustment. FIG. 5A is a graph for describing a principle of the force magnitude adjustment. In FIG. 5A, the horizontal axis indicates a length L of a spring, and the vertical axis indicates a spring force F. FIG. 5B is a schematic view for describing the principle of the force magnitude adjustment.

According to the master-slave manipulator 500, as shown in FIG. 1, the operator Op grasping the master grips 203L and 203R can conduct manipulation of changing positions and orientations of the master grips 203L and 203R while watching the display unit 201. In connection with this configuration, output signals of the encoders from the movable parts of the master arms 202 are sent to the master control unit 401.

The master control unit 401 analyzes these output signals to generate command values 403 of the movable parts of the slave arms 301 for driving the slave manipulator 300 corresponding to the positions and orientations of the respective master grips 203L and 203R, and sends the generated command values 403 to the manipulator control unit 402.

The manipulator control unit 402 converts the sent command values 403 into driving signals of the slave arms 301, and sends the converted driving signals to the slave arms 301. Thereby, the slave arms 301 are subjected to drive control, and thus positions and orientations of the distal ends of the treatment tools 302 are controlled corresponding to the positions and orientations of the respective master grips 203L and 203R.

On the other hand, the operator Op parallelly manipulates the manipulation handles 1c of the master grips 203L and 203R as needed, and changes an opening/closing angle of the manipulation handles 1c. Here, since the spring 2 is installed in each of the master grips 203L and 203R, when the manipulation handles 1c are closed, the spring 2 is compressed, and an elastic restoring force is generated based on an amount of compression. Thus, the manipulation resistance is transmitted to the hand of the operator Op who manipulates the manipulation handles 1c.

Further, due to the manipulation of the manipulation handles 1c, an output signal of each angle detector 4 of the master grips 203L and 203R is sent to the master control unit 401.

The master control unit 401 generates the command value 403 corresponding to a driving signal of the opening/closing drive part 302B, which is the movable part and closes/opens the opened/closed parts 302A installed on the distal end of the treatment tool 302 based on the output signal from each angle detector 4, and sends the generated command value 403 to the manipulator control unit 402 along with a movable part selection signal 404 corresponding to the opening/closing drive part 302B. Thereby, the opening/closing drive part 302B undergoes drive control, and thus the opening/closing angle of the opened/closed parts 302A of the treatment tool 302 is controlled based on the opening/closing angle of the manipulation handles 1c.

In this way, the operator Op can perform surgery by remotely controlling the slave manipulator 300 via the master input unit 200.

The manipulation resistance may be desired to be properly modified depending on a preference of each operator, treatment tools used, and a performed procedure, or may be desired to be modified to correct aging degradation of the spring.

In the present first embodiment of the present invention, the force magnitude adjusting member 3a of the force magnitude adjusting unit 3 is forced to move forward or backward. Thereby, the manipulation resistance corresponding to a specific opening/closing angle can be changed.

For example, in the case of the positions of the force magnitude adjusting member 3a as shown in FIGS. 3A and 3B, the operator Op may find it difficult to conduct precise closing manipulation because the manipulation resistance is excessively weak. As shown in FIGS. 4A and 4B, the operator Op manipulates the rotation manipulation unit 3b to displace the force magnitude adjusting member 3a into the casing unit 1b, for instance, by a distance Ld. Thereby, when the spring 2 is compressed, the manipulation resistance can be increased.

When a length of the spring 2 is a length $L_{O1}$ in the case of the maximum opening/closing angle before adjustment (see FIG. 3A), and is a length $L_{C1}$ (where $L_{C1}<L_{O1}$) in the case of the minimum opening/closing angle before adjustment (see FIG. 3B), lengths after the adjustment become a length $L_{O2}=L_{O1}-Ld$, and a length $L_{C2}=L_{C1}-Ld$ as shown in FIGS. 4A and 4B, respectively.

When a spring constant of the spring 2 is constant, as indicated in FIG. 5A by a straight line 600, the length L of the spring 2 before the adjustment is changed within a range from $L_{O1}$ to $L_{C1}$ within the whole range of the opening/closing angle of the manipulation handles 1c. In response to this change, the spring force F is changed within a range from $F_{O1}$ to $F_{C1}$ (where $F_{O1}<F_{C1}$).

In contrast, the length L of the spring 2 after the adjustment is changed within a range from $L_{O2}$ to $L_{C2}$ within the whole range of the opening/closing angle of the manipulation handles 1c. In response to this change, the spring force F is changed within a range from $F_{O2}$ to $F_{C2}$ (where $F_{O2}<F_{C2}$).

For this reason, the spring forces F after the adjustment all become greater than those before the adjustment when the opening/closing angle is constant. The manipulation resistance is increased on the whole. Accordingly, when a reference value of the opening/closing angle is determined, and a force magnitude of the manipulation resistance with respect to this reference value of the opening/closing angle is called a reference force magnitude value, the reference force magnitude value is changed before and after the adjustment.

As a result, after the adjustment, the manipulation resistance can be felt more strongly with respect to the same opening/closing amount. As a result, fine opening/closing manipulation becomes easy.

According to the manipulation input device 100 and the master-slave manipulator 500 of the present first embodiment of the present invention, the manipulation input device 100 is provided with the force magnitude adjusting unit 3, and the operator Op manually adjusts the forward/backward movement amount of the force magnitude adjusting member 3a. Thereby, the relation between the displacement amount of the manipulation handle 1c and the force magnitude of the manipulation resistance can be favorably set. The manipulation resistance can be changed according to a preference of the operator Op, so that manipulability can be improved.

First Modified Example

Next, a first modified example of the present first embodiment of the present invention will be described.

Figure 6:
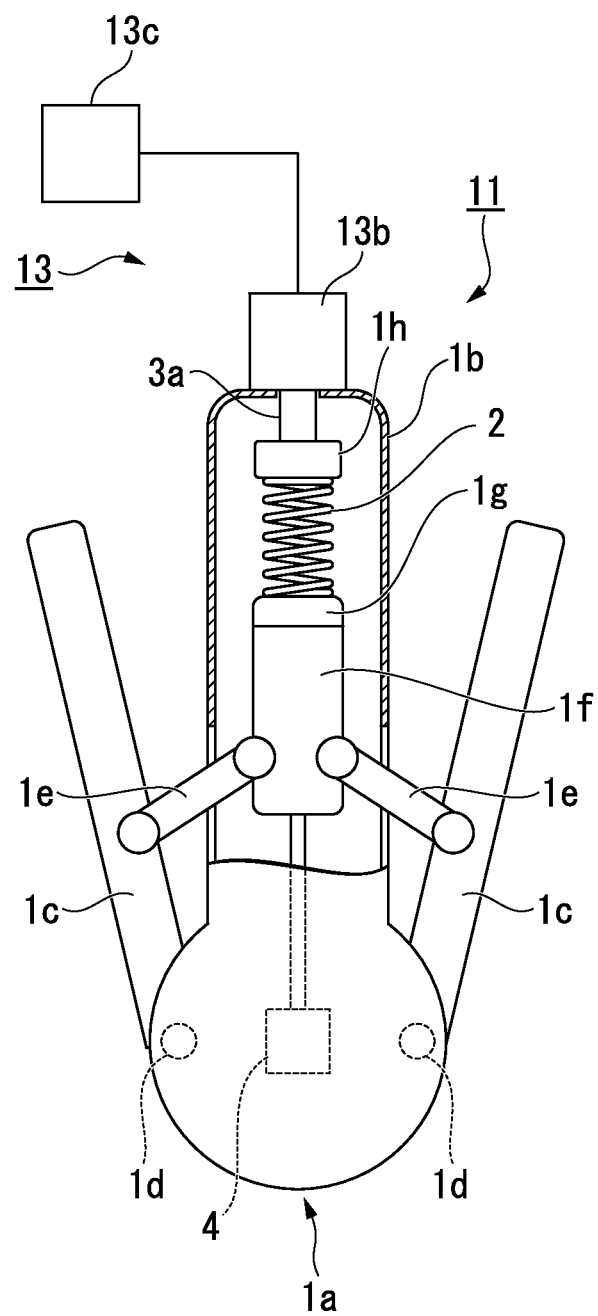
FIG. 6 is a schematic partial cross-sectional view showing a configuration of a manipulation input device of a first modified example of the first embodiment of the present invention.

FIG. 6 is a schematic partial cross-sectional view showing a configuration of a manipulation input device of the first modified example of the first embodiment of the present invention.

As shown in FIG. 6, a master grip (manipulation unit) 11 of the present first modified example of the first embodiment of the present invention includes a force magnitude adjusting unit 13 in place of the force magnitude adjusting unit 3 of the master grip 1 of the first embodiment.

The force magnitude adjusting unit 13 includes an actuator 13b and an adjustment input unit 13c in place of the rotation manipulation unit 3b of the force magnitude adjusting unit 3.

Like the master grip 1 of the first embodiment, the master grip 11 of the present modified example may be used as the master grip 203L or 203R in the master-slave manipulator 500.

The following description will focus on differences from the first embodiment of the present invention.

The actuator 13b is a member that transfers a rotational driving force to a force magnitude adjusting member 3a by means of, for instance, a motor.

The adjustment input unit 13c is an input means adjusting a rotational driving amount of the actuator 13b. As the adjustment input unit 13c, for instance, an analog input element such as a rotary volume or a slide volume, a rotary switch that can be adjusted in a stepwise manner, or a push button switch may be adopted. Further, a numerical value input means such as a numeric keypad may be adopted.

In addition, the adjustment input unit 13c may be configured to be mounted in the master control unit 401, to display a graphical user interface (GUI) screen for an adjustment input on the display unit 201, and to select a proper adjustment value by means of, for instance, an input means or a foot switch attached to the display unit 201.

According to the master grip 11 of the present first modified example of the first embodiment of the present invention, the operator Op performs the input via the adjustment input unit 13c, thereby driving the actuator 13b to be able to manually adjust the manipulation resistance.

For this reason, in comparison with a case in which the operator Op directly screws the force magnitude adjusting member 3a via the rotation manipulation unit 3b, the workability of adjustment is improved.

Particularly, when the adjustment is performed by the foot switch via the display unit 201, the operator Op can adjust the manipulation resistance without separating his/her hand from the master grip 11.

Second Modified Example

Next, a second modified example of the present first embodiment of the present invention will be described.

Figure 7:
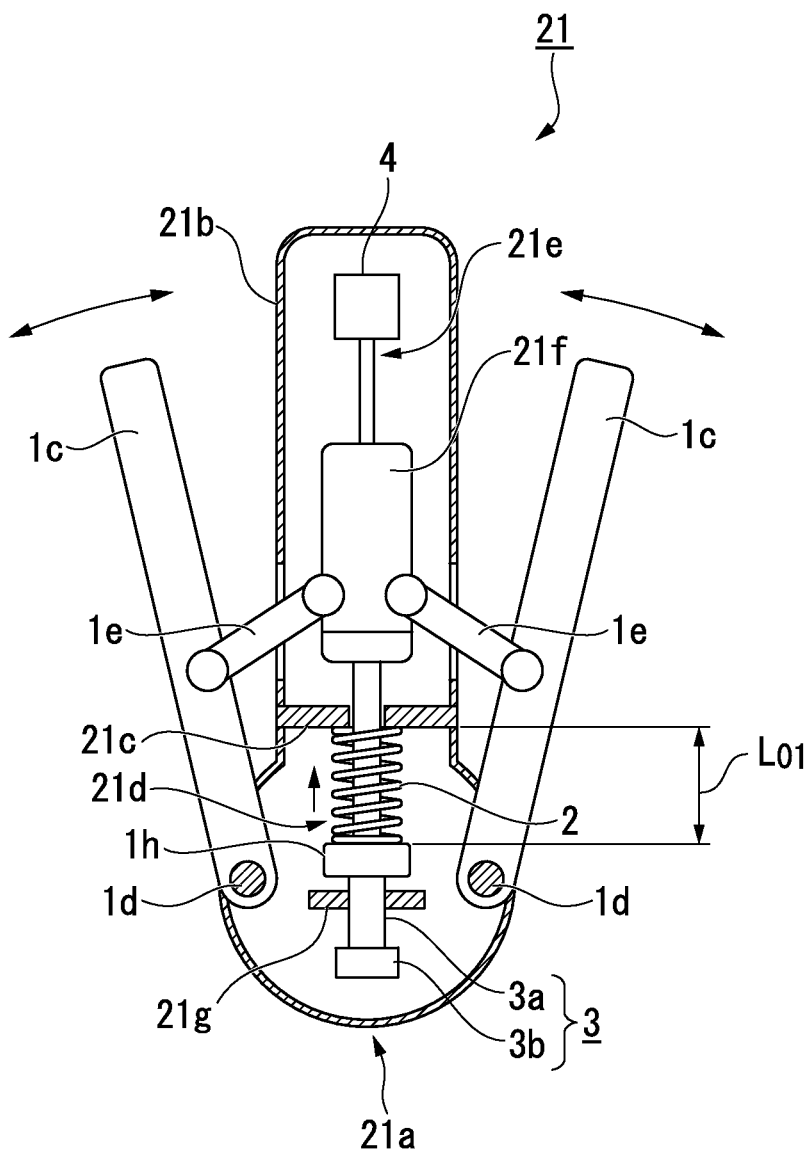
FIG. 7 is a schematic partial cross-sectional view showing a configuration of a manipulation input device of a second modified example of the first embodiment of the present invention.

FIG. 7 is a schematic partial cross-sectional view showing a configuration of a manipulation input device of the second modified example of the first embodiment of the present invention.

As shown in FIG. 7, a master grip (manipulation unit) 21 of the present second modified example of the first embodiment of the present invention includes a displacement shaft 21*f*, a casing unit 21*b*, and a grip part (manipulation unit main body) 21*a* in place of the displacement shaft 1*f*, the casing unit 1*b*, and the grip part 1*a* of the master grip 1 of the first embodiment, and is configured to dispose the spring 2 and the force magnitude adjusting unit 3 in a proximal end-side interior of the casing unit 21*b* and inside the grip part 21*a*. In connection with this configuration, the angle detector 4 detecting an amount of displacement of the displacement shaft 21*f* is displaced to a distal end side of the casing unit 21*b*.

As in the first embodiment, the master grip 21 may be used as the master grip 203L or 203R in the master-slave manipulator 500

The following description will focus on differences from the first embodiment.

The displacement shaft 21*f* is configured with a distal end shaft part 21*e*, which extends in a displacement direction thereof, added at the distal end side of the displacement shaft 1*f* of the first embodiment, and a proximal end shaft part 21*d*, which is penetrable in an axial direction of the spring 2 and has a smaller diameter than an inner diameter of the spring 2, added at the proximal end side of the displacement shaft 1*f*.

The distal end shaft part 21*e* is coupled with the angle detector 4. Thereby, the angle detector 4 is configured to be able to detect the displacement amount of the displacement shaft 21*f*.

The proximal end shaft part 21*d* is inserted into a spring engaging part 21*c* to be described below, and a spring holding part 1*h* is fixed to the proximal end located inside the grip part 21*a*.

The casing unit 21*b* has geometry similar to that of the casing unit 1*b* of the first embodiment. The casing unit 21*b* is configured with a female threaded part for screwing the force magnitude adjusting member 3*a* of the distal end thereof removed. Further, in the proximal end-side interior of the casing unit 21*b*, a through-hole through which the proximal end shaft part 21*d* can move forward or backward is formed, and the spring engaging part 21*c* engaging a distal end of the spring 2 disposed inside the grip part 21*a* is simultaneously provided.

The proximal end shaft part 21*d*, which protrudes from the spring engaging part 21*c* to the proximal end side, is inserted into the spring 2, and a proximal end of the spring 2 is caught by the spring holding part 1*h* fixed to the proximal end shaft part 21*d*.

The grip part 21*a* has geometry similar to that of the grip part 1*a* of the first embodiment, and a support plate 21*g* is installed at a position opposite the spring engaging part 21*c* on a displacement path of the displacement shaft 21*f*.

The support plate 21*g* is a member that includes a female threaded part screw-fitting the force magnitude adjusting member 3*a*, at a proximal end of which a rotation manipulation unit 3*b* is installed, and supports the force magnitude adjusting member 3*a* to be able to move forward or backward in a displacement direction of the displacement shaft 21*f*. The support plate 21*g* is installed at the proximal end side farther than the spring holding part 1*h*.

With this configuration, in the present second modified example, the spring 2 is sandwiched between the spring engaging part 21*c* and the spring holding part 1*h*, and the spring engaging part 21*c* and the spring holding part 1*h* are biased in the displacement direction of the displacement shaft 21*f* by the spring 2.

On the other hand, in the spring engaging part 21*c*, the force magnitude adjusting member 3*a* is in contact from the proximal end side, and a position of the displacement shaft 21*f* is regulated in the displacement direction thereof by the distal end of the force magnitude adjusting member 3*a*.

In this state, for example, when each manipulation handle 1*c* is closed, the displacement shaft 21*f* is displaced to the distal end on the whole. In connection with this configuration, the spring holding part 1*h* is displaced to the distal end side, and the spring 2 is further compressed, so that the manipulation resistance is generated.

In the present second modified example, the operator Op can adjust the manipulation resistance in the same way as in the first embodiment.

That is, in the grip part 21*a*, the rotation manipulation unit 3*b* is manipulated from an opening (not shown). Thereby, when an amount of forward/backward movement of the force magnitude adjusting member 3*a* is changed, a position of the spring holding part 1*h* is displaced. For this reason, a length of the spring 2 can be changed by deforming the spring 2.

For example, when the rotation manipulation unit 3*b* has a rotatable shape in which it can be rotated by a rotating tool such as a driver, the grip part 21*a* is provided with an opening, into which a tip of the rotating tool can be inserted, at a position opposite the proximal end side of the rotation manipulation unit 3*b*. Thereby the rotation manipulation unit 3*b* in the grip part 21*a* can be manipulated.

FIG. 7 shows an example in which the length of the spring 2 is adjusted to $L_{O1}$ at the maximum opening/closing angle of the manipulation handle 1*c*. When the force magnitude adjusting member 3*a* is displaced to the distal end side by Ld, the length of the spring is adjusted to $L_{O2}$, and the manipulation resistance can be increased in the same way as in the first embodiment of the present invention.

In this way, the present second modified example of the first embodiment of the present invention is different from the first embodiment in that the force magnitude adjusting member 3*a* and the rotation manipulation unit 3*b* are installed at the proximal end side, but it is similar to the first embodiment in that a relation between a displacement amount of each manipulation handle 1*c* and a force magnitude of the manipulation resistance can be favorably set. Thereby, the manipulation resistance can be changed according to a preference of the operator Op, so that manipulability can be improved.

Further, the rotation manipulation unit 3*b* is installed at the proximal end side adjacent to the operator Op. For this reason, an adjustment task of the operator Op becomes easier.

Third Modified Example

Next, a third modified example of the present first embodiment will be described.

Figure 8:
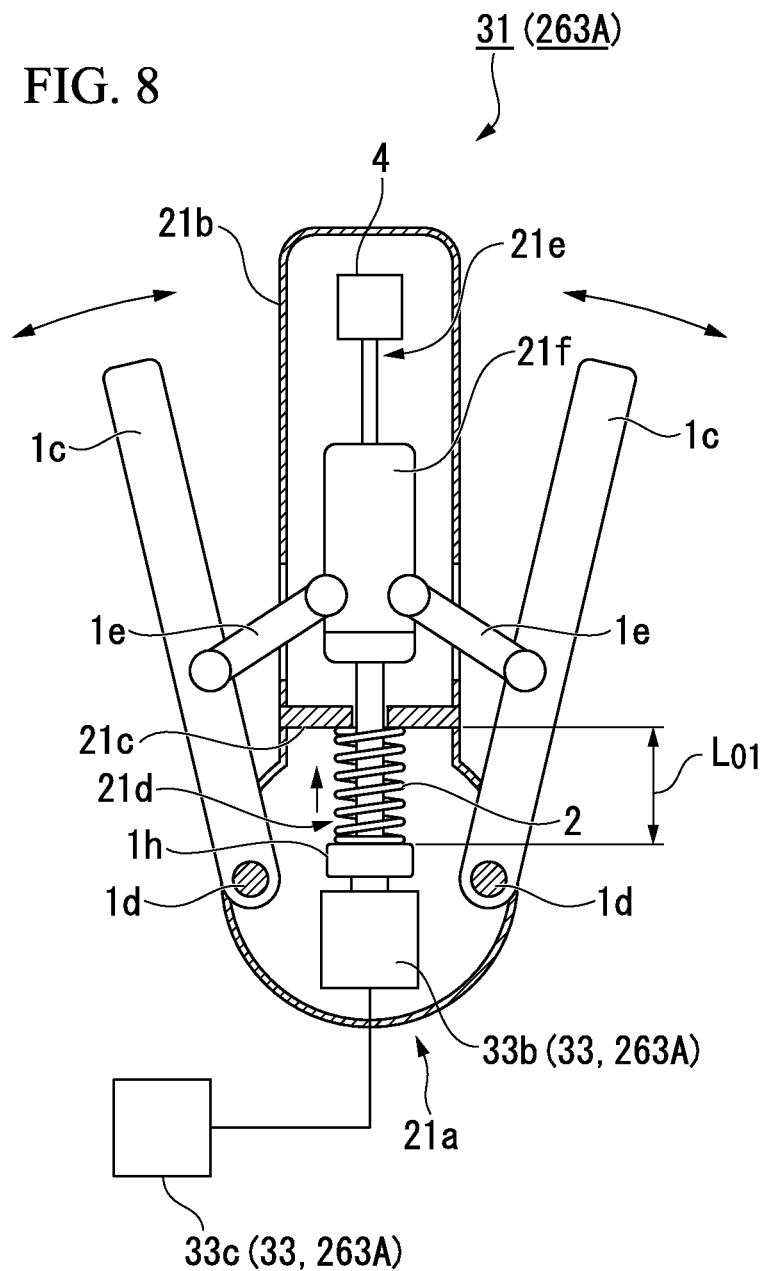
FIG. 8 is a schematic partial cross-sectional view showing a configuration of a manipulation input device of a third modified example of the first embodiment of the present invention.

FIG. 8 is a schematic partial cross-sectional view showing a configuration of a manipulation input device of the third modified example of the first embodiment of the present invention.

As shown in FIG. 8, a master grip (manipulation unit) 31 of the present modified example includes a force magnitude adjusting unit 33 configured of an actuator 33b and an adjustment input unit 33c in place of the force magnitude adjusting unit 3 of the master grip 21 of the second modified example.

As in the first embodiment of the present invention, the master grip 31 may be used as the master grip 203L or 203R in the master-slave manipulator 500

The following description will focus on differences from the second modified example.

The actuator 33b is a linear actuator that moves the spring holding part 1h forward or backward in the displacement direction of the displacement shaft 21f. The actuator 33b is fixed inside the grip part 21a. The actuator 33b has a function of combining the force magnitude adjusting member 3a and the actuator 13b of the first modified example of the present invention.

The adjustment input unit 33c is an input means that adjusts an amount of forward/backward movement of the actuator 33b, and may adopt a configuration similar to that of the adjustment input unit 13c of the first modified example of the present invention.

The master grip 31 of the present third modified example is configured with the adjustment means of the second modified example replaced with the actuator 33b. For this reason, an operator Op can manually adjust manipulation resistance via the adjustment input unit 33c. Thus, in comparison with the case in which the operator Op directly screws the force magnitude adjusting member 3a via the rotation manipulation unit 3b, workability of the adjustment is improved.

Particularly, when the adjustment is performed by a foot switch via the display unit 201, the operator Op can adjust the manipulation resistance without separating his/her hand from the master grip 11.

Fourth Modified Example

Next, a fourth modified example of the present first embodiment of the first embodiment of the present invention will be described.

Figure 9:
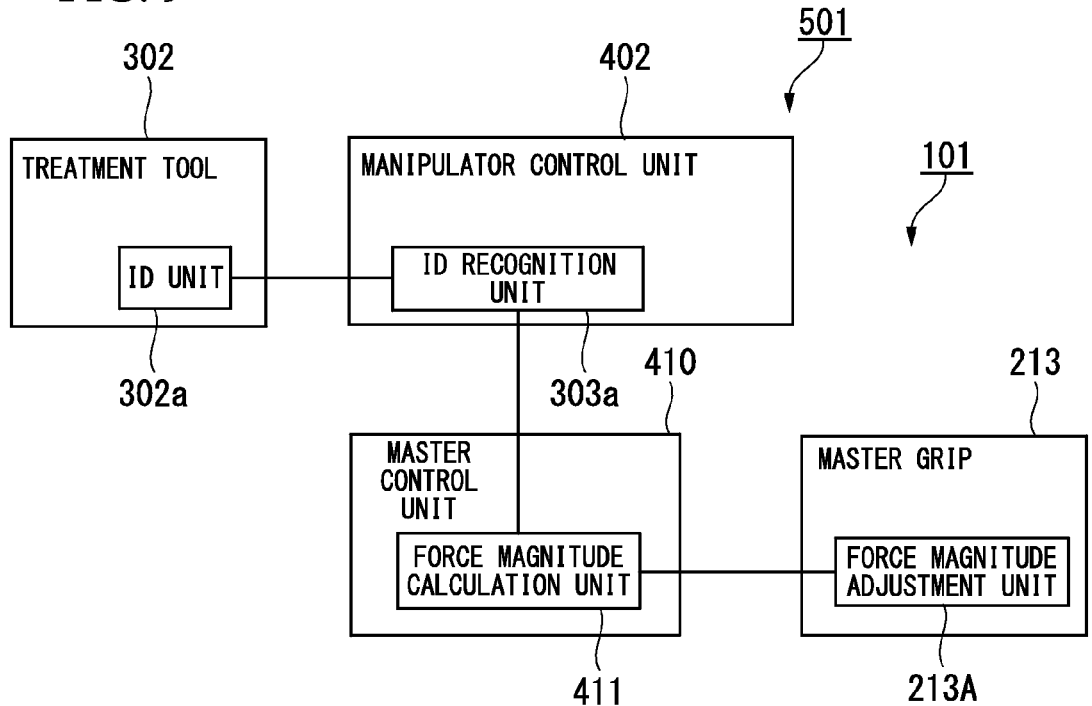
FIG. 9 is a functional block diagram showing a functional configuration of main parts in a manipulation input device according to a fourth modified example of the first embodiment of the present invention.

FIG. 9 is a functional block diagram showing a functional configuration of main parts in a manipulation input device according to the fourth modified example of the first embodiment of the present invention.

As shown in FIG. 9, a master-slave manipulator (manipulator system) 501 of the present fourth modified example includes a manipulation input device 101 in place of the manipulation input device 100 of the master-slave manipulator 500 of the first embodiment. The master-slave manipulator 501 is configured with an identifier (ID) unit 302a and an ID recognition unit 303a added to a treatment tool 302 and a manipulator control unit 402, respectively.

The manipulation input device 101 includes a master grip (manipulation unit) 213 and a master control unit (manipulation input control unit) 410 in place of the master grip 1 and the master control unit 401 of the manipulation input device 100 of the first embodiment.

The following description will focus on differences from the first embodiment.

The master grip 213 includes a force magnitude adjusting unit 213A in place of the force magnitude adjusting unit 3 of the master grip 1 of the first embodiment.

The force magnitude adjusting unit 213A deforms a spring 2 to change a spring length based on a control signal from the master control unit 410, thereby changing a force magnitude of manipulation resistance. As a configuration of the force magnitude adjusting unit 213A, a configuration combining the force magnitude adjusting member 3a and the actuator 13b like the force magnitude adjusting unit 13 of the first modified example, or a configuration in which the spring holding part 1h is directly moved forward or backward using the actuator 33b like the force magnitude adjusting unit 33 of the third modified example may be adopted.

However, in the configuration of the force magnitude adjusting unit 213A, the adjustment input unit 13c or 33c is not provided. The actuator 13b or 33b is electrically connected with the master control unit 410, and thus a movable part of the actuator 13b or 33b is driven by the control signal from the master control unit 410. Thereby, an amount of forward/backward movement of the force magnitude adjusting unit 213A that displaces the spring holding part 1h is configured to be able to be adjusted.

The master control unit 410 is configured with a force magnitude calculation unit 411 added to the master control unit 401 of the first embodiment.

The force magnitude calculation unit 411 communicates with the manipulator control unit 402 to acquire identification information of the treatment tool 302 severing as a manipulation target of the master grip 213. Based on adjustment information stored in advance corresponding to this identification information, the amount of forward/backward movement of the force magnitude adjusting unit 213A which is capable of obtaining desired manipulation resistance is calculated. A driving signal corresponding to the forward/backward movement amount is sent to the force magnitude adjusting unit 213A.

Here, as the adjustment information, a relation of a reference force magnitude value of the manipulation resistance with respect to a reference value of a proper opening/closing angle may be recognized. For example, when the treatment tool 302 is a needle holder grasping a needle having a fixed size, the force magnitude of the manipulation resistance which is capable of obtaining a good sense of manipulation may be considered to be provided at an opening/closing angle when the needle is grasped.

When this information is acquired as the adjustment information, the force magnitude calculation unit 411 calculates an amount of change of a desired spring length based on a spring constant of the spring 2 and a relation of the spring length with respect to the opening/closing angle, and an amount of forward/backward movement of the force magnitude adjusting unit 213A which corresponds to this change amount.

Further, when a treatment tool that requires no opening/closing operation is used (e.g., a knife or a syringe needle), a master force magnitude is set to the maximum so that the grip cannot be opened/closed. This allows the treatment tool such as the knife to be intuitively manipulated without worrying about undesired opening/closing of the grip.

The ID unit 302a holds the identification information (hereinafter referred to as "treatment tool identification information") of each treatment tool 302 to be able to be read by the manipulator control unit 402.

The treatment tool identification information which the ID unit 302a holds is not particularly limited as long as it is information for discriminating between suitable manipulation resistances different from each other.

For example, information such as a manufacturing serial number, which uniquely specifies the treatment tool 302, may be adopted as the treatment tool identification information.

However, the treatment tool identification information may be information that specifies a group when grouped according to a type or a characteristic common to a plurality of treatment tools 302.

As an example of the treatment tool identification information, information indicating application-specific types of the treatment tools 302, for instance, an identification code given to each type of a forceps or a needle holder, may be given. Further, an identification code given to each maker of the treatment tools 302, or an identification code given to each model of makers may be given.

Also, when an operator Op who has used each treatment tool 302 is decided in advance, an identification code specifying the user may be used.

In addition, the treatment tool identification information may be used as the identification information for the manipulator control unit 402 identifying the treatment tool 302 mounted on the slave arm 301.

A device configuration of the ID unit 302a is not particularly limited as long as it is capable of being read by the manipulator control unit 402. A variety of nonvolatile memories, IC tags, and identification marks formed on a part of the treatment tool 302 to be mechanically, magnetically, or optically readable may be given as examples.

The ID recognition unit 303a reads the treatment tool identification information from the ID unit 302a when the treatment tool 302 is connected to the slave arm 301, and sends the read information to the force magnitude calculation unit 411. The ID recognition unit 303a is connected to be able to communicate with at least the force magnitude calculation unit 411.

As a device configuration of the ID recognition unit 303a, a proper device configuration may be adopted depending on the device configuration of the ID unit 302a.

For example, when the treatment tool identification information is stored in the nonvolatile memory or the IC tag, a communication means reading out information from the nonvolatile memory or the IC tag may be adopted. Further, when the treatment tool identification information is the mechanically, magnetically, or optically formed identification mark, a contact type sensor, a non-contact type sensor, a magnetic read sensor, or an optical read sensor that detects the information may be adopted.

Next, an operation of the present fourth modified example of the first embodiment of the present invention will be described.

Figure 10:
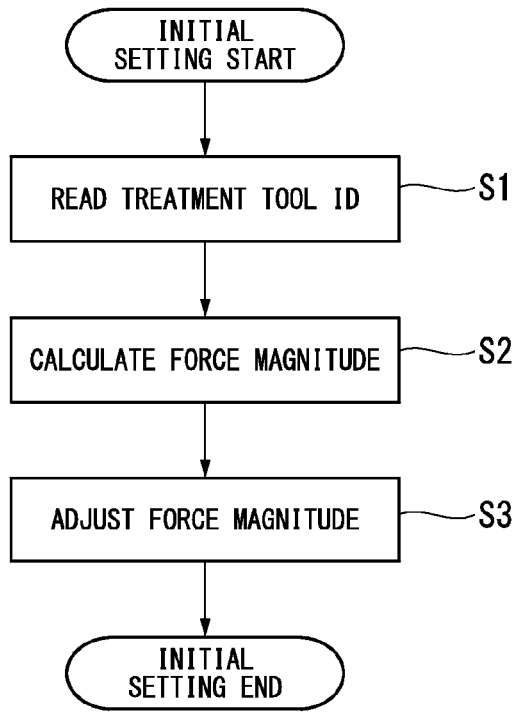
FIG. 10 is a flowchart for describing an operation of the manipulation input device according to the fourth modified example of the first embodiment of the present invention.

FIG. 10 is a flowchart for describing an operation of the manipulation input device according to the fourth modified example of the first embodiment of the present invention.

In the present fourth modified example, when the treatment tool 302 is mounted on the slave arm 301, an initial setting operation of adjusting manipulation resistance as a part of an initialization operation is automatically initiated according to the flowchart shown in FIG. 10.

First, in step S1, the ID recognition unit 303a communicates with the ID unit 302a, and reads treatment tool identification information (abbreviated to "treatment tool ID" in FIG. 10). The ID recognition unit 303a sends the read treatment tool identification information to the force magnitude calculation unit 411 of the master control unit 410.

Next, in step S2, the force magnitude calculation unit 411 calculates a force magnitude set to desired manipulation resistance. That is, the force magnitude calculation unit 411 searches for information corresponding to the treatment tool identification information from pre-stored adjustment information, and calculates an amount of forward/backward movement of the force magnitude adjusting unit 213A which can obtain the desired manipulation resistance.

Subsequently, in step S3, the force magnitude calculation unit 411 sends a driving signal corresponding to the calculated forward/backward movement amount to the force magnitude adjusting unit 213A. Thereby, the force magnitude adjusting unit 213A moves forward or backward, so that a length of the spring 2 is adjusted. Thereby, a range of a spring force F is set on the straight line 600 shown in FIG. 5A.

In this way, the initial setting operation adjusting the manipulation resistance is terminated.

According to the present fourth modified example, the treatment tool 302 is merely mounted on the slave arm 301. Thereby, the manipulation resistance of the master grip 213 is automatically initialized to the predetermined manipulation resistance. For this reason, even when the treatment tools 302 are replaced, the senses of manipulation suitable for the respective treatment tools 302 can always be maintained.

Fifth Modified Example

Next, a fifth modified example of the present first embodiment will be described.

Figure 11:
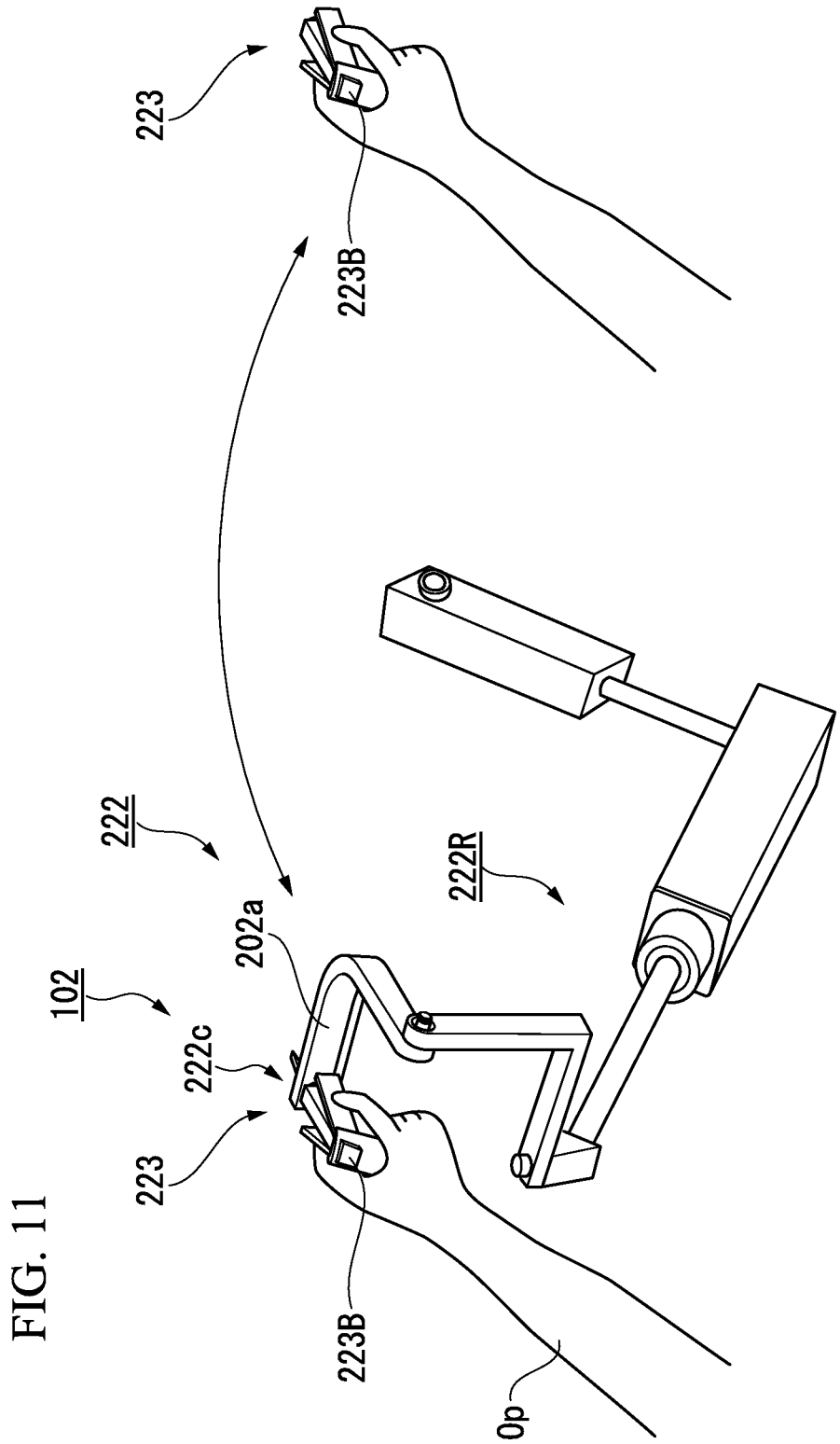
FIG. 11 is a schematic perspective view showing a configuration of main parts in a manipulation input device according to a fifth modified example of the first embodiment of the present invention.
Figure 12:
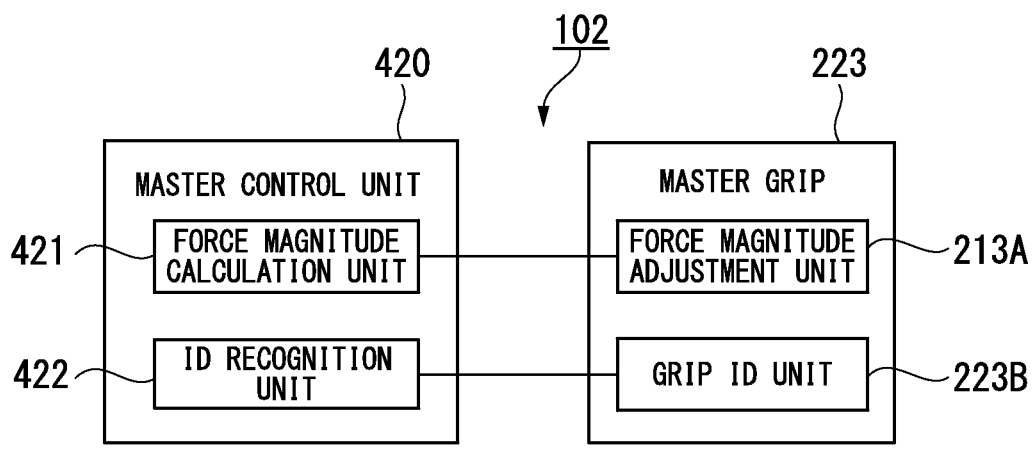
FIG. 12 is a functional block diagram showing a functional configuration of main parts in the manipulation input device according to the fifth modified example of the first embodiment of the present invention.

FIG. 11 is a schematic perspective view showing a configuration of main parts in a manipulation input device according to a fifth modified example of the first embodiment of the present invention. FIG. 12 is a functional block diagram showing a functional configuration of main parts in the manipulation input device according to the fifth modified example of the first embodiment of the present invention.

As shown in FIGS. 11 and 12, a manipulation input device 102 of the present first modified example includes a master arm 222, a master grip (manipulation unit) 223, and a master control unit (manipulation input control unit) 420 in place of the master arm 202, the master grip 1, and the master control unit 401 of the manipulation input device 100 of the first embodiment.

Like the manipulation input device 100, the manipulation input device 102 of the present first modified example may be used as the manipulation input device in the master-slave manipulator 500.

The following description will focus on differences from the first embodiment.

The master arm 222 is configured with a release part 222c that removably mounts a master grip 223 added on each arm distal end 202a of the master arm 202 of the first embodiment. In FIG. 11, of the master arm 222, an articulated arm 222R corresponding to the articulated arms 202R is shown for its configuration, but an articulated arm corresponding to the articulated arms 202L is similarly configured.

The release part 222c has a mechanical coupling structure that mechanically positions and couples the master grip 223 with respect to the arm distal end 202a, and an electrical connecting structure that electrically connects the master grip 223 with the master control unit 420. For this reason, the master grip 223 mounted on the release part 222c can communicate with the master control unit 420 via the release part 222c.

The master grip 223 is configured with a grip ID unit 223B (identification information part) added to the master grip 213 of the fourth modified example, and the master grip 223 is detachably coupled with the release part 222c of the arm distal end 202a as shown in FIG. 11. That is, the master grip 223 is detachably installed on a main body of the manipulation input device including the master arm 222.

The grip ID unit 223B holds identification information (hereinafter referred to as "grip identification information") of each master grip 223 to be able to be read by the master control unit 420.

The grip identification information which the grip ID unit 223B holds is not particularly limited as long as it is information for discriminating between suitable manipulation resistances different from each other.

For example, information such as a manufacturing serial number, which uniquely specifies the master grip 223, may be adopted as the grip identification information.

However, the grip identification information may be information that specifies a group when grouped according to a type or a characteristic common to a plurality of master grips 223.

As an example of the grip identification information, when each master grip 223 is changed depending on a type of the manipulated treatment tool 302, an identification code given to each type of the treatment tools 302 may be given.

Further, when an adjustment range of the manipulation resistance or a magnitude of an adjustment amount accompanied by the adjustment is different because of a difference of, for instance, a spring constant or a spring length of the spring 2 for each master grip 223, an identification code given according to a type of the spring 2 may be given as an example.

A device configuration of the grip ID unit 223B is not particularly limited as long as it can be read by the master control unit 420 or the release part 222c. A variety of nonvolatile memories, IC tags, and identification marks formed on a part of the master grip 223 to be mechanically, magnetically, or optically readable may be given as examples.

As shown in FIG. 12, the master control unit 420 includes a force magnitude calculation unit 421 in place of the force magnitude calculation unit 411 of the master control unit 410 of the fourth modified example, and is configured with an ID recognition unit 422 added.

The force magnitude calculation unit 421 acquires the grip identification information of the mounted master grip 223 via the ID recognition unit 422, calculates a forward/backward movement amount of a force magnitude adjusting unit 213A which can obtain desired manipulation resistance based on pre-stored adjustment information corresponding to the grip identification information, and sends a driving signal corresponding to the forward/backward movement amount to the force magnitude adjusting unit 213A.

When the master grip 223 is connected to the arm distal end 202a, the ID recognition unit 422 reads the grip identification information from the grip ID unit 223B, and sends the read grip identification information to the force magnitude calculation unit 421. The ID recognition unit 422 is connected to be able to communicate with the force magnitude calculation unit 421.

As a device configuration of the ID recognition unit 422, a proper device configuration similar to the ID recognition unit 303a of the fourth modified example may be adopted depending on the device configuration of the grip ID unit 223B Next, an operation of the present fifth modified example of the first embodiment of the present invention will be described.

Figure 13:
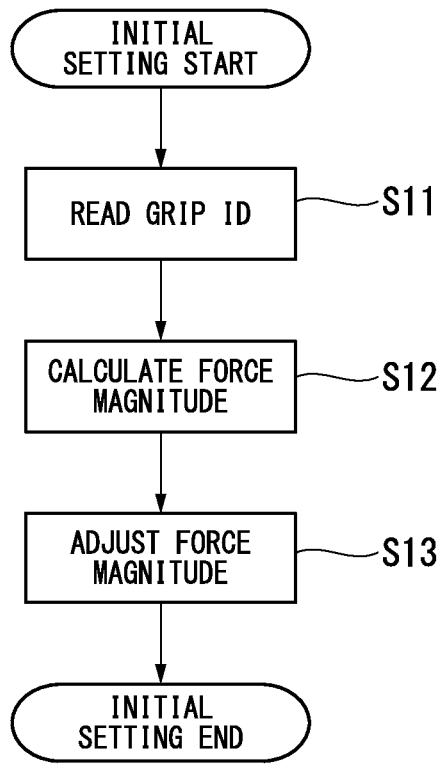
FIG. 13 is a flowchart for describing an operation of the manipulation input device according to the fifth modified example of the first embodiment of the present invention.

FIG. 13 is a flowchart for describing an operation of the manipulation input device according to the fifth modified example of the first embodiment of the present invention.

In the present fifth modified example, when the master grip 223 is mounted on the arm distal end 202a, an initial setting operation of adjusting the manipulation resistance is automatically initiated according to the flowchart shown in FIG. 13 as a part of an initialization operation.

First, in step S11, the ID recognition unit 422 of the master control unit 420 communicates with the grip ID unit 223B, thereby reading grip identification information (abbreviated to "grip ID" in FIG. 13). The ID recognition unit 422 sends the read grip identification information to the force magnitude calculation unit 421.

Next, in step S12, the force magnitude calculation unit 421 calculates a force magnitude set to desired manipulation resistance. That is, the force magnitude calculation unit 421 searches for information corresponding to the grip identification information from pre-stored adjustment information, and calculates a forward/backward movement amount of the force magnitude adjusting unit 213A which can obtain the desired manipulation resistance.

Subsequently, in step S13, the force magnitude calculation unit 421 sends a driving signal corresponding to the calculated forward/backward movement amount to the force magnitude adjusting unit 213A. Thereby, the force magnitude adjusting unit 213A moves forward or backward, so that a length of the spring 2 is adjusted. Thereby, a range of a spring force F is set on the straight line 600 shown in FIG. 5A.

In this way, the initial setting operation of adjusting the manipulation resistance is terminated.

According to the present fifth modified example, the master grip 223 is merely mounted on the arm distal end 202a. Thereby, the manipulation resistance of the master grip 223 is automatically initialized to the predetermined manipulation resistance. For this reason, even when the master grips 223 are replaced, the sense of manipulation suitable for each master grips 223 can always be maintained.

Further, when the information of the manipulation resistance of the master grip 223 is stored according to a preference of an operator Op, the operator Op mounts and uses the master grip 223 on the other manipulation input device 102. Thereby, even in the case of the different manipulation input device 102, the sense of manipulation of the preference is obtained.

Sixth Modified Example

Next, a sixth modified example of the present first embodiment will be described.

Figure 14:
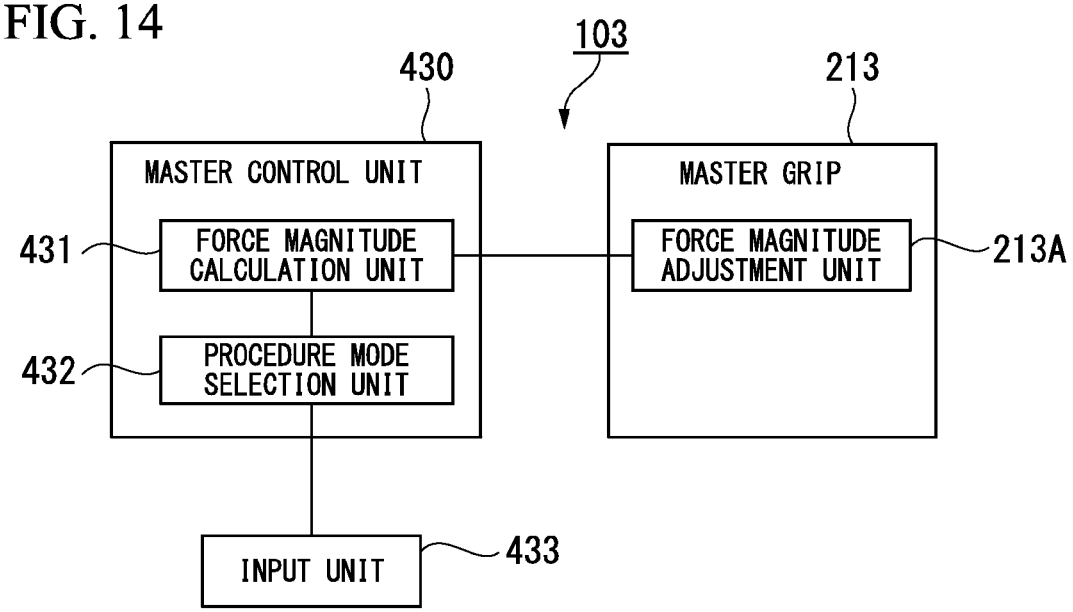
FIG. 14 is a functional block diagram showing a functional configuration of main parts in a manipulation input device according to a sixth modified example of the first embodiment of the present invention.

FIG. 14 is a functional block diagram showing a functional configuration of main parts in a manipulation input device according to the sixth modified example of the first embodiment of the present invention.

As shown in FIG. 14, the manipulation input device 103 of the present sixth modified example includes a master grip 213 and a master control unit (manipulation input control unit) 430 in place of the master grip 1 and the master control unit 401 of the manipulation input device 100 of the first embodiment.

Like the manipulation input device 100, the manipulation input device 103 of the present sixth modified example may be used as the manipulation input device in the master-slave manipulator 500.

The following description will focus on differences from the first embodiment of the present invention and the fourth modified example of the first embodiment of the present invention.

The master control unit 430 includes a force magnitude calculation unit 431 in place of the force magnitude calculation unit 411 of the master control unit 410 of the fourth modified example, and is configured with a procedure mode selection unit (procedure mode input unit) 432 added.

The force magnitude calculation unit 431 acquires procedure mode information sent from the procedure mode selection unit 432 to be described below, calculates a forward/backward movement amount of a force magnitude adjusting unit 213A which can obtain desired manipulation resistance based on pre-stored adjustment information corresponding to the procedure mode information, and sends a driving signal corresponding to the forward/backward movement amount to the force magnitude adjusting unit 213A.

The procedure mode selection unit 432 is electrically connected with an input unit 433 through which an operator Op inputs the procedure mode information, and enables the operator Op to select a procedure mode via the input unit 433.

A dedicated input means such as a rotary switch may be adopted as the input unit 433. However, the procedure mode selection unit 432 may be configured to display a GUI screen for the procedure mode selection on a display unit 201, and to be able to select an appropriate procedure mode using, for instance, an input means or a foot switch attached to the display unit 201.

Here, the procedure mode information refers to information in which a type and a process of the procedure performed by the master-slave manipulator 500 including the manipulation input device 103 are grouped into each desired manipulation resistance, and each is encoded. The procedure modes such as target disease regions (e.g. digestive organs, circulatory organs, orthopedics, or urinary organs), procedure names (gastrectomy, bypass surgery, or prostatectomy), and target manipulation (suture, incision, or dissection) are set, and unique identification codes are set to the respective procedure modes.

The desired manipulation resistance for each procedure is decided so that the sense of manipulation becomes good in consideration of minuteness of a necessary procedure operation and a force magnitude actually applied to a treatment tool.

Next, an operation of the present sixth modified example will be described.

Figure 15:
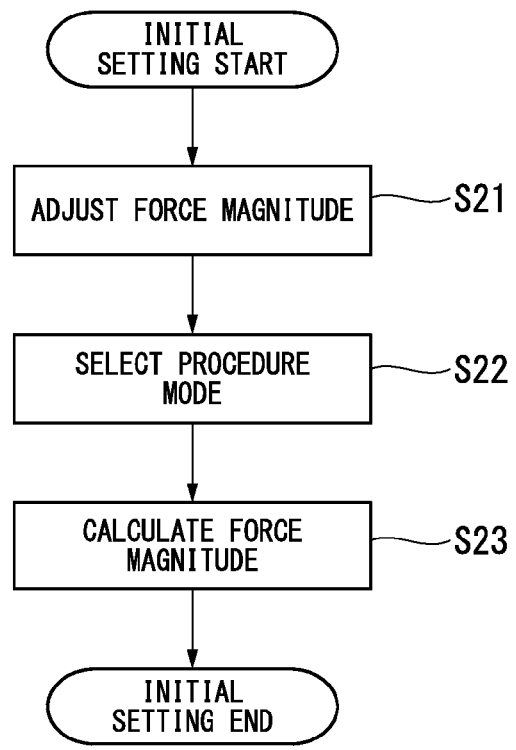
FIG. 15 is a flowchart for describing an operation of the manipulation input device according to the sixth modified example of the first embodiment of the present invention.

FIG. 15 is a flowchart for describing an operation of the manipulation input device according to the sixth modified example of the first embodiment of the present invention.

In the present sixth modified example, prior to initiating one procedure, the master control unit 430 permits selection of the procedure mode. Then, an initial setting operation adjusting manipulation resistance is automatically initiated according to the flowchart shown in FIG. 15.

First, in step S21, an operator Op selects a procedure mode to be performed via the input unit 433.

For example, when the input unit 433 displays a GUI screen on the display unit 201, the GUI screen showing an option of the procedure mode is displayed on the display unit 201 by the procedure mode selection unit 432. Thereby, the operator Op manipulates an input means such as a foot switch to select the procedure mode to be performed from the input means.

When the input from the input unit 433 is performed, the procedure mode selection unit 432 sends the procedure mode information corresponding to the selected procedure mode to the force magnitude calculation unit 431.

Next, in step S22, the force magnitude calculation unit 431 calculates a force magnitude set to desired manipulation resistance. That is, the force magnitude calculation unit 431 searches for information corresponding to the procedure mode information from pre-stored adjustment information, and calculates a forward/backward movement amount of the force magnitude adjusting unit 213A which can obtain the desired manipulation resistance.

Subsequently, in step S23, the force magnitude calculation unit 431 sends a driving signal corresponding to the calculated forward/backward movement amount to the force magnitude adjusting unit 213A. Thereby, the force magnitude adjusting unit 213A moves forward or backward, so that a length of the spring 2 is adjusted. Thereby, a range of a spring force F is set on the straight line 600 shown in FIG. 5A.

In this way, the initial setting operation adjusting the manipulation resistance is terminated.

According to the present sixth modified example, the operator Op need only select the procedure mode. Thereby, the manipulation resistance of the master grip 223 is automatically initialized into the predetermined manipulation resistance. For this reason, the sense of manipulation suitable for each procedure can always be maintained.

Seventh Modified Example

Next, a seventh modified example of the present first embodiment will be described.

Figure 16:
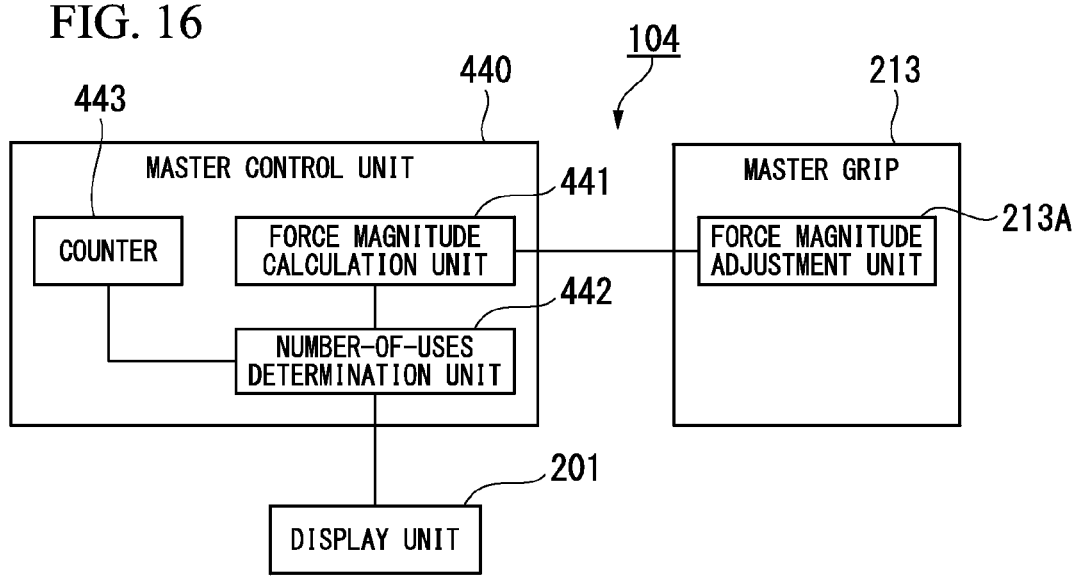
FIG. 16 is a functional block diagram showing a functional configuration of main parts in a manipulation input device according to a seventh modified example of the first embodiment of the present invention.

FIG. 16 is a functional block diagram showing a functional configuration of main parts in a manipulation input device according to the seventh modified example of the first embodiment of the present invention.

As shown in FIG. 16, the manipulation input device 104 of the present seventh modified example of the first embodiment of the present invention includes a master grip 213 and a master control unit (manipulation input control unit) 440 in place of the master grip 1 and the master control unit 401 of the manipulation input device 100 of the first embodiment.

Like the manipulation input device 100, the manipulation input device 104 of the present seventh modified example of the first embodiment of the present invention may be used as the manipulation input device in the master-slave manipulator 500.

The following description will focus on differences from the first embodiment and the fourth modified example.

The master control unit 440 includes a force magnitude calculation unit 441 in place of the force magnitude calculation unit 411 of the master control unit 410 of the fourth modified example, and is configured with a number-of-uses determination unit 442 (a time-dependent change detection unit) and a counter 443 added.

When adjustment of the manipulation resistance is permitted by the number-of-uses determination unit 442 to be described below, the force magnitude calculation unit 441 calculates a forward/backward movement amount of the force magnitude adjusting unit 213A which can obtain desired manipulation resistance based on preset adjustment information, and sends a driving signal corresponding to the forward/backward movement amount to the force magnitude adjusting unit 213A.

The number-of-uses determination unit 442 acquires information about the number of uses of the master grip 213 from the counter 443 that counts the number of uses of the master grip 213, and determines whether or not the number of uses has exceeded a preset upper limit.

When the number of uses has exceeded a preset upper limit, the number-of-uses determination unit 442 sends a disable signal to refuse the adjustment of manipulation resistance to the force magnitude calculation unit 441, and simultaneously displays a warning sign warning that the number of uses has exceeded the upper limit on the display unit 201, and brings the operation of the manipulation input device 104 to an error end.

When the number of uses is less than the upper limit, the number-of-uses determination unit 442 sends an enable signal permitting the adjustment of manipulation resistance to the force magnitude calculation unit 441.

The upper limit of the number of uses is a number of uses at which the number of uses of the master grip 213 increases to cause a change in the characteristic of the spring 2 and thus the manipulation resistance cannot be adjusted within an allowable error range, and is found in advance by means of a test and stored in the number-of-uses determination unit 442.

The counter 443 counts and stores the number of uses of the master grip 213. A storage location of the counter 443 is assigned to a nonvolatile storage region formed on the master control unit 440.

In the present seventh modified example of the first embodiment of the present invention, the number of uses is stored as the number of times which the manipulation resistance of the master grip 213 is adjusted. For this reason, the counter 443 is automatically updated whenever the manipulation resistance of the master grip 213 is adjusted by the master control unit 440.

Next, an operation of the present seventh modified example of the first embodiment of the present invention will be described.

Figure 17:
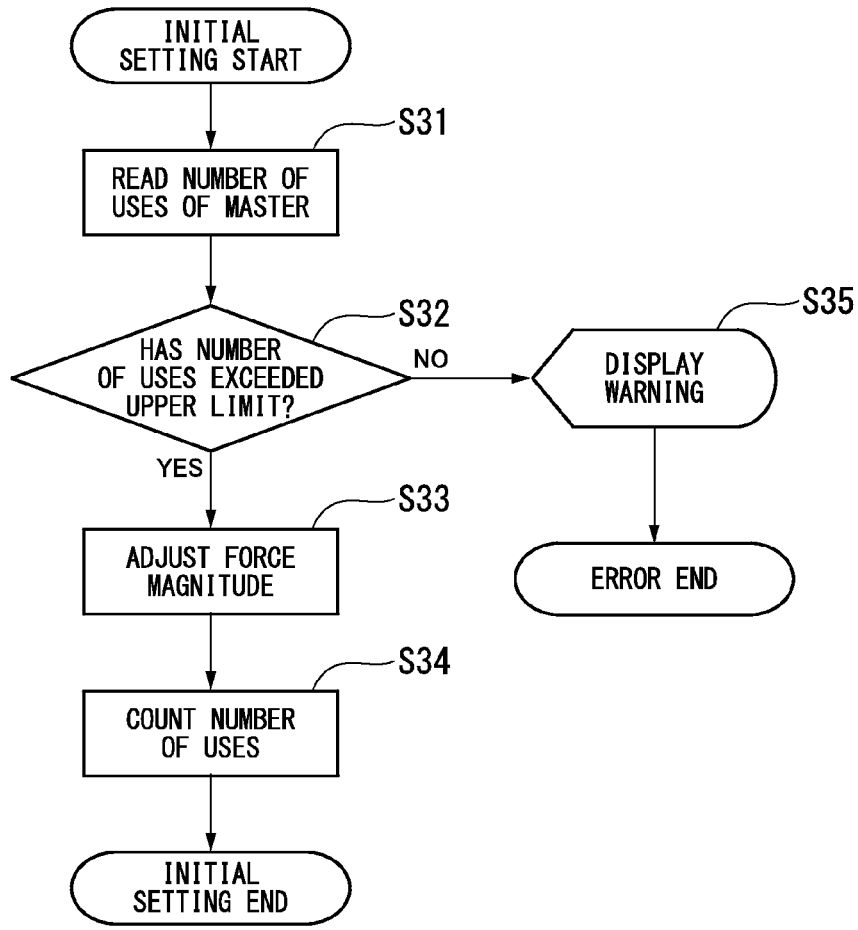
FIG. 17 is a flowchart for describing an operation of the manipulation input device according to the seventh modified example of the first embodiment of the present invention.
Figure 18:
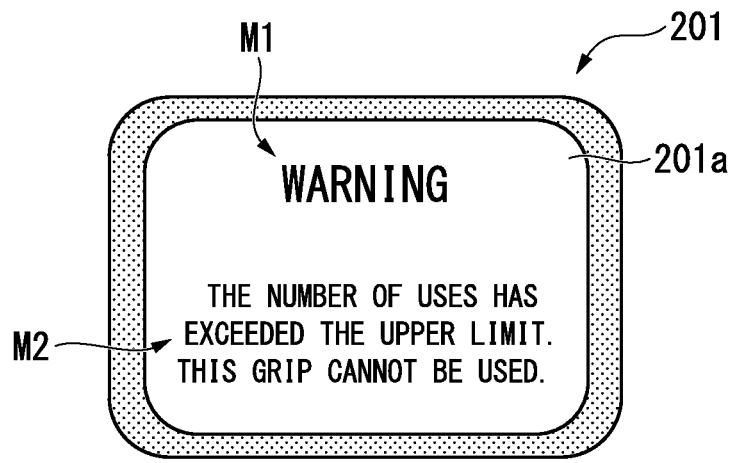
FIG. 18 is a schematic view of a display screen showing an example of a warning sign of the manipulation input device according to the seventh modified example of the first embodiment of the present invention.

FIG. 17 is a flowchart for describing an operation of the manipulation input device according to the seventh modified example of the first embodiment of the present invention. FIG. 18 is a schematic view of a display screen showing an example of a warning sign of the manipulation input device according to the seventh modified example of the first embodiment of the present invention.

The present seventh modified example of the first embodiment of the present invention is an example in which, before the adjustment operation of the manipulation resistance is initiated, the master control unit 440 is configured to automatically determine whether or not the number of uses of the master grip 213 has exceeded the upper limit in accordance with the flowchart shown in FIG. 17, and to perform the adjustment operation of the manipulation resistance only when the number of uses is less than the upper limit.

First, in step S31, the number-of-uses determination unit 442 acquires information about the current number of uses of the master grip 213 from the counter 443.

Next, in step S32, the number-of-uses determination unit 442 compares the acquired information of the number of uses and the pre-stored upper limit of the number of uses.

When the number of uses has exceeded the upper limit, the number-of-uses determination unit 442 sends a disable signal to refuse the adjustment of the manipulation resistance to the force magnitude calculation unit 441, and proceeds to step S35.

When the number of uses is less than the upper limit, the number-of-uses determination unit 442 sends an enable signal permitting the adjustment of the manipulation resistance to the force magnitude calculation unit 441, and proceeds to step S33.

In step S35, the number-of-uses determination unit 442 displays a warning sign warning that the number of uses has exceeded the upper limit on the display unit 201, and then brings the operation of the manipulation input device 104 to an error end.

As examples of the warning sign, as shown in FIG. 18, a text-based warning sign M1 such as "warning" or a symbol mark and a message M2 including sentences such as "The number of uses has exceeded the upper limit. This grip cannot be used," may be displayed on the display screen 201a of the display unit 201. In addition to such sentences, a message that suggests maintenance such as "Please replace the spring," may be included in the message M2.

When the number of uses of the spring 2 has exceeded the upper limit, there is a high possibility of the spring property of the spring 2 being further degraded than a design value. Even when the force magnitude adjusting unit 213A is driven based on the adjustment information that is previously set to the force magnitude calculation unit 431, there is a possibility of failing to obtain the desired manipulation resistance.

In this case, to avoid the problem, it is necessary to replace the spring 2 or to change the adjustment information set to the force magnitude calculation unit 431. Therefore, in the present seventh modified example of the first embodiment of the present invention, when the number of uses has exceeded the upper limit, the operation of the manipulation input device is brought to an error end. Thereby, the manipulation input device 104 can be avoided from being used in a poor adjustment state.

The operator Op sees the warning sign, stops the use, and if necessary, may take measures, for instance, to replace the spring 2 or to change the adjustment information set to the force magnitude calculation unit 431.

In step S33, the force magnitude calculation unit 441 calculates a forward/backward movement amount of the force magnitude adjusting unit 213A which can obtain the desired manipulation resistance based on the preset adjustment information, and sends a driving signal corresponding to the forward/backward movement amount to the force magnitude adjusting unit 213A. Thereby, the force magnitude adjusting unit 213A moves forward or backward, and thus the length of the spring 2 is adjusted based on the adjustment information.

Next, in step S34, the force magnitude calculation unit 441 sends a control signal to update a counter to the counter 443. Thereby, the counter 443 updates the number of uses.

In this way, the initial setting operation of adjusting the manipulation resistance is terminated.

According to the present seventh modified example of the first embodiment of the present invention, prior to the automatic adjustment of the manipulation resistance, the number of uses of the master grip 213 is determined. For this reason, when there is a possibility that the number of uses has exceeded the upper limit, the spring property of the spring 2 is degraded, and the manipulation resistance cannot be adjusted, the warning sign is made without performing the adjustment. As a result, the problem that the sense of manipulation is changed by the degradation of the spring property can be prevented in advance.

In the description of the present seventh modified example of the first embodiment of the present invention, the adjustment information of the manipulation resistance has been described as being previously set to the force magnitude calculation unit 441. However, the input unit on which the operator Op carries out an input may be provided. In this case, the operator Op inputs the adjustment information of the manipulation resistance to the force magnitude calculation unit 441. Thereby, the adjustment information of the manipulation resistance can be changed.

Eighth Modified Example

Next, an eighth modified example of the first present embodiment of the present invention will be described.

Figure 19:
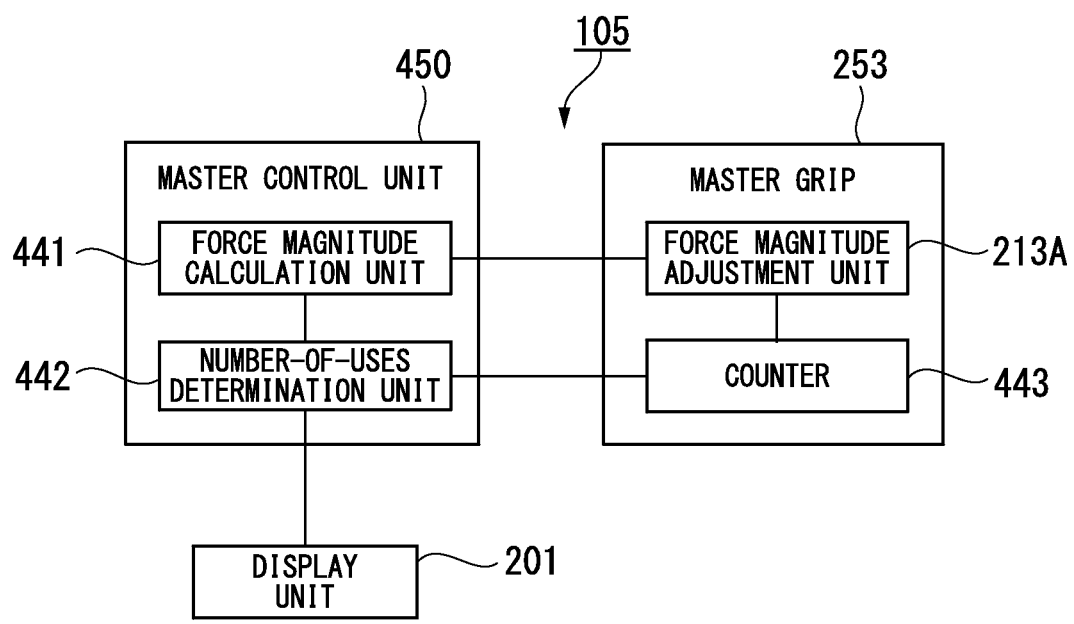
FIG. 19 is a functional block diagram showing a configuration of a manipulation input device according to an eighth modified example of the first embodiment of the present invention.

FIG. 19 is a functional block diagram showing a functional configuration of main parts in a manipulation input device according to the eighth modified example of the first embodiment of the present invention.

As shown in FIG. 19, the manipulation input device 105 of the present eighth modified example includes a master grip (manipulation unit) 253 and a master control unit (manipulation input control unit) 450 in place of the master grip 213 and the master control unit 440 of the manipulation input device 104 of the seventh modified example.

Like the manipulation input device 104, the manipulation input device 105 of the present modified example may be used as the manipulation input device in the master-slave manipulator 500.

The following description will focus on differences from the seventh modified example.

The master grip 253 is configured with a counter 443 added to the master grip 213 of the seventh modified example. As in the seventh modified example, the counter 443 is coupled to be able to communicate with a number-of-uses determination unit 442 of a master control unit 450.

The master control unit 450 is configured with the counter 443 of the master control unit 440 of the seventh modified example removed.

That is, the present eighth modified example of the first embodiment of the present invention is different from the seventh modified example in that the counter 443 is provided on a side of the master grip 253.

For this reason, according to the present eighth modified example of the first embodiment of the present invention, just like the seventh modified example, prior to automatic adjustment of manipulation resistance, the number of uses of the master grip 253 can be determined. For this reason, when there is a possibility that the spring property of the spring 2 is degraded and thus the manipulation resistance cannot be adjusted, a warning sign is made without performing the adjustment. As a result, the problem that the sense of manipulation is changed by the degradation of the spring property can be avoided in advance.

Further, according to the present eighth modified example of the first embodiment of the present invention, the counter 443 is installed on the master grip 253. As in the fifth modified example of the first embodiment of the present invention, even when the master grip 253 is detachably installed on the arm distal end 202*a*, a unique number of uses of the master grip 253 can be more reliably maintained. Further, in this case, a plurality of counters corresponding to a plurality of master grips 253 having a possibility of replacement need not be provided for the master control unit 450. As such, a configuration of the master control unit 450 can be simplified, compared to that of the seventh modified example.

Ninth Modified Example

Next, a ninth modified example of the present first embodiment will be described.

Figure 20:
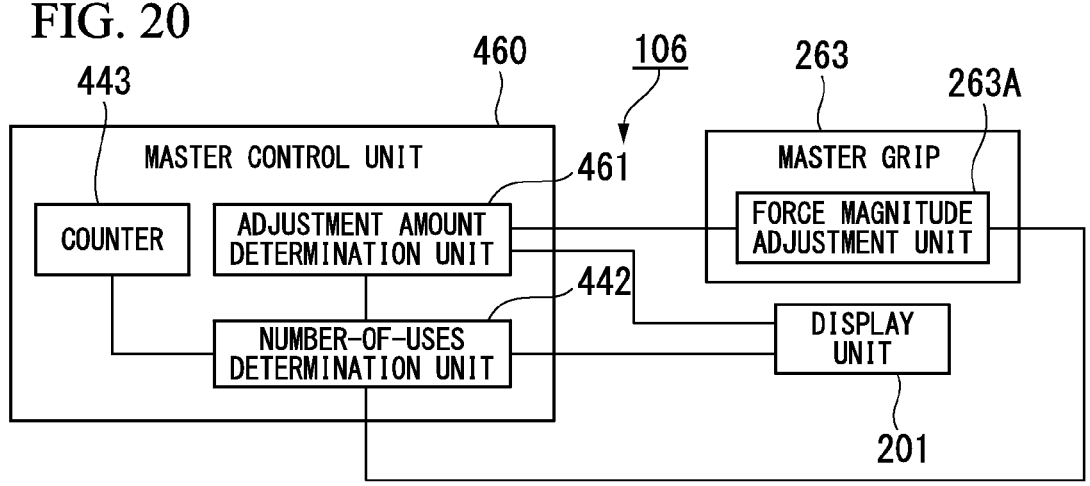
FIG. 20 is a functional block diagram showing a configuration of a manipulation input device according to a ninth modified example of the first embodiment of the present invention.

FIG. 20 is a functional block diagram showing a functional configuration of main parts in a manipulation input device according to the ninth modified example of the first embodiment of the present invention.

As shown in FIG. 20, the manipulation input device 106 of the present ninth modified example includes a master grip (manipulation unit) 263 and a master control unit (manipulation input control unit or adjustment target setting means) 460 in place of the master grip 213 and the master control unit 440 of the manipulation input device 104 of the seventh modified example.

Like the manipulation input device 104, the manipulation input device 106 of the present modified example may be used as the manipulation input device in the master-slave manipulator 500.

The following description will focus on differences from the seventh modified example.

The master grip 263 includes a force magnitude adjusting unit 263A in place of the force magnitude adjusting unit 213A of the master grip 213 of the seventh modified example.

The force magnitude adjusting unit 263A is configured to be manually adjusted via an actuator by an operator Op, and for instance, a configuration similar to that of the master grip of each of the first to third modified examples may be appropriately adopted thereas.

Hereinafter, as an example, a case in which the force magnitude adjusting unit 263A is configured of an actuator 33*b* and an adjustment input unit 33*c* similar to those of the third modified example and is manually adjusted using the adjustment input unit 33*c* by the operator Op will be described (see FIG. 8).

However, in the force magnitude adjusting unit 263A, the adjustment input unit 33*c* is electrically connected with the master control unit 460, and an adjustment operation is enabled by the operator Op only while an adjustment enable signal is input from the master control unit 460.

As shown in FIG. 20, the master control unit 460 includes an adjustment amount determination unit 461 in place of the force magnitude calculation unit 441 of the master control unit 440 of the seventh modified example.

The adjustment amount determination unit 461 is electrically connected to the force magnitude adjusting unit 263A, a display unit 201, a number-of-uses determination unit 442, and a counter 443, acquires a forward/backward movement amount from the force magnitude adjusting unit 263A, determines whether or not the forward/backward movement amount is identical to an adjustment value of preset manipulation resistance, and displays a result of the determination on the display unit 201. In the present ninth modified example, the display unit 201 configures an adjustment detection unit that informs of whether or not a reference force magnitude value is identical to an adjustment target value.

Further, the number-of-uses determination unit 442 of the present ninth modified example of the first embodiment of the present invention is electrically connected to the display unit 201 and the force magnitude adjusting unit 263A. The number-of-uses determination unit 442 is configured to send an enable or disable signal of adjustment of the force magnitude adjusting unit 263A according to a result of determining the number of uses.

Next, an operation of the present ninth modified example of the first embodiment of the present invention will be described.

Figure 21:
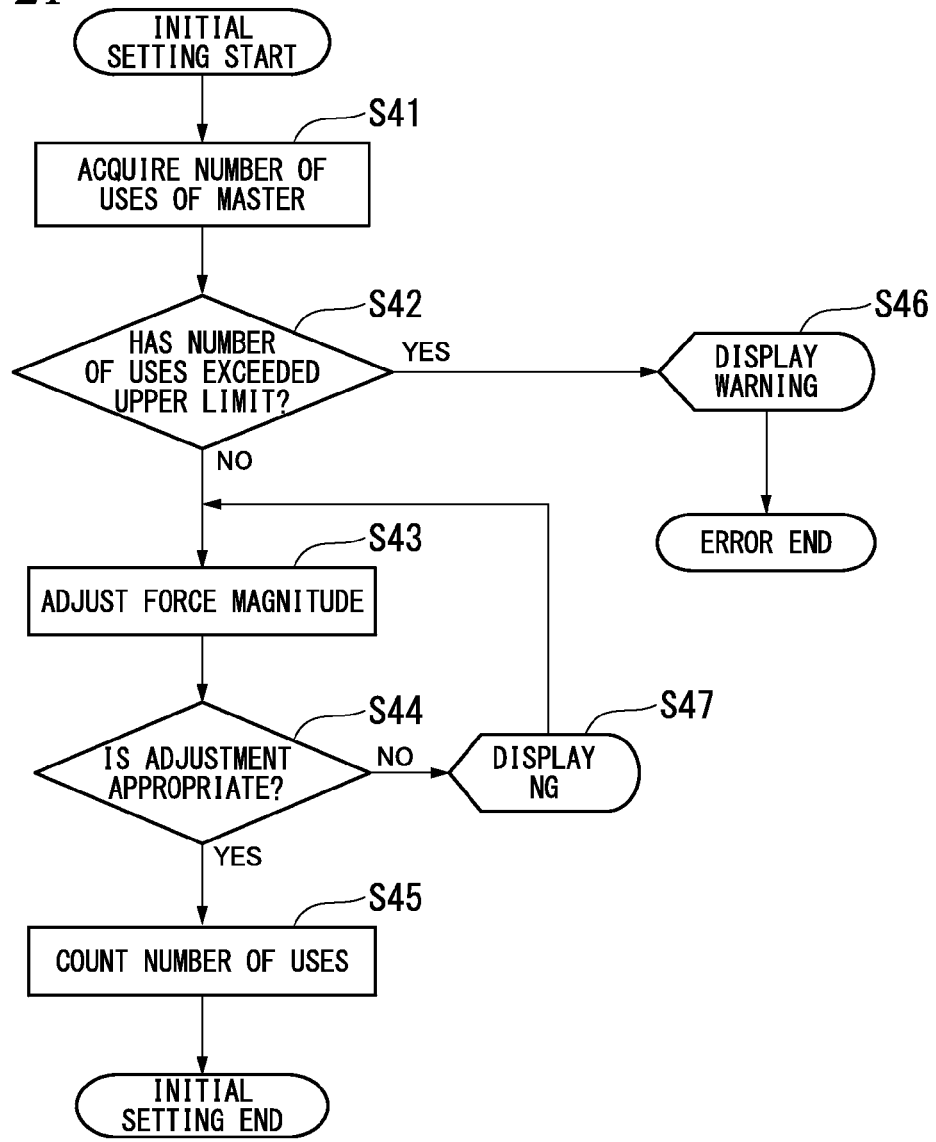
FIG. 21 is a flowchart for describing an operation of the manipulation input device according to the ninth modified example of the first embodiment of the present invention.
Figure 22A:
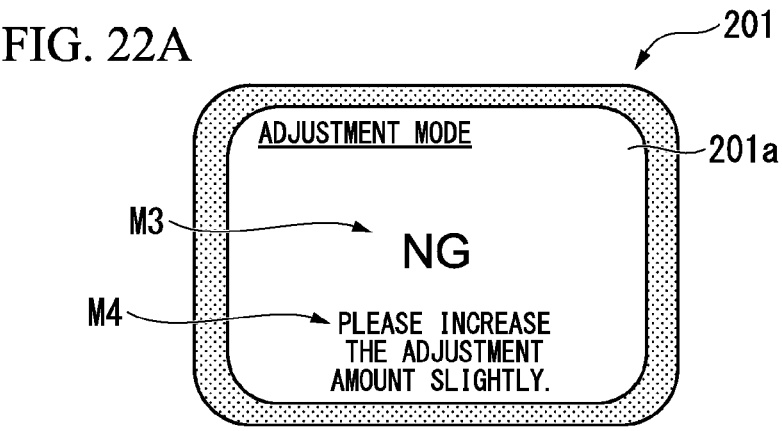
FIG. 22A is a schematic view showing an example of a display screen for an adjustment mode of the manipulation input device according to the ninth modified example of the first embodiment of the present invention.
Figure 22B:
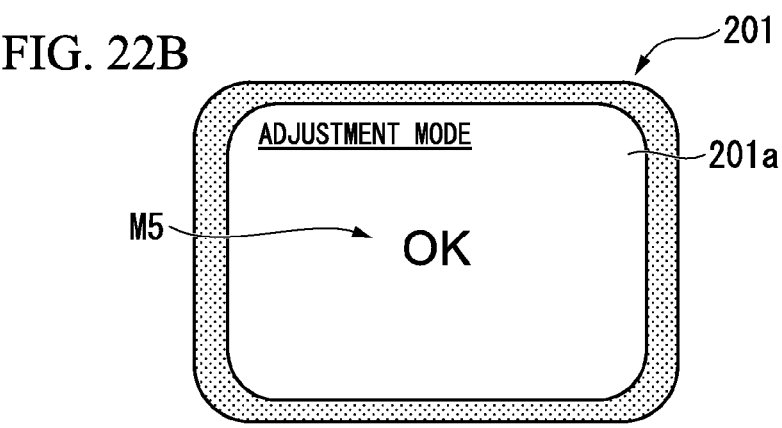
FIG. 22B is a schematic view showing an example of a display screen for an adjustment mode of the manipulation input device according to the ninth modified example of the first embodiment of the present invention.

FIG. 21 is a flowchart for describing an operation of the manipulation input device according to the ninth modified example of the first embodiment of the present invention. FIGS. 22A and 22B are schematic views showing an example of a display screen for an adjustment mode of the manipulation input device according to the ninth modified example of the first embodiment of the present invention.

The present ninth modified example of the first embodiment of the present invention is an example in which, in an initial setting operation when the manipulation input device 106 begins to be used, similar to the seventh modified example, the master control unit 460 automatically determines whether or not the number of uses of the master grip 263 has exceeded the upper limit according to the flowchart shown in FIG. 21, and enables the adjustment operation of the manipulation resistance only when the number of uses is less than the upper limit.

In the event of the initial setting start, the disable signal of the adjustment is sent to the force magnitude adjusting unit 263A by the number-of-uses determination unit 442.

First, in step S41, the number-of-uses determination unit 442 acquires information about the number of uses of the master grip 263 from the counter 443.

In next step S42, the number-of-uses determination unit 442 compares the acquired information of the number of uses and the upper limit of the number of uses stored previously.

When the number of uses has exceeded the upper limit, the number-of-uses determination unit 442 does not send the enable signal of the adjustment of the manipulation resistance to the force magnitude adjusting unit 263A, and proceeds to step S46.

When the number of uses has not exceeded the upper limit, the number-of-uses determination unit 442 sends the enable signal permitting the adjustment of the manipulation resistance to the force magnitude adjusting unit 263A, and proceeds to step S43. In this case, a message indicating that the manipulation resistance is adjustable may be displayed on the display unit 201 so that the operator Op immediately recognizes that the manipulation resistance becomes adjustable, or an appropriate tone may be played.

Step S46 is a process similar to step S35 of the seventh modified example. The number-of-uses determination unit 442 displays a warning signal as shown in FIG. 18 on the display unit 201, and then brings the operation of the manipulation input device 106 to an error end.

In step S43, the operator Op begins to adjust the manipulation resistance, for instance, using the adjustment input unit 33c. In this case, the adjustment amount determination unit 461 acquires a forward/backward movement amount of the actuator 33b of the force magnitude adjusting unit 263A.

Next, in step S44, the adjustment amount determination unit 461 determines whether or not the adjustment is appropriate. That is, the adjustment amount determination unit 461 refers to the pre-stored adjustment information to determine whether or not the forward/backward movement amount acquired from the force magnitude adjusting unit 263A is a forward/backward movement amount that can obtain desired manipulation resistance.

When the forward/backward movement amount fails to reach the forward/backward movement amount based on the adjustment information, the adjustment amount determination unit 461 determines that the adjustment is not appropriate, and proceeds to step S47.

When the forward/backward movement amount reaches the forward/backward movement amount based on the adjustment information, the adjustment amount determination unit 461 determines that the adjustment is appropriate, and proceeds to step S45.

In step S47, as shown in FIG. 22A, the adjustment amount determination unit 461 displays an "adjustment mode" on the display screen 201a of the display unit 201 so as to indicate entry into the adjustment mode, and furthermore displays an adjustment state sign M3 based on a letter such as "NG" or a symbol mark and a message M4 based including a sentence such as "Please increase the adjustment amount slightly."

Then, the process proceeds to step S43, and steps S43 and S44 are repeated similar to the aforementioned description.

In step S45, as shown in FIG. 22B, the adjustment amount determination unit 461 displays an adjustment state sign M5 based on, for instance, text such as "OK" or a symbol mark on the display screen 201a of the display unit 201.

Further, the adjustment amount determination unit 461 sends the disable signal of the adjustment to the force magnitude adjusting unit 263A so as to prevent an adjustment state from being accidentally changed.

Furthermore, the adjustment amount determination unit 461 sends a control signal for updating a counter to the counter 443. Thereby, the counter 443 updates the number of uses.

In this way, the initial setting operation adjusting the manipulation resistance is terminated.

According to the present ninth modified example of the first embodiment of the present invention, prior to the manual adjustment of the manipulation resistance, the number of uses of the master grip 263 is determined, like the seventh modified example. For this reason, when there is a possibility that the spring property of the spring 2 is degraded due to the number of uses exceeding the upper limit, and thus the manipulation resistance cannot be adjusted, a warning sign is made without performing the adjustment. As a result, the problem that the sense of manipulation is changed by the degradation of the spring property can be prevented in advance.

Further, in the present ninth modified example of the first embodiment of the present invention, a sign such as whether or not the adjustment of the manipulation resistance is appropriate is displayed on the display unit 201 during the adjustment. For this reason, even when the operator Op does not know a desired adjustment amount, the operator Op can view the sign of the display unit 201 to perform proper correction.

In the description of the present ninth modified example of the first embodiment of the present invention, the adjustment information of the manipulation resistance has been described as being previously set to the adjustment amount determination unit 461. However, as in the seventh modified example, the adjustment information may be configured to be able to be input by the operator Op.

Tenth Modified Example

Next, a tenth modified example of the present first embodiment of the present invention will be described.

Figure 23:
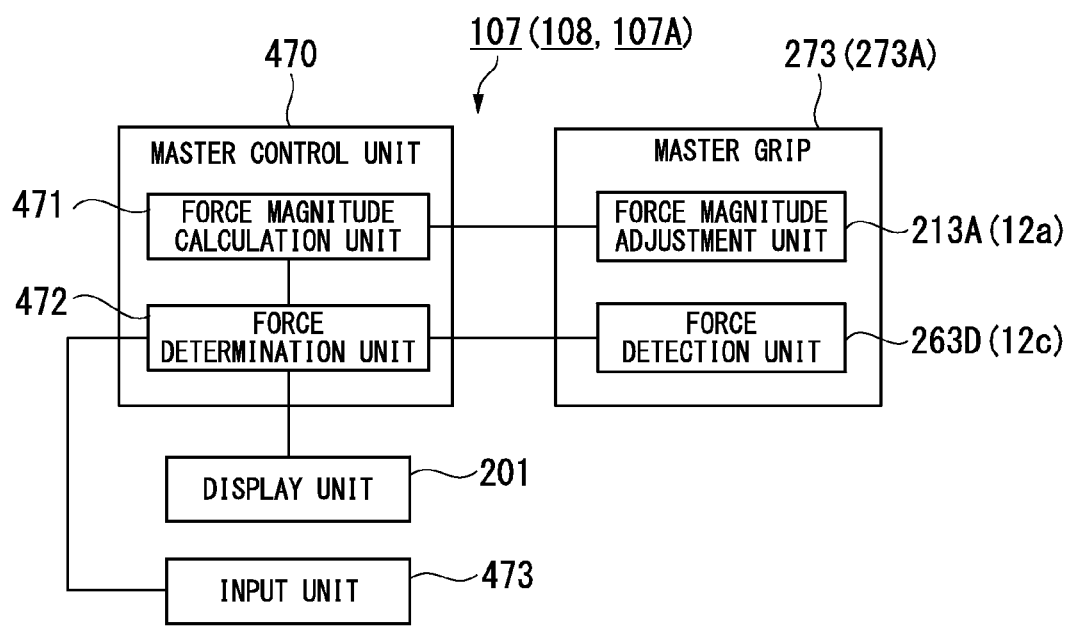
FIG. 23 is a functional block diagram showing a configuration of a manipulation input device according to a tenth modified example of the first embodiment of the present invention.

FIG. 23 is a functional block diagram showing a functional configuration of main parts in a manipulation input device according to the tenth modified example of the first embodiment of the present invention.

As shown in FIG. 23, the manipulation input device 107 of the present tenth modified example of the first embodiment of the present invention includes a master grip (manipulation unit) 273 and a master control unit (manipulation input control unit) 470 in place of the master grip 1 and the master control unit 401 of the manipulation input device 100 of the first embodiment of the present invention.

Like the manipulation input device 100, the manipulation input device 107 of the present tenth modified example of the first embodiment of the present invention may be used as the manipulation input device in the master-slave manipulator 500.

The following description will focus on differences from the first embodiment.

The master grip 273 is configured with a force detection unit 273D added to the master grip 213 of the fourth modified example.

The force detection unit 273D detects a reaction force acting on the force magnitude adjusting unit 213A from the spring 2, and sends information about its detection value to the master control unit 470.

A detailed configuration of the force detection unit 273D is not particularly limited as long as the reaction force of the spring 2 can be detected. For example, a configuration in which a load of the actuator provided to the force magnitude adjusting unit 213A is detected and converted into a force magnitude may be adopted. Further, a sensor for force detection may be adopted.

The master control unit 470 includes a force magnitude calculation unit 471 in place of the force magnitude calculation unit 411 of the master control unit 410 of the fourth modified example, and is configured with a force determination unit 472 added.

When the adjustment of the manipulation resistance is permitted by the force determination unit 472 to be described below, the force magnitude calculation unit 471 calculates a forward/backward movement amount of the force magnitude adjusting unit 213A which can obtain desired manipulation resistance based on preset adjustment information or a force magnitude sent from the force determination unit 472, and sends a driving signal corresponding to the forward/backward movement amount to the force magnitude adjusting unit 213A.

The force determination unit 472 communicates with the force detection unit 273D, acquires the reaction force of the spring 2 from the force detection unit 273D, and determines whether or not a detection value of the reaction force of the spring 2 is within a preset adjustable range.

When the detection value is beyond the adjustable range, the force determination unit 472 displays a warning sign warning that the force magnitude adjusting unit 213A is not within the adjustable range on the display unit 201, and then brings the operation of the manipulation input device 106 to an error end.

As the warning sign, for example, instead of the message M2 of FIG. 18, a message such as "Since the spring is degraded, the adjustment is impossible. Please replace the spring," is displayed.

When the detection value is within the adjustable range, the force determination unit 472 sends a control signal to begin the adjustment of the manipulation resistance to the force magnitude calculation unit 471.

Here, the adjustable range of the spring 2 is stored in the force determination unit 472 in advance as an amount of allowable deviation from a relation between the length and the reaction force of the spring 2 in view of design.

Further, in the present tenth modified example of the first embodiment of the present invention, the input unit 473 is connected so that the operator Op can directly input the reaction force of the spring 2 or an adjustment amount corresponding to the reaction force according to his/her preference. A configuration similar to the adjustment input unit 13c of the first modified example of the present invention may be adopted for the input unit 473.

When the adjustment amount is changed via the input unit 473, the force determination unit 472 calculates whether or not the changed adjustment amount can be adjusted, and performs determination similar to the aforementioned description.

Next, an operation of the present tenth modified example of the first embodiment of the present invention will be described.

Figure 24:
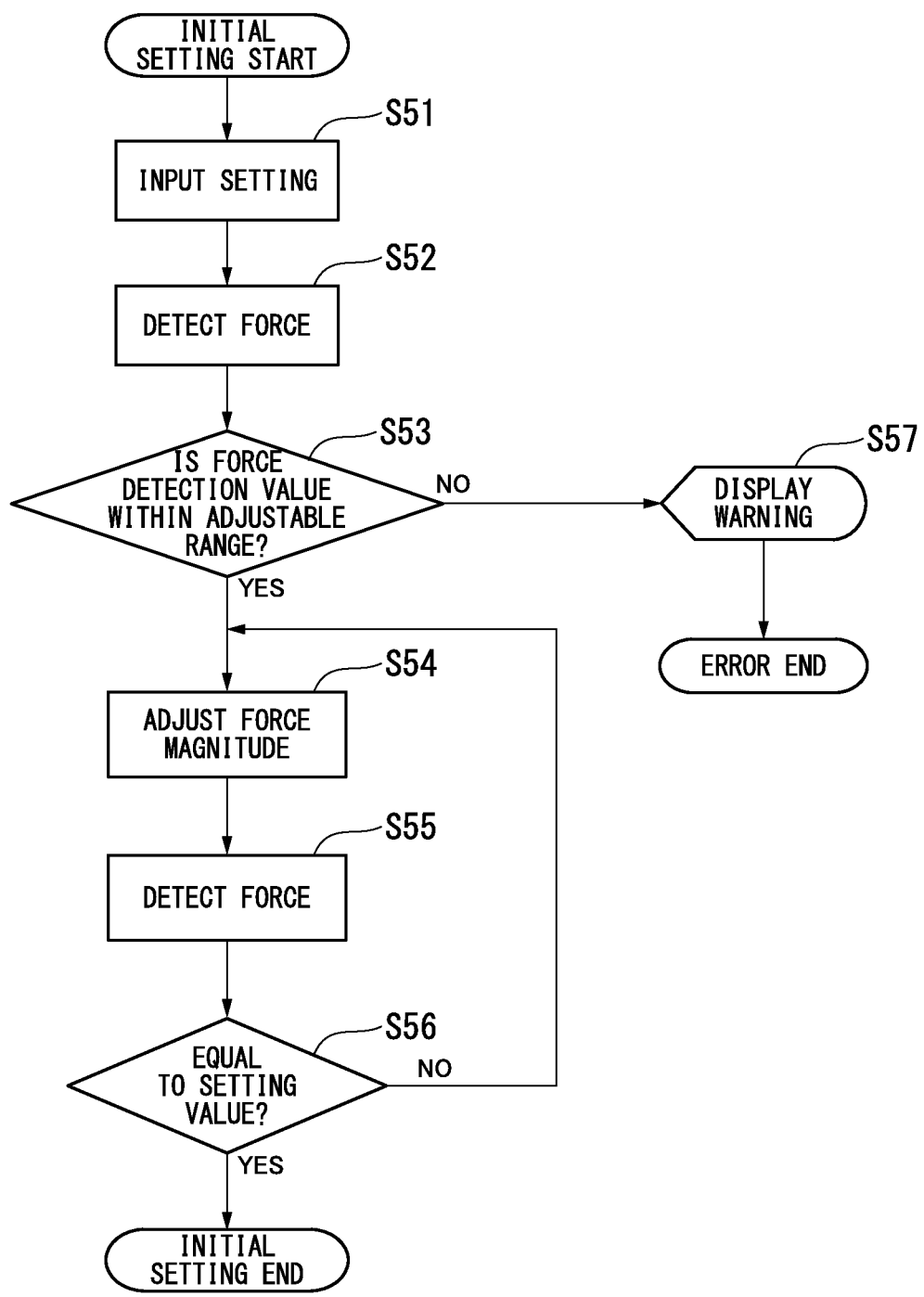
FIG. 24 is a flowchart for describing an operation of the manipulation input device according to the tenth modified example of the first embodiment of the present invention.

FIG. 24 is a flowchart for describing an operation of the manipulation input device according to the tenth modified example of the first embodiment of the present invention.

In the present tenth modified example of the first embodiment of the present invention, an adjustment operation of the manipulation resistance is automatically performed according to the flowchart shown in FIG. 24.

First, in step S51, input of the adjustment amount of the manipulation resistance by the input unit 473 is requested, and the operator Op carries out a proper input. When the manipulation resistance to which the operator Op gives a particular preference is not designated, a default value is configured to be able to be selected. The default value is an adjustment value pre-stored in the force determination unit 472.

Next, in step S52, the force determination unit 472 acquires a detection value (force detection value) of the reaction force of the spring 2 from the force detection unit 273D.

Subsequently, in step S53, the force determination unit 472 determines whether or not the acquired force detection value is within the adjustable range.

When the force detection value is not within the adjustable range, the process proceeds to step S57.

When the force detection value is within the adjustable range, the process proceeds to step S54.

In step S57, the force determination unit 472 displays a warning sign warning that the force detection value is not within the adjustable range on the display unit 201, and then brings the operation of the manipulation input device 106 to an error end.

The operator Op sees the warning sign, stops the use, and if necessary, may take measures, for instance, to replace the spring 2.

In step S54, the force magnitude calculation unit 441 calculates a forward/backward movement amount of the force magnitude adjusting unit 213A which can obtain desired manipulation resistance based on the adjustment information set according to step S51, and sends a driving signal corresponding to the forward/backward movement amount to the force magnitude adjusting unit 213A. Thereby, the force magnitude adjusting unit 213A moves forward or backward, and thus the length of the spring 2 is adjusted.

Next, in step S55, the force determination unit 472 acquires a force detection value from the force detection unit 273D.

Subsequently, in step S56, the force determination unit 472 determines whether or not the force detection value is equal to a setting value of a target detection value that is an adjustment target.

When the force detection value is different from the setting value, the process proceeds to step S54. An error between the force detection value and the setting value is sent to the force magnitude calculation unit 471.

In step S54, the force magnitude calculation unit 471 calculates a forward/backward movement amount for making the force detection value identical to the setting value based on information about the error of the setting value which is sent from the force determination unit 472, and sends a driving signal corresponding to the forward/backward movement amount to the force magnitude adjusting unit 213A. In this way, steps S54 to S56 are repeated.

Further, when the force detection value is equal to the setting value, the initial setting operation of adjusting the manipulation resistance is terminated.

According to the present tenth modified example of the first embodiment of the present invention, the force determination unit 472 determines whether or not the manipulation resistance of the master grip 273 is adjustable, and only when it is adjustable, can perform adjustment so as to be able to obtain the reaction force of the spring 2 which corresponds to the required manipulation resistance. For this reason, for instance, due to time-dependent degradation or flaws of the spring, adjustment to a manipulation resistance different from the target can be avoided.

Eleventh Modified Example

Next, an eleventh modified example of the present first embodiment of the present invention will be described.

Figure 25:
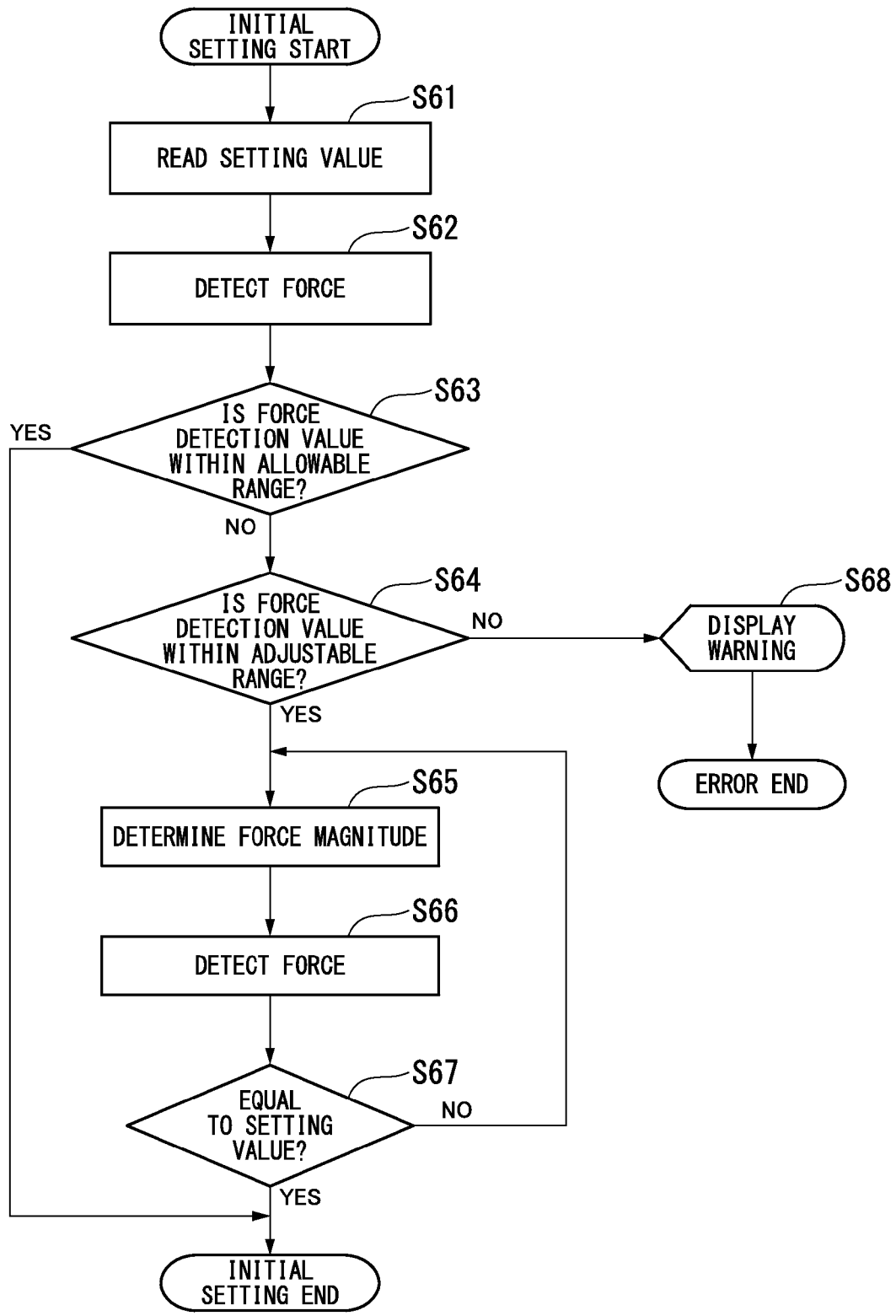
FIG. 25 is a flowchart for describing an adjustment operation of a manipulation input device according to an eleventh modified example of the first embodiment of the present invention.

FIG. 25 is a flowchart for describing an adjustment operation of a manipulation input device according to the eleventh modified example of the first embodiment of the present invention.

As shown in FIG. 23, the manipulation input device 108 of the present modified example has a device configuration similar to that of the manipulation input device 107 of the tenth modified example, and differs in an operation only. For this reason, like the manipulation input device 100, the manipulation input device 108 of the present eleventh modified example may be used as the manipulation input device in the master-slave manipulator 500.

The following description will focus on differences from the seventh modified example of the first embodiment of the present invention.

The manipulation input device 108 performs an automatic adjustment operation shown in FIG. 25 at all times, as needed, or at fixed periods in order to maintain a preset reaction force of the spring 2 during the operation of the master-slave manipulator 500.

The reaction force of the spring 2 to be adjusted is configured to be able to be changed by, for instance, an input of the operator Op from the input unit 473, as in the tenth modified example of the first embodiment of the present invention.

Hereinafter, however, only the adjustment operation which is a characteristic feature of the present modified example will be described. For this reason, a setting value of the reaction force of the spring 2 is described as being previously stored in the force determination unit 472.

First, in step S61, the force determination unit 472 reads the preset setting value of the reaction force of the spring 2.

Next, in step S62, the force determination unit 472 acquires a detection value of the reaction force (force detection value) of the spring 2 from the force detection unit 273D.

Subsequently, in step S63, the force determination unit 472 determines whether the acquired force detection value is within an allowable range.

When the force detection value is not within the allowable range, the process proceeds to step S64.

When the force detection value is within the allowable range, the adjustment operation is terminated. Thereby, even when the force detection value is different from the setting value, if a change in the sense of manipulation is such a difference as to become an allowable range, the adjustment is not performed. As such, current manipulation resistance is maintained.

Steps S64, S65, S66, S67 and S68 are similar to steps S53, S54, S55, S56, and S57 of the seventh modified example of the first embodiment of the present invention, respectively.

According to the present eleventh modified example of the first embodiment of the present invention, when a predetermined adjustment value of the manipulation resistance is set, the adjustment operation of the manipulation resistance of the master grip 273 is automatically performed by the force determination unit 472 only when the force detection value of the master grip 273 is not within the allowable range and the force detection value is within the adjustable range.

For this reason, the reaction force of the spring 2 is detected, and the automatic adjustment is performed so that the reaction force of the spring 2 corresponds to predetermined manipulation resistance until the spring property of the spring 2 is degraded to an unadjustable extent. As a result, even when time-dependent degradation of the spring property occurs, an almost constant sense of manipulation is maintained.

Twelfth Modified Example

Next, a twelfth modified example of the present first embodiment of the present invention will be described.

Figure 26:
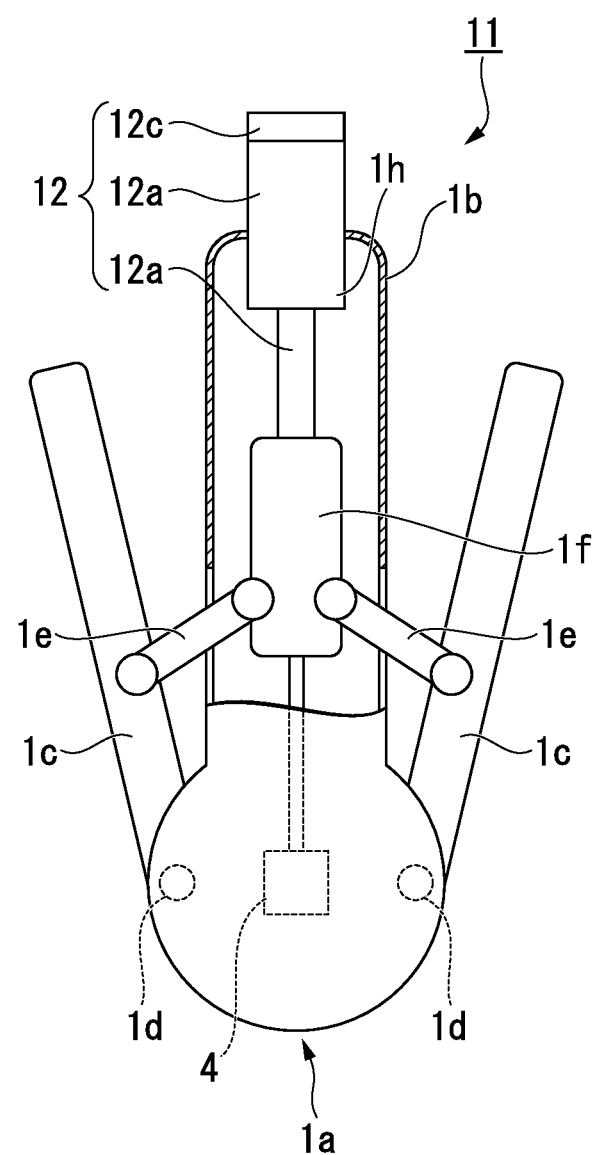
FIG. 26 is a schematic partial cross-sectional view showing a configuration of main parts in a manipulation input device according to a twelfth modified example of the first embodiment of the present invention.

FIG. 26 is a schematic partial cross-sectional view showing a configuration of main parts in a manipulation input device according to the twelfth modified example of the first embodiment of the present invention.

As shown in FIG. 23, the manipulation input device 107A of the present twelfth modified example of the first embodiment of the present invention includes a master grip (manipulation unit) 273A in place of the master grip 273 of the manipulation input device 107 of the tenth modified example.

As shown in FIG. 26, the master grip 273A includes a resistance generating actuator (manipulation resistance generator) 12 for generating resistance in place of the spring 2 and the actuator 13b of the master grip 11 of the first modified example of the first embodiment, and is configured with the adjustment input unit 13c removed.

Like the manipulation input device 100 of the first embodiment, the manipulation input device 107A of the present twelfth modified example of the first embodiment of the present invention may be used as the manipulation input device in the master-slave manipulator 500.

The following description will focus on differences from the first and tenth modified examples.

The resistance generating actuator 12 is a linear actuator whose entire length is changed. The resistance generating actuator 12 includes a pressing shaft 12b that is engaged on a distal end of a displacement shaft 1*f* and applies a resistance force when displaced toward a distal end side of the displacement shaft 1*f*, a force magnitude adjusting unit 12*a* that adjusts a force magnitude of the resistance force of the pressing shaft 12*b*, and a force detection unit 12*c* that detects the magnitude of the resistance force of the pressing shaft 12*b*.

An appropriate configuration may be adopted as the configuration of the resistance generating actuator 12 as long as it can generate a resistance force corresponding to an amount of change of the entire length caused by the displacement of the displacement shaft 1*f*. For example, an electrically driven actuator or a hydraulically driven actuator may be adopted.

In the present twelfth modified example of the first embodiment of the present invention, for example, the resistance force magnitude of the resistance generating actuator 12 when an opening/closing angle of each manipulation handle 1*c* is set to an appropriate reference value such as a maximum opening/closing angle or a minimum opening/closing angle is detected by the force detection unit 12*c*, and the resistance force magnitude in this state can be adjusted by the force magnitude adjusting unit 12*a*. For this reason, just like the tenth modified example, the manipulation resistance in the master grip 273A can be adjusted.

Thirteenth Modified Example

Next, a thirteenth modified example of the present embodiment will be described.

Figure 27:
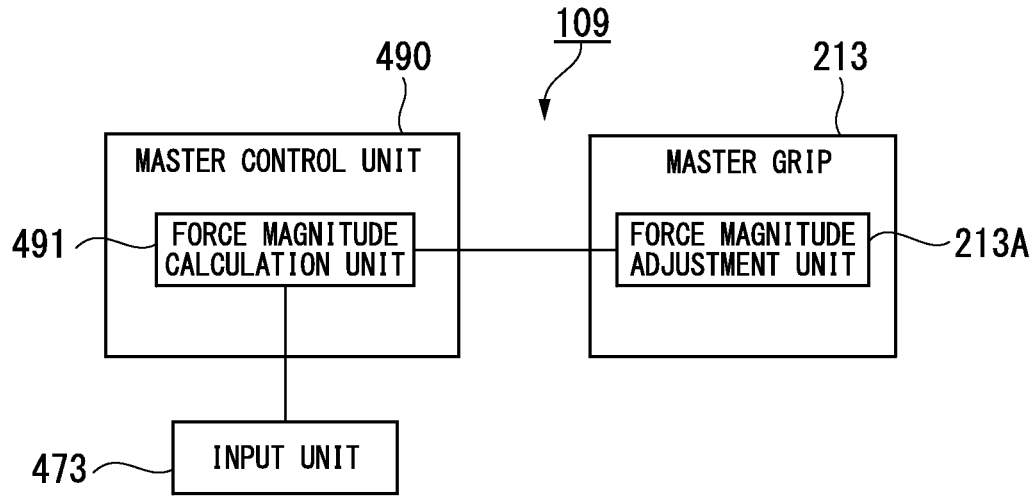
FIG. 27 is a functional block diagram showing a configuration of a manipulation input device according to a thirteenth modified example of the first embodiment of the present invention.

FIG. 27 is a functional block diagram showing a configuration of a manipulation input device according to the thirteenth modified example of the first embodiment of the present invention.

As shown in FIG. 27, the manipulation input device 109 of the present thirteenth modified example of the first embodiment of the present invention includes a master grip 213 and a master control unit (manipulation input control unit) 490 in place of the master grip 1 and the master control unit 401 of the manipulation input device 100 of the first embodiment.

Like the manipulation input device 100, the manipulation input device 109 of the present thirteenth modified example of the first embodiment of the present invention may be used as the manipulation input device in the master-slave manipulator 500.

The following description will focus on differences from the first embodiment.

The master control unit 490 includes a force magnitude calculation unit 491 in place of the force magnitude calculation unit 411 of the master control unit 410 of the fourth modified example. An input unit 473 similar to that of the tenth modified example is electrically connected to the force magnitude calculation unit 491.

The force magnitude calculation unit 491 calculates a forward/backward movement amount of a force magnitude adjusting unit 213A which can obtain desired manipulation resistance based on input information input from the input unit 473, and sends a driving signal corresponding to the forward/backward movement amount to the force magnitude adjusting unit 213A.

A table or a conversion formula that converts the input information, which can be previously input by the input unit 473, into the forward/backward movement amount to the force magnitude adjusting unit 213A is stored in the force magnitude calculation unit 491.

For this reason, the input information input to the input unit 473 may be the forward/backward movement amount itself. However, the input information may be any information other than the forward/backward movement amount. For example, a magnitude of the manipulation resistance may be associated with a plurality of level values, for instance, five steps of levels 1 to 5, from a minimum value to a maximum value. In this case, the operator Op can select the magnitude of the manipulation resistance from among the levels 1 to 5. Further, as the plurality of level values, for example, options indicating degrees defined as "weak," "normal," and "strong" may be adopted.

Further, the forward/backward movement amount previously customized according to the preference of each operator Op may be configured to be able to be selected and input from options of, for instance, "for operator A" and "for operator B."

Next, an operation of the present thirteenth modified example of the first embodiment of the present invention will be described.

Figure 28:
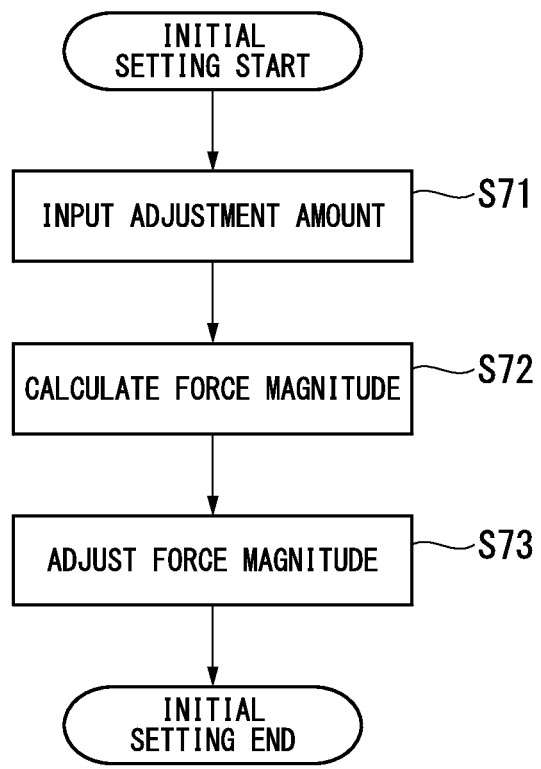
FIG. 28 is a flowchart for describing an operation of the manipulation input device according to the thirteenth modified example of the first embodiment of the present invention.

FIG. 28 is a flowchart for describing an adjustment operation of the manipulation input device according to the thirteenth modified example of the first embodiment of the present invention.

In the present thirteenth modified example of the first embodiment of the present invention, an initial adjustment operation is performed according to the flowchart shown in FIG. 28.

First, in step S71, input of an adjustment amount of the manipulation resistance is requested by the input unit 473, and the operator Op performs an appropriate input.

Next, in step S72, the force magnitude calculation unit 491 calculates a forward/backward movement amount of the force magnitude adjusting unit 213A which can obtain desired manipulation resistance based on the input information input according to step S71, and sends a driving signal corresponding to the forward/backward movement amount to the force magnitude adjusting unit 213A.

Subsequently, in step S73, the force magnitude adjusting unit 213A moves forward or backward in response to the driving signal, and thus the length of the spring 2 is adjusted.

In this way, the initial setting operation is terminated.

According to the present thirteenth modified example, the manipulation resistance is adjusted depending on the input information input by the input unit 473. For this reason, the manipulation resistance corresponding to the preference of the operator Op can be easily set.

Second Embodiment

A manipulation input device according to a second embodiment of the present invention will be described.

Figure 29A:
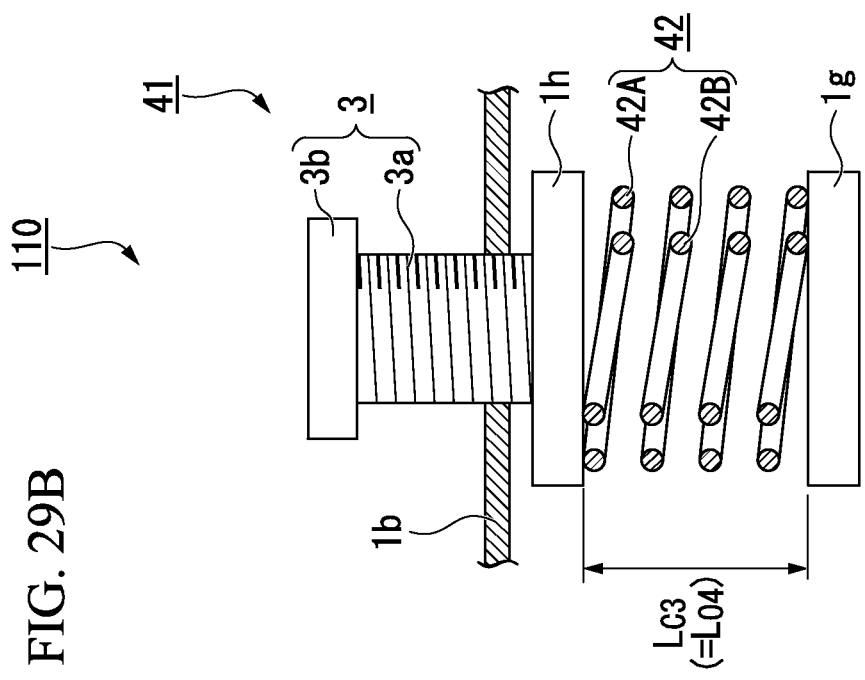
FIG. 29A is a schematic cross-sectional view showing a configuration and an operation of main parts in a manipulation input device according to a second embodiment of the present invention.
Figure 29B:
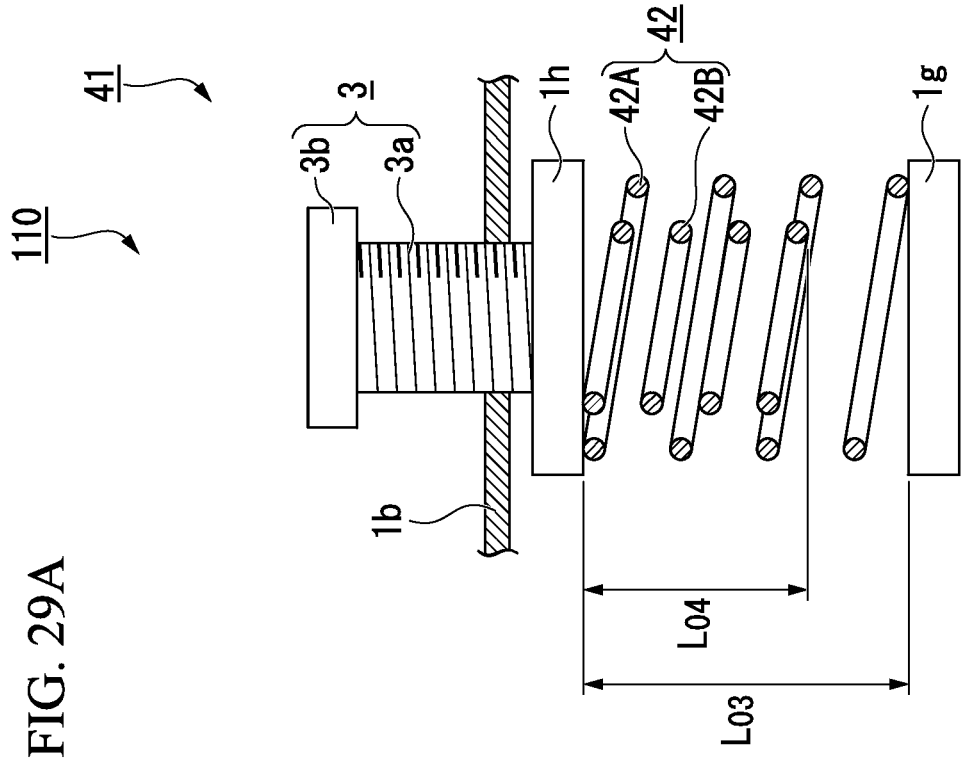
FIG. 29B is a schematic cross-sectional view showing a configuration and an operation of the main parts in the manipulation input device according to the second embodiment of the present invention.
Figure 30:
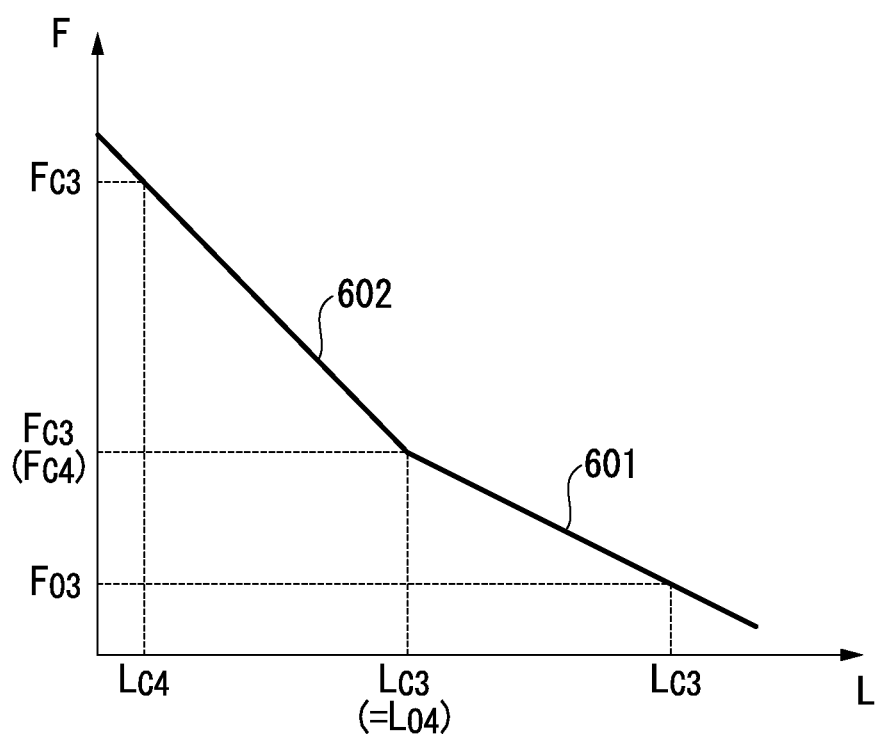
FIG. 30 is a graph showing an example of a change in manipulation resistance in the manipulation input device according to the second embodiment of the present invention.

FIGS. 29A and 29B are schematic cross-sectional views showing a configuration and an operation of main parts in a manipulation input device according to the second embodiment of the present invention. FIG. 30 is a graph showing an example of a change in manipulation resistance in the manipulation input device according to the second embodiment of the present invention. In FIG. 30, the horizontal axis indicates a length L of a spring, and the vertical axis indicates a spring force F.

The manipulation input device 110 of the present second embodiment includes a spring (manipulation resistance generator) 42 in place of the spring 2 of the master grip 1 in the manipulation input device 100 of the first embodiment, as shown in FIG. 29A by main parts.

The spring 42 includes first and second springs 42A and 42B having different lengths.

Like the manipulation input device 100, the manipulation input device 110 of the present second embodiment may be used as the manipulation input device in the master-slave manipulator 500.

The following description will focus on differences from the first embodiment.

The first spring 42A has a greater diameter than the second spring 42B, and is a compression coil spring whose natural length is longer than that $L_{O4}$ of the second spring 42B to be described below.

Opposite ends of the first spring 42A are fixed to a spring holding part 1h and a spring coupling part 1g. In an opened state of a master grip 41, when a force magnitude adjusting member 3a is located at a position maximally retracted to a distal end side (shown as an upper side) (see FIG. 29A), the length of the first spring 42A is $L_{O3}$ (where $L_{O3}>L_{O4}$).

The second spring 42B has a smaller diameter than the first spring 42A, and is a compression coil spring having a natural length $L_{O4}$.

Further, in a state in which the second spring 42B is inserted into the first spring 42A, one end of the second spring 42B is fixed to the spring holding part 1h.

Spring constants of the first and second springs 42A and 42B may be equal to or different from each other.

With the configuration, when a grip part 1a of the master grip 41 is closed, the first spring 42A is compressed, and thus the spring length becomes shorter than $L_{O3}$. In the present second embodiment the present invention, in the state in which the force magnitude adjusting member 3a is maximally retracted to the distal end side, when an opening/closing angle of the grip part 1a is minimum, the spring length of the first spring 42A is set to be $L_{C3}=L_{O4}$ (see FIG. 29B). Thus, in the opening/closing operation, the second spring 42B remains at the natural length.

Accordingly, in the opening/closing operation, the manipulation resistance is formed only by the spring force of the first spring 42A associated with the compression of the first spring 42A. That is, as shown by a straight line 601 of FIG. 30, as the length L of the spring is changed from $L_{O3}$ to $L_{C3}$, the spring force F is linearly increased from $F_{O3}$ to $F_{C3}$ depending on the spring constant of the first spring 42A.

In the present second embodiment, when greater manipulation resistance is required, as shown in FIGS. 31A and 31B, the force magnitude adjusting member 3a is advanced toward a proximal end side (shown as a lower side) by $\Delta_1=L_{O3}-L_{O4}$. Thereby, the second spring 42B is in contact with the spring coupling part 1g.

When the grip part 1a is closed from the state to minimize the opening/closing angle, the spring coupling part 1g is displaced to the distal end, and as shown in FIG. 31B, the spring lengths of the first and second springs 42A and 42B become $L_{C4}$ (where $L_{C4}<L_{O4}$). Thus, in this opening/closing operation, the first and second springs 42A and 42B become the same spring length and are compressed.

Accordingly, in the opening/closing operation, the manipulation resistance is formed by the sum of the spring forces associated with the compression of the first and second springs 42A and 42B. That is, as shown in a straight line 602 of FIG. 30, as the length L of the spring is changed from $L_{O4}$ to $L_{C4}$, the spring force F is linearly increased from $F_{O4}$ to $F_{C4}$ depending on the sum of the spring constants of the first and second springs 42A and 42B.

In this manner, in the present second embodiment, a forward/backward movement amount of the force magnitude adjusting unit 3 is adjusted. Thereby, the magnitude of the spring constant, that is, a spring property, of the manipulation resistance generator, i.e. a change rate characteristic of the force magnitude of the manipulation resistance, can be changed. Thereby, the manipulation resistance can be adjusted as needed.

Further, in the above description, the case in which an almost maximum region on the straight lines 601 and 602 of FIG. 30 is assigned to an entire range of the opening/closing angle is given as an example. However, the magnitude of $\Delta_1$ may be appropriately changed. Thereby, similar to the first embodiment, the range of the force magnitude used is changed on each of the straight lines 601 and 602, and thus the manipulation resistance can also be changed.

Fourteenth Modified Example

A manipulation input device according to a fourteenth modified example of the second embodiment of the present invention will be described.

Figure 32A:
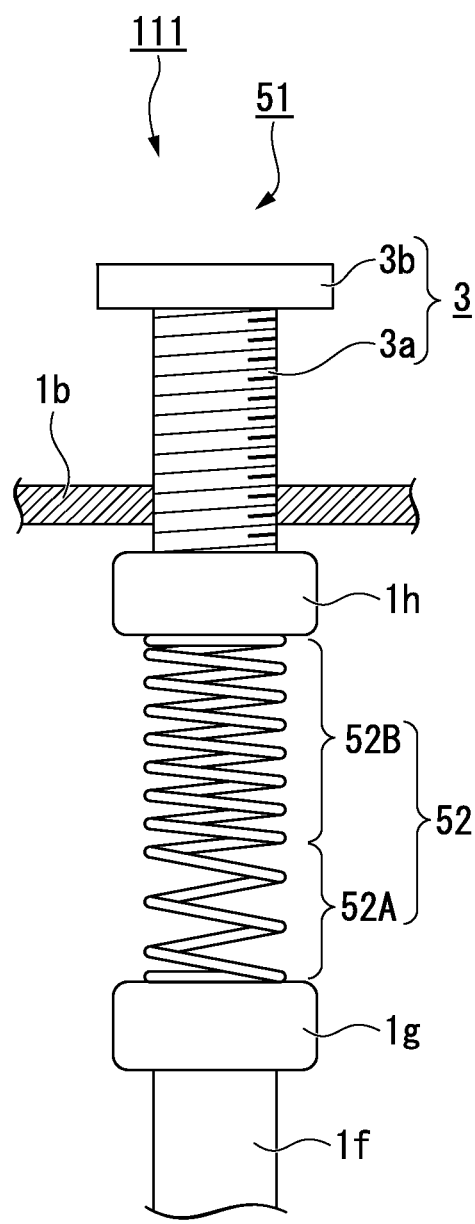
FIG. 32A is a schematic cross-sectional view showing a configuration and an operation of main parts in a manipulation input device according to a fourteenth modified example of the second embodiment of the present invention.
Figure 32B:
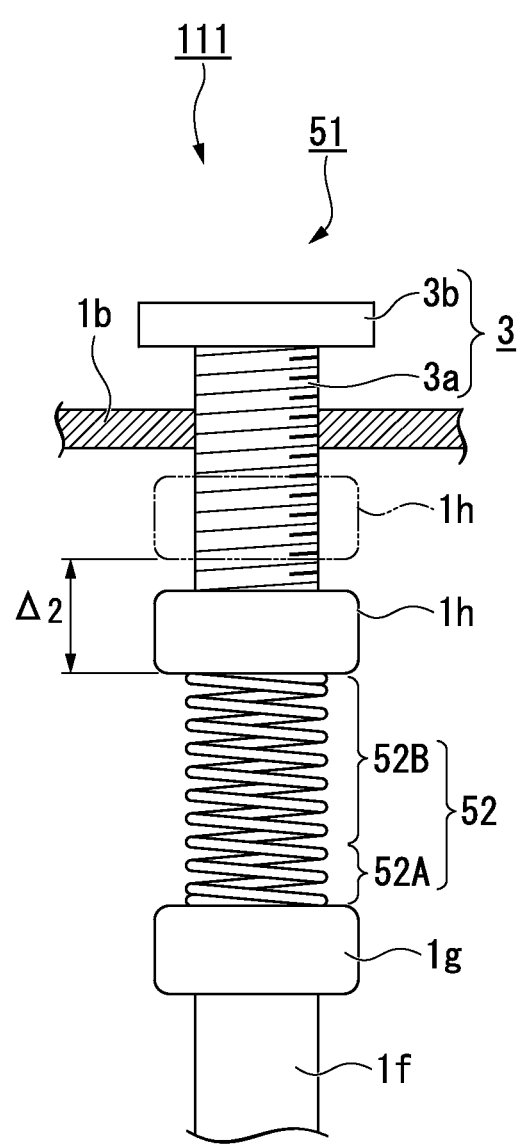
FIG. 32B is a schematic cross-sectional view showing a configuration and an operation of main parts in a manipulation input device according to the fourteenth modified example of the second embodiment of the present invention.

FIGS. 32A and 32B are schematic cross-sectional views showing a configuration and an operation of main parts in a manipulation input device according to the fourteenth modified example of the second embodiment of the present invention.

The manipulation input device 111 of the present modified example includes a spring (manipulation resistance generator or elastic member) 52 in place of the spring 2 of the master grip 1 in the manipulation input device 100 of the first embodiment, as shown in FIG. 32A by main parts.

Like the manipulation input device 100, the manipulation input device 111 of the present fourteenth modified example of the second embodiment of the present invention may be used as the manipulation input device in the master-slave manipulator 500.

The following description will focus on differences from the first embodiment.

The spring 52 is a compression coil spring in which a low elasticity spring portion 52A having a low spring constant compared to a high elasticity spring portion 52B and the high elasticity spring portion 52B having a high spring constant compared to the low elasticity spring portion 52A by, for instance, treatment of changing a winding density are adjacently installed in an axial direction thereof. That is, the spring 52 is an elastic member as if two springs having different spring constants are coupled in series.

In the present fourteenth modified example of the second embodiment of the present invention, the low elasticity spring portion 52A is fixed to a spring coupling part 1g, and the high elasticity spring portion 52B is fixed to a spring holding part 1h.

With the configuration, when a grip part 1a of a master grip 41 is closed, the low elasticity spring portion 52A and the high elasticity spring portion 52B are compressed by a common compressive force. While the low elasticity spring portion 52A can be compressed, a compression amount of the high elasticity spring portion 52B is small, and a spring force nearly based on a compression amount of the low elasticity spring portion 52A is predominant. For this reason, the change rate characteristic of the force magnitude becomes a straight line having a slope similar to the spring constant of the low elasticity spring portion 52A.

Accordingly, to reduce the manipulation resistance, as shown in FIG. 32A, the force magnitude adjusting member 3a is kept retracted to the distal end side (shown upper side), and a spring length of the spring 52 is kept increased.

On the other hand, when the compressive force applied to the spring 52 is increased, the compression amount of the low elasticity spring portion 52A reaches a limit. In this case, since only the high elasticity spring portion 52B of the spring 52 can behave as an elastic member, the spring force caused by the spring 52 is changed along a straight line having a slope equal to the spring constant of the high elasticity spring portion 52B.

For this reason, a relation between the spring length of the spring 52 and the force magnitude is represented by a graph that is almost similar to a graph having a broken line shape as shown in the graph of FIG. 30.

According to the configuration, to generate greater manipulation resistance at the same opening/closing angle, as shown in FIG. 32B, the force magnitude adjusting member 3a is advanced toward the proximal end side (shown as a lower side) by $\Delta_2$. $\Delta_2$ is, for instance, a compression amount required to almost fully compress the low elasticity spring portion 52A.

When the grip part 1a is closed from this state, the manipulation resistance is almost generated by the high elasticity spring portion 52B having the high spring constant. As such, the manipulation resistance can be increased.

In this manner, in the present fourteenth modified example of the second embodiment of the present invention, like the second embodiment, a forward/backward movement amount of the force magnitude adjusting unit 3 is adjusted. Thereby, the magnitude of the spring constant, that is, the spring property of the manipulation resistance generator, i.e. the change rate characteristic of the force magnitude of the manipulation resistance, can be changed. Thereby, the manipulation resistance can be adjusted as needed.

Fifteenth Modified Example

A manipulation input device according to another fifteenth modified example of the second embodiment of the present invention will be described.

Figure 33A:
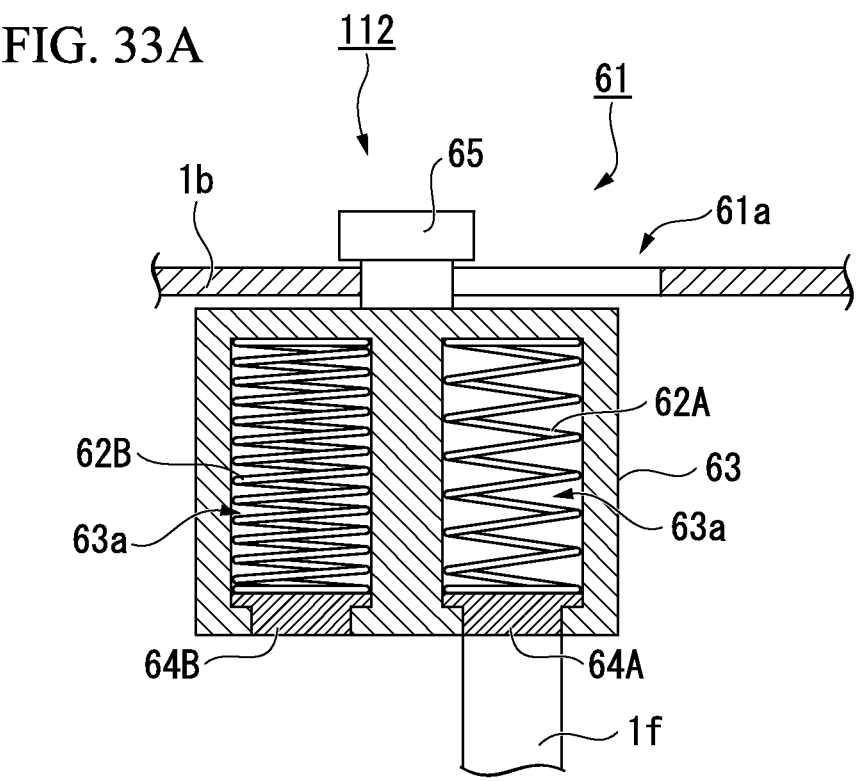
FIG. 33A is a schematic cross-sectional view showing a configuration and an operation of main parts in a manipulation input device according to another fifteenth modified example of the second embodiment of the present invention.
Figure 33B:
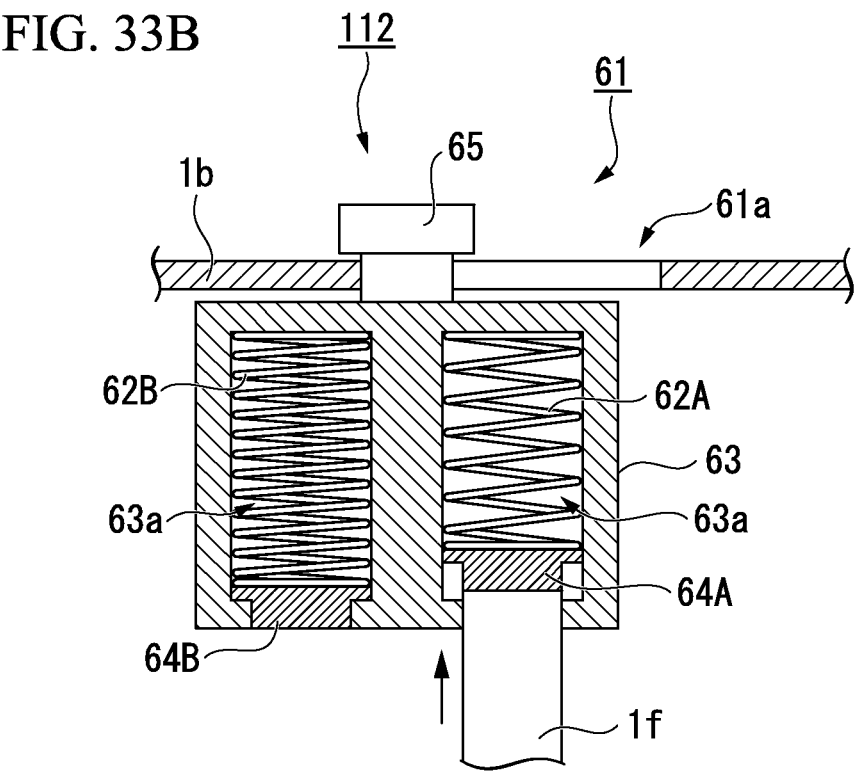
FIG. 33B is a schematic cross-sectional view showing a configuration and an operation of main parts in the manipulation input device according to the fifteenth modified example of the second embodiment of the present invention.
Figure 34:
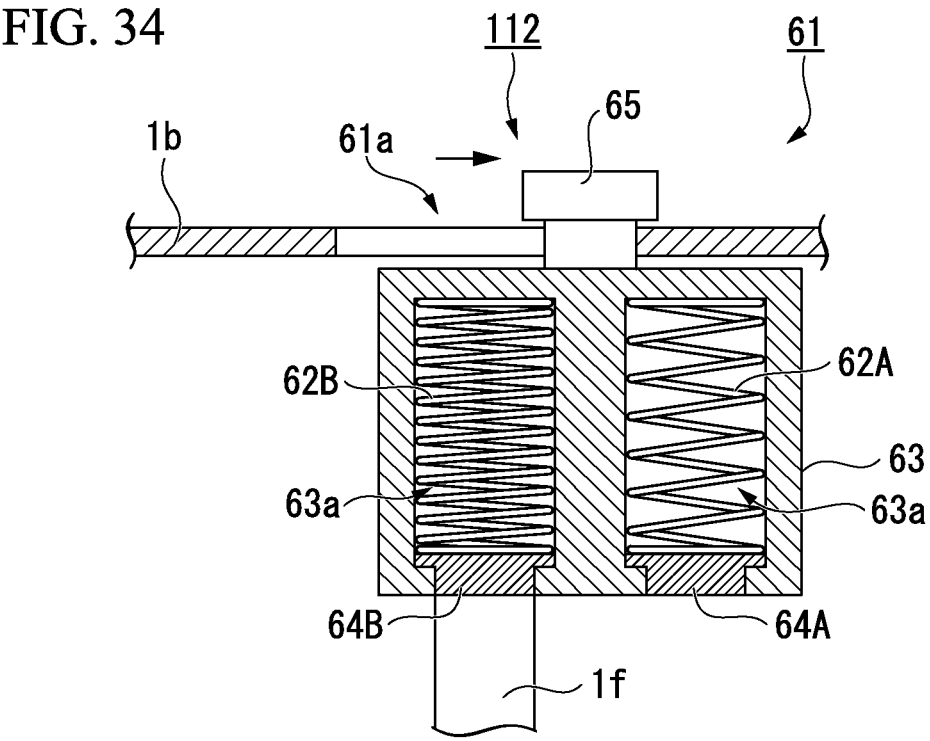
FIG. 34 is a schematic cross-sectional view showing an operation of the manipulation input device according to the fifteenth modified example of the second embodiment of the present invention when a force magnitude is adjusted.

FIGS. 33A and 33B are schematic cross-sectional views showing a configuration of main parts and an operation in a manipulation input device according to the fifteenth modified example of the second embodiment of the present invention. FIG. 34 is a schematic cross-sectional view showing an operation of the manipulation input device according to the fifteenth modified example of the second embodiment of the present invention when a force magnitude is adjusted.

The manipulation input device 112 of the present fifteenth modified example of the second embodiment of the present invention includes a switching holder 63 holding a low elasticity spring 62A and a high elasticity spring (manipulation resistance generator) 62B, both of which have different spring constants, in place of the spring 2 of the master grip 1 in the manipulation input device 100 of the first embodiment, as shown in FIG. 33A by main parts.

Like the manipulation input device 100, the manipulation input device 112 of the present fifteenth modified example of the second embodiment of the present invention may be used as the manipulation input device in the master-slave manipulator 500.

The following description will focus on differences from the first embodiment of the present invention.

The low elasticity spring 62A is a compression coil spring whose spring constant is low compared to the spring 62B.

The high elasticity spring 62B is a compression coil spring whose spring constant is high compared to the spring 62A.

The switching holder 63 includes cylindrical spring holding parts 63a in which the low and high elasticity springs 62A and 62B are arranged in parallel therein.

An end of each spring holding part 63a at a proximal end side is provided with an opening through which a distal end of a displacement shaft 1f moves forward or backward in each spring holding part 63a. Pressing plates 64A and 64B are disposed inside the respective openings. The pressing plates 64A and 64B engage ends of the low and high elasticity springs 62A and 62B at the proximal end side (shown as a lower side), and apply a pressing force from the outside, thereby being movably provided along inner circumferential surfaces of the respective spring holding parts 63a.

The switching holder 63 is movably supported in a direction perpendicular to a forward/backward direction of the displacement shaft 1f by a guide member (not shown) installed in a casing unit 1b.

A switching lug 65 for performing an operation of displacing the switching holder 63 in a direction perpendicular to the forward/backward direction of the displacement shaft 1f is attached to a distal end side (shown upper side) of the switching holder 63.

The switching lug 65 is inserted into a guide hole 61a of a long hole length passing through the casing unit 1b, protrudes to the outside of the casing unit 1b, and is movably installed along a longitudinal direction of the guide hole 61a. For this reason, the operator Op displaces the switching lug 65 protruding to the outside with his/her hand. Thereby, a position of the switching holder 63 can be switched.

With the configuration, as shown in FIGS. 33A and 33B, in a state in which the switching lug 65 is displaced to one end side of the guide hole 61a, the pressing plate 64A faces a distal end face of the displacement shaft 1f in the casing unit 1b.

When the grip part 1a is closed from this state, the displacement shaft 1f moves toward the distal end side. Thereby, as shown in FIG. 33B, the pressing plate 64A is displaced to the distal end side, and the low elasticity spring 62A inside the spring holding part 63a is compressed.

For this reason, in connection with the forward/backward movement of the displacement shaft 1f, the manipulation resistance caused by the spring force corresponding to the spring constant of the low elasticity spring 62A is generated.

To change the manipulation resistance from this state, the operator Op keeps the grip part 1a opened. Thereby, the displacement shaft 1f is displaced to the proximal end side, and as shown in FIG. 33A, the displacement shaft 1f is retracted to the outside of the spring holding part 63a.

Next, the operator Op displaces the switching lug 65 to the other end side of the guide hole 61a.

Thereby, as shown in FIG. 34, the pressing plate 64B faces the distal end face of the displacement shaft 1f in the casing unit 1b.

When the grip part 1a is closed from this state, the displacement shaft 1f is advanced to the distal end side. Thereby, although not specifically shown, the pressing plate 64B is displaced to the distal end side, and the high elasticity spring 62B inside the spring holding part 63a is compressed.

For this reason, in connection with the forward/backward movement of the displacement shaft 1f, the manipulation resistance caused by the spring force corresponding to the spring constant of the high elasticity spring 62B is generated.

In this manner, the present fifteenth modified example of the second embodiment of the present invention is configured as that the low elasticity springs 62A and the high elasticity springs 62B that differ in the magnitude of the spring constant, i.e. the change rate characteristic of the force magnitude of the manipulation resistance, are switchably disposed as the manipulation resistance generators. Thus the operator Op can switch between the low elasticity springs and the high elasticity springs. Thereby, the operator Op can adjust the manipulation resistance as needed.

In each of the embodiments of the present invention and the modified examples described above, except for the twelfth modified example, the manipulation resistance generator is an elastic member.

Thus, a suitable use method when this elastic member is used in each of the embodiments and modified examples will be described.

Figure 35:
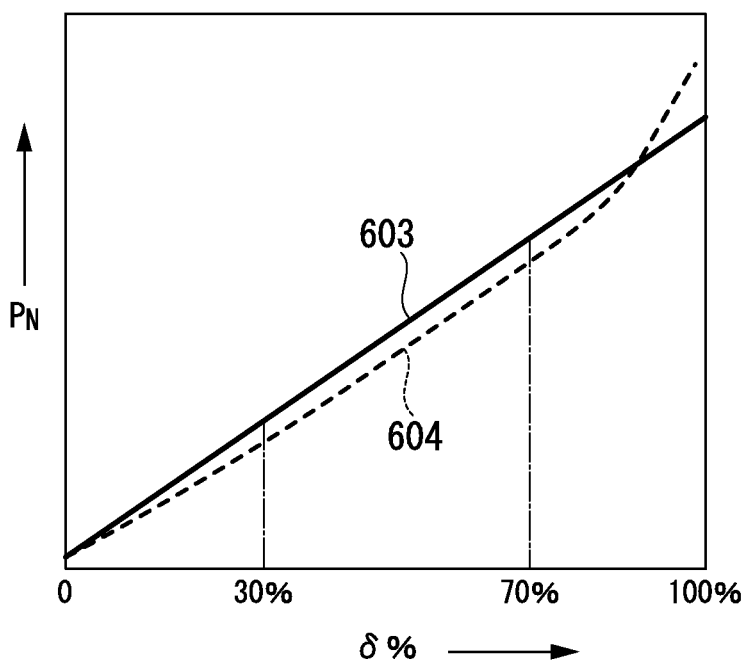
FIG. 35 is a schematic graph showing a use range of an elastic member suitable for each of the embodiments and modified examples of the present invention.

FIG. 35 is a schematic graph showing a use range of an elastic member suitable for each of the embodiments and the modified examples of the present invention. The horizontal axis indicates a deformation amount (elongation amount, deflection amount, compression amount, or the like) of the elastic member which undergoes non-dimensional conversion in terms of a maximum deformation amount and is expressed as a percentage. The vertical axis indicates a spring force $P_N$.

As shown in FIG. 35 by a solid line 603, the elastic member is designed that the spring force $P_N$ is generated in proportion to an elongation rate δ. For example, when the elastic member is a compression coil spring, its spring constant is decided by shape conditions such as an elastic modulus of a wire, a wire diameter, a coil diameter, a winding number, and a winding pitch.

However, the manufactured compression coil spring actually shows a non-linear characteristic as shown, for instance, by a dashed line 604 of FIG. 35.

That is, a range of the elongation rate between about 30% and 70% of the entire deflection goes well with a calculational spring constant, and shows a linear change. On the other hand, when the elongation rate is below 30%, the spring shows a tendency to become weak (slope becomes lower than a design value), and its linearity also becomes poor. Further, when the elongation rate is above 70%, the spring shows a tendency to become strong (slope becomes higher than a design value), and its linearity also becomes poor due to an elastic limit.

As the compression coil spring is compressed, an actually working effective winding number begins contact from opposite ends thereof, and a deformed state is gradually changed in an axial direction, and becomes uneven.

Taking this situation into consideration, the elastic member used in each of the embodiments of the present invention and the modified examples of each of the embodiments of the present invention may be used only in a region of the deformation amount in which an error from this design value is difficult to generate.

In detail, the deformation amount of the elastic member may be used within a range from 30% to 70% with respect to a deformable maximum deformation amount.

Next, specific configuration examples for regulating the use range of the elastic member within a suitable range in this way will be described.

First Configuration Example

First, a master grip 71 of a first configuration example will be described.

FIGS. 36A and 36B are schematic views showing the first configuration example for regulating a use range of an elastic member.

The master grip 71 of the present first configuration example includes a casing unit 1b, manipulation handles 1c, and a spring 2, like the master grip 1 of the first embodiment of the present invention.

In a state in which the manipulation handles 1c shown in FIG. 36A are opened, a length of the spring 2 is set to a length $L_{30}$ when compressed from its natural spring length by 30% of a possible maximum compression amount.

Further, in a state in which the manipulation handles 1c are closed shown in FIG. 36B, the manipulation handles 1c come into contact with sides 71L and 71R of the casing unit 1b. Thereby, a minimum opening/closing angle is accomplished. In this case, the length of the spring 2 is set to a length $L_{70}$ when compressed from its natural spring length by 70% of the possible maximum compression amount.

In the master grip 71, a shape of the master grip 71 is appropriately set, and thereby an opening/closing range of the manipulation handles 1c is mechanically regulated.

The present first configuration example may be similarly applied to the master grip of each of the embodiments and the modified examples of the present invention.

Second Configuration Example

A master grip 81 of a second configuration example will be described.

Figure 37A:
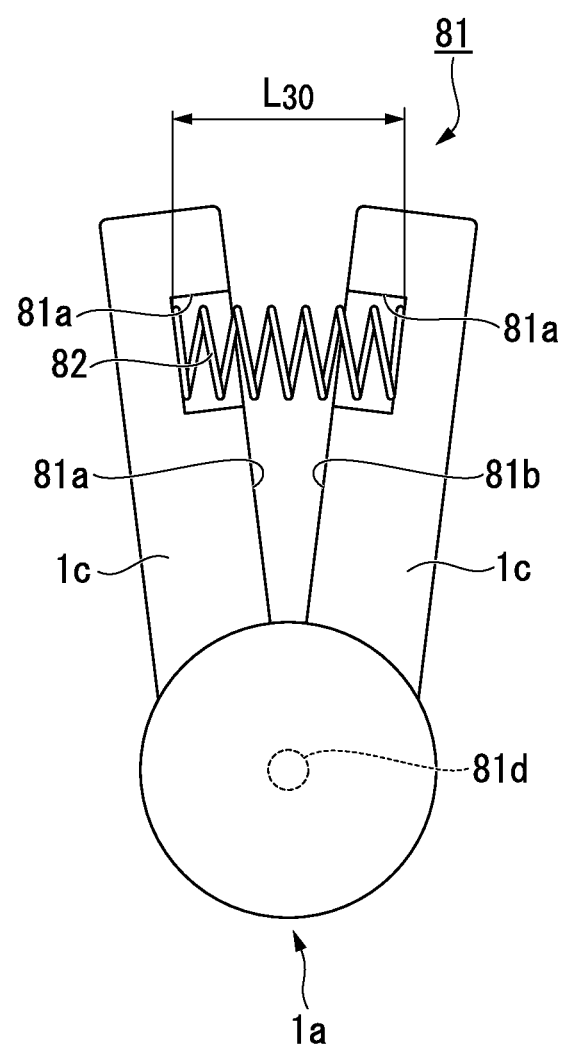
FIG. 37A is a schematic view showing a second configuration example for regulating the use range of the elastic member.
Figure 37B:
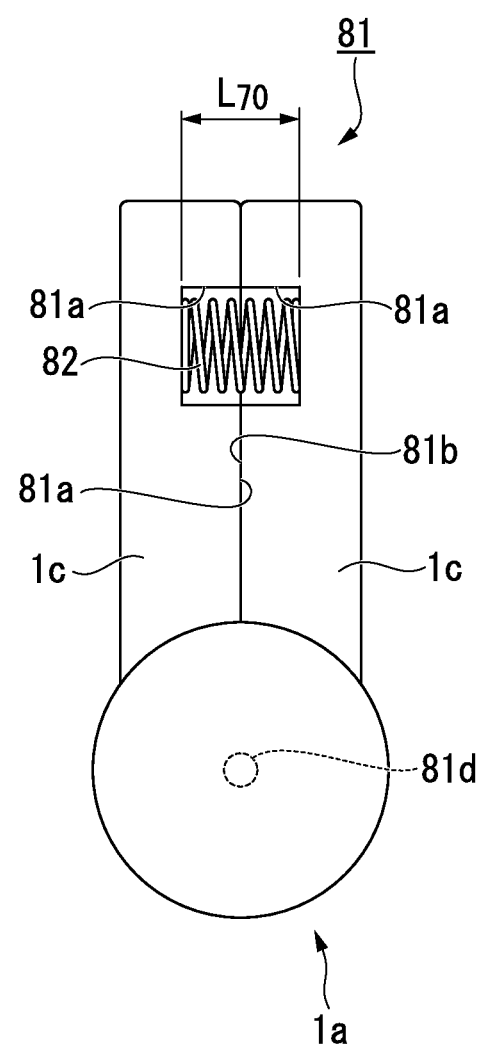
FIG. 37B is a schematic view showing the second configuration example for regulating the use range of the elastic member.

FIGS. 37A and 37B are schematic views showing the second configuration example for regulating the use range of the elastic member.

The master grip 81 of the present second configuration example includes a grip part 1a and manipulation handles 1c, like the master grip 1 of the first embodiment of the present invention.

The manipulation handles 1c are rotatably coupled at proximal end sides thereof by a rotation shaft 81d in the grip part 1a. Further, spring holding recesses 81a engaging ends of a spring 82 generating manipulation resistance are installed at positions facing each other at distal end sides of inner sides 81b facing each other.

A rotation regulating member (not shown) is installed in the grip part 1a. Thereby, a maximum opening/closing angle of the inner sides 81b is regulated to an angle shown in FIG. 37A. In this case, a distance between recess bottoms of the spring holding recesses 81a is set to a length $L_{30}$ when compressed from a natural spring length of the spring 82 by 30% of a possible maximum compression amount. When the manipulation handles 1c are in a maximum opened state, the spring length of the spring 82 held in the spring holding recesses 81a is regulated to $L_{30}$.

Further, in the present second configuration example, as shown in FIG. 37B, the manipulation handles 1c are closed until the inner sides 81b come into contact with each other. Thereby, a minimum opening/closing angle of the manipulation handles 1c is set. In this case, the spring 82 held in the spring holding recesses 81a is compressed to a length equal to the sum of recess depths of the spring holding recesses 81a.

In the present second configuration example, the recess depth of each spring holding recess 81a is set to the half of a length $L_{70}$ when compressed from the natural spring length of the spring 82 by 70% of the possible maximum compression amount. When the manipulation handles 1c are in a closed state in which the manipulation handles 1c have the minimum opening/closing angle, the spring length of the spring 82 held in the spring holding recesses 81a is regulated to $L_{70}$.

Third Configuration Example

A master grip 91 of a third configuration example will be described.

Figure 38A:
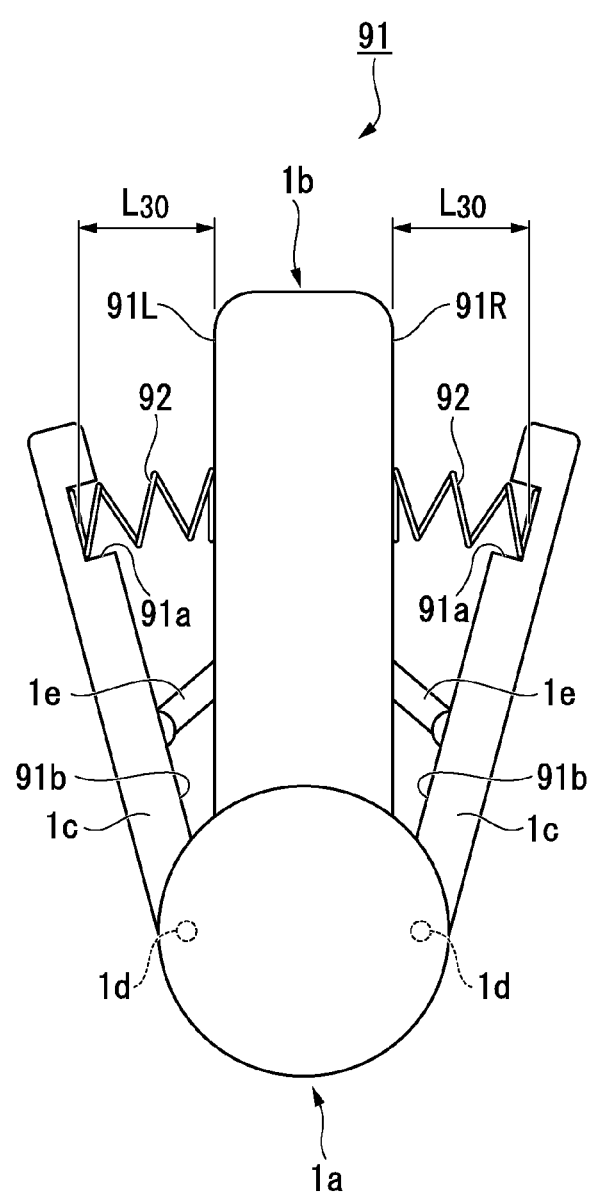
FIG. 38A is a schematic view showing a third configuration example for regulating the use range of the elastic member.
Figure 38B:
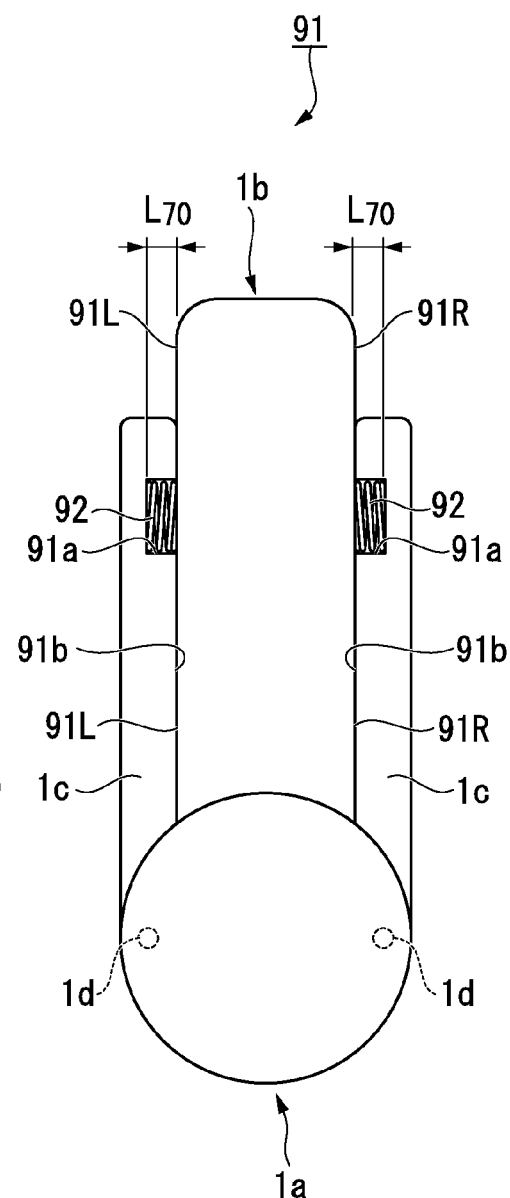
FIG. 38B is a schematic view showing the third configuration example for regulating the use range of the elastic member.

FIGS. 38A and 38B are schematic views showing the third configuration example for regulating the use range of the elastic member.

The master grip 91 of the present third configuration example includes a grip part 1a, a casing unit 1b, and manipulation handles 1c like the master grip 1 of the first embodiment of the present invention, and is provided with two springs 92 generating manipulation resistance. One of the springs 92 is installed between a side 91L of the casing unit 1b and the manipulation handle 1c, and the other spring 92 is installed between a side 91R of the casing unit 1b and the manipulation handle 1c.

One end of the spring 92 and the side 91L (91R) are fixed by a fixing means (not shown).

Further, the other end of the spring 92 and the manipulation handle 1c are fixed to a recess bottom of each of spring holding recesses 91a formed in inner sides 91b of the manipulation handles 1c.

In the present third configuration example, in a closed state of the manipulation handles 1c which is shown in FIG. 38B, the manipulation handles 1c come into contact with the sides 91L and 91R of the casing unit 1b. Thereby, a minimum opening/closing angle is accomplished. In this case, the springs 92 are compressed to recess depths of the respective spring holding recesses 91a. The recess depth of each spring holding recess 91a is set to a length $L_{70}$ when compressed from the natural spring length of the spring 92 by 70% of the possible maximum compression amount.

Then, in an opened state of the manipulation handles 1c which is shown in FIG. 38A, a maximum opening/closing angle is set so that a distance from the recess bottom of each spring holding recess 91a to the side 91L (91R) to which the spring 92 is fixed is set to a length $L_{30}$ when compressed from the natural spring length of the spring 92 by 30% of the possible maximum compression amount.

Fourth Configuration Example

A master grip 95 of a fourth configuration example will be described.

Figure 39A:
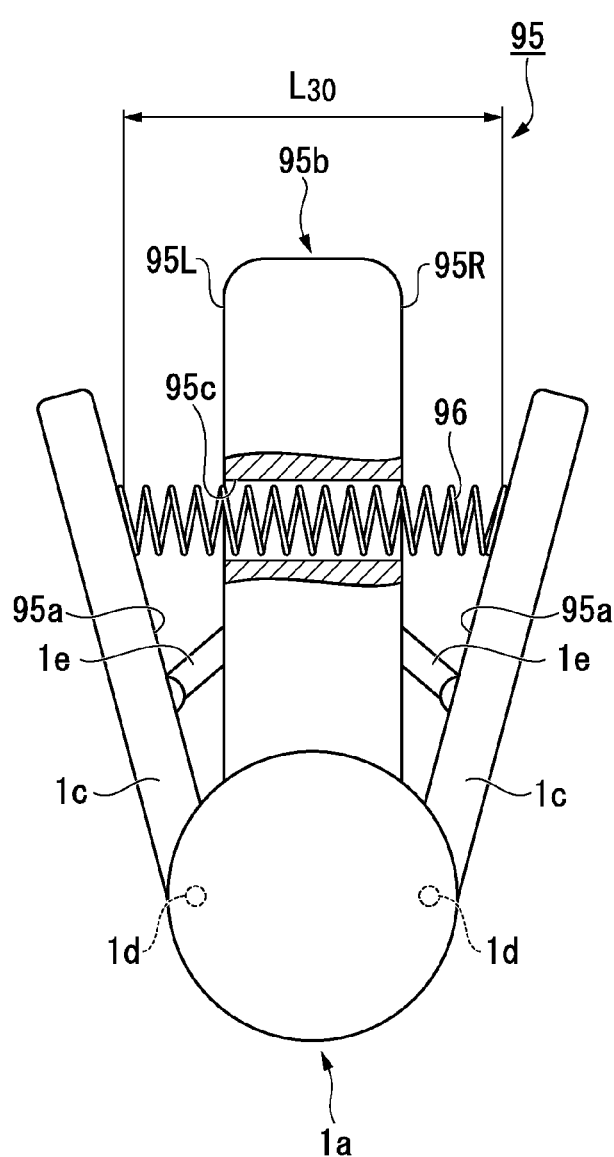
FIG. 39A is a schematic view showing a fourth configuration example for regulating the use range of the elastic member.
Figure 39B:
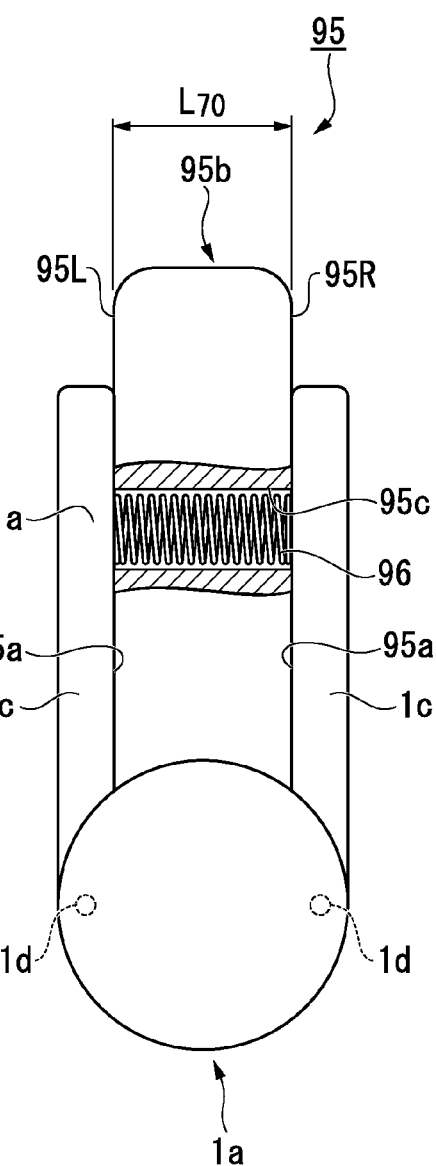
FIG. 39B is a schematic view showing the fourth configuration example for regulating the use range of the elastic member.

FIGS. 39A and 39B are schematic views showing the fourth configuration example for regulating the use range of the elastic member.

The master grip 95 of the present fourth configuration example includes a grip part 1a and manipulation handles 1c like the master grip 1 of the first embodiment, and is provided with a spring 96 between inner sides 95a of the manipulation handles 1c to generate manipulation resistance.

The master grip 95 includes a casing unit 95b between the manipulation handles 1c in place of the casing unit 1b of the master grip 1. As shown in FIG. 39B, the inner sides 95a of the manipulation handles 1c come into contact with sides 95L and 95R of the casing unit 95b. Thereby, a minimum opening/closing angle is regulated.

Further, an insertion hole part 95c into which the spring 96 can be inserted is formed between the sides 95L and 95R of the casing unit 95b.

In the present fourth configuration example, in this closed state, the spring 96 is compressed to the same length as the insertion hole part 95c. Thus, the length of the insertion hole part 95c is set to a dimension that becomes a length $L_{70}$ when compressed from the natural spring length of the spring 96 by 70% of the possible maximum compression amount.

Then, in an opened state of the manipulation handles 1c which is shown in FIG. 39A, a maximum opening/closing angle is set so that a distance between fixed positions of the spring 96 on the inner sides 95a of the manipulation handles 1c is set to a length $L_{30}$ when compressed from the natural spring length of the spring 96 by 30% of the possible maximum compression amount.

In the description of each of the embodiments and the modified examples of the present invention, when the manipulation resistance generator is formed of the elastic member, an example is given as that the elastic member is formed of the compression coil spring. However, the elastic member is not limited to the example as long as it can generate the manipulation resistance. For example, the elastic member such as a tension coil spring may be used.

Further, the elastic member is not limited to the spring member. For example, as the elastic member, a sponge or rubber may be used. Further, as in the second embodiment of the present invention, the fourteenth modified example of the second embodiment of the present invention, and the fifteenth modified example of the second embodiment of the present invention, a plurality of spring members (spring parts) are combined and used as the elastic member, also a sponge or rubber may be used for some or all of the spring members (spring parts).

A spring constant of the sponge or rubber refers to a ratio between a load applied to the elastic member and displacement, like the spring member, Further, the spring member, sponge and rubber may have non-linearity if a relation between an elongation amount and a force magnitude is known. Further, the spring member, sponge and rubber may be used on a non-linear region beyond an elastic limit.

In this manner, in each of the embodiments and the modified examples of each of the embodiments of the present invention, since the elastic member is used in a broad sense, as long as a restoring force is generated in response to deformation, the "spring constant" need not have a given value for each elastic member, and when a load applied to the elastic member is defined as f, and an elongation amount of the elastic member as x, a member whose spring constant is represented by a function k(x) is also included in the elastic member. That, $f=k(x)*x$ should be satisfied.

The spring 52 of the fourteenth modified example is an example in which, since the low elasticity spring portion 52A collapses depending on the compression amount and thereby a part of the spring 52 exceeds an elastic limit, the spring constant is changed by a displacement amount.

Further, in the description of the second embodiment of the present invention, two spring members are combined to be used, and thereby the spring constant is changed. However, a releasable spring member may be configured to be installed between the spring coupling part 1g and the spring holding part 1h.

For example, a spring member having a natural length that is shorter than a maximum interval formed between the spring coupling part 1g and the spring holding part 1h may be configured to be fixed to the spring coupling part 1g.

In this case, until the spring member comes into contact with the spring holding part 1h, the displacement shaft 1f is displaced with no manipulation resistance without receiving a reaction force from the spring member. The spring member comes into contact with the spring holding part 1h, and then is compressed in response to the displacement amount of the displacement shaft 1f, thereby a restoring force occurs, and the manipulation resistance is generated.

The modified example corresponds to a limit when the spring constant of the first spring 42A of the second embodiment is set to zero (0) or a limit when the spring constant of the low elasticity spring portion 52A in the fourteenth modified example is set to zero (0).

Further, in the description of the fifth modified example of the first embodiment of the present invention, the case in which the master grip 223 is demounted or mounted, and simultaneously the entire force magnitude adjusting unit 213A is demounted or mounted is given as an example. However, if the manipulation resistance generator in which the manipulation resistance is changed is demounted or mounted together with the master grip 223, the force magnitude adjusting unit except the manipulation resistance generator may be configured to be left at and demounted or mounted from or on the arm distal end 202a.

For example, when the force magnitude adjusting unit 213A is configured to have the actuator 13b or the actuator 33b, the actuator 13b or 33b that is a driving means may be left at and demounted or mounted from or on the arm distal end 202a.

Further, in the descriptions of the seventh to the ninth modified examples of the first embodiment of the present invention, the case in which the degradation of the elastic member is determined by the number of uses is given as an example. However, in place of the number of uses, a time of use may be measured. Thereby, the degradation of the elastic member may be configured to be determined.

Further, in the descriptions of the second embodiment of the present invention and the thirteenth modified example of the first embodiment of the present invention, the case in which the change rate characteristic of the spring force has a plurality of linear regions, and the manipulation resistances are switched on the respective linear regions is given as an example. However, the driving amount of the force magnitude adjusting member 3a is appropriately adjusted. Thereby, the length range of the elastic member may be set so that the spring constant includes the switching range.

In this way, the manipulation resistance can be changed in a non-linear form together with a change in the opening/closing angle. For example, the manipulation resistance is reduced up to a given opening/closing angle, and when the given opening/closing angle is exceeded, the manipulation resistance is abruptly increased. This sense of manipulation can be realized.

Further, in the fourteenth modified example of the second embodiment of the present invention, the case in which two elastic members having different spring constants are switchably installed is described as an example. However, three or more springs may be switchably installed. In this case, the switching holder 63 may be configured to be switched by a revolver mechanism that is based on rotational displacement rather than slide displacement.

Further, in the description of each of the embodiments and the modified examples of each of the embodiments of the present invention, the case in which the manipulation handle is supported to be pivotal around the manipulation unit main body, and thus can be opened or closed is given as an example. However, it will do if the manipulation handle is movably supported with respect to the manipulation unit main body.

Another example of this manipulation handle that can be used in the present invention will be described with reference to FIGS. 40A and 40B.

Figure 40A:
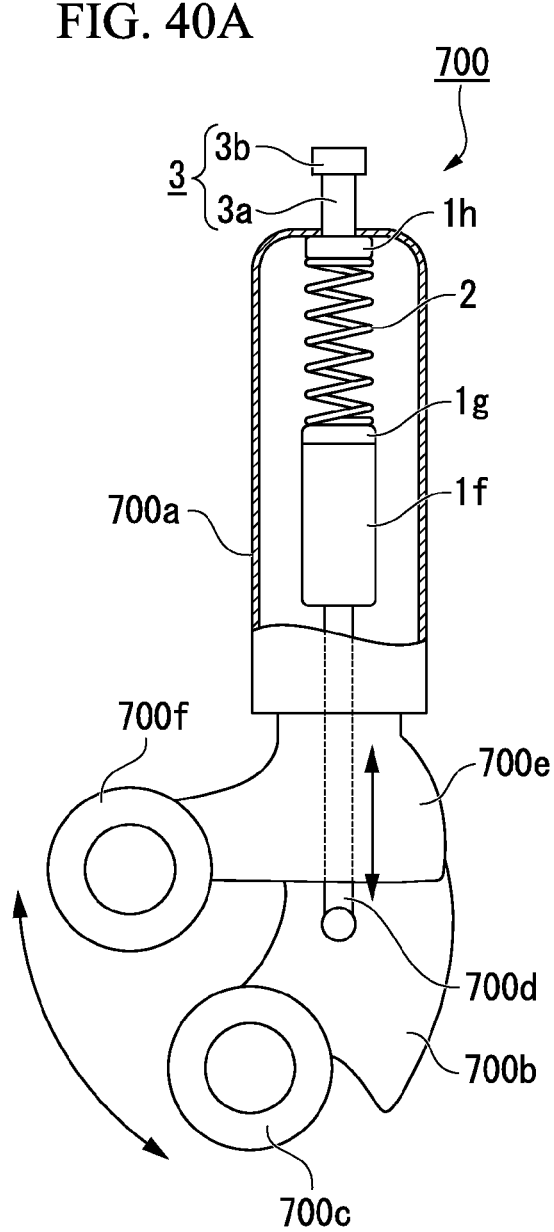
FIG. 40A is a schematic partial cross-sectional view showing a configuration of another example of a manipulation handle that is capable of being used in the manipulation input device of each of the embodiments and modified examples of the present invention.
Figure 40B:
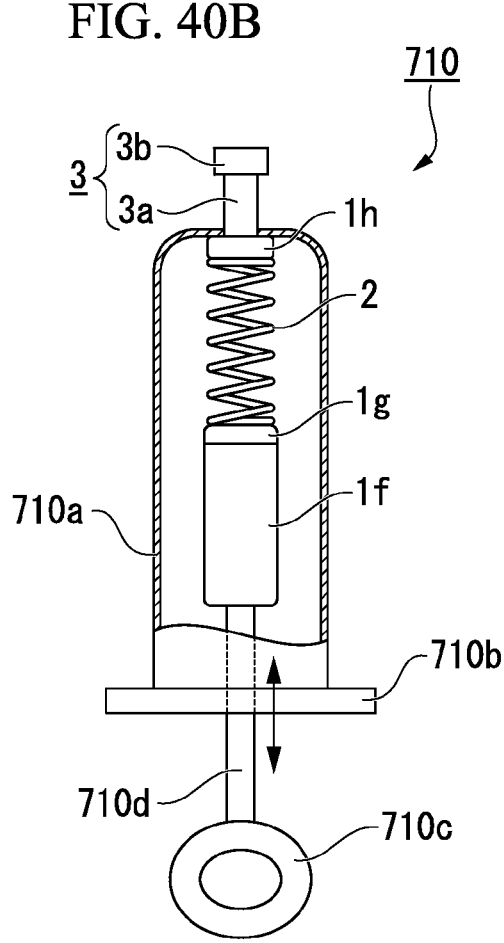
FIG. 40B is a schematic partial cross-sectional view showing a configuration of another example of a manipulation handle that is capable of being used in the manipulation input device of each of the embodiments and modified examples of the present invention.
Figure 40C:
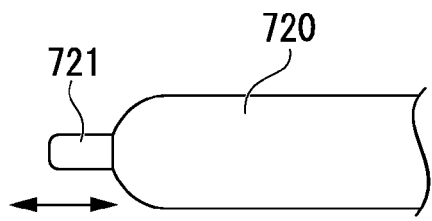
FIG. 40C is a schematic partial enlarged view of a distal end of a treatment tool that is capable of being used in the manipulation input device of each of the embodiments and modified examples of the present invention.

FIGS. 40A and 40B are schematic partial cross-sectional views showing a configuration of another example of a manipulation handle that can be used in the manipulation input device of each of the embodiments and modified examples of the present invention. FIG. 40C is a schematic partial enlarged view of a distal end of a treatment tool.

A master grip (manipulation unit) 700 shown in FIG. 40A is a scissors type grip that removes the links 1e of the master grip 1 of the first embodiment of the present invention, and includes a cylinder part (manipulation unit main body) 700a, a stationary handle (manipulation handle) 700e, and a movable handle (manipulation handle) 700b in place of the grip part 1a, the casing unit 1b, and the manipulation handles 1c.

The master grip 700 may also be used to manipulate the treatment tools 302, as in the first embodiment.

The following description will focus on differences from the first embodiment of the present invention.

As in the first embodiment of the present invention, the cylinder part 700a includes a force magnitude adjusting unit 3 at a distal end thereof and is provided therein with a spring holding part 1h, a spring 2, a spring coupling part 1g, and a displacement shaft 1f. The displacement shaft 1f is disposed to be able to move forward or backward along a central axis of the cylinder part 700a.

The stationary handle 700e is a member that is fixed to an end of the cylinder part 700a at a side opposite the force magnitude adjusting unit 3 and supports the cylinder part 700a by means of a finger of an operator Op.

An end of the stationary handle 700e is provided with a ring part 700f into which one finger of the operator Op is inserted.

The movable handle 700b is a member that displaces the displacement shaft 1f along the central axis of the cylinder part 700a, and one end thereof is pivotally supported on the end of the cylinder part 700a.

The movable handle 700b includes a linear conversion mechanism that converts rotational operation of the movable handle 700b into linear operation in a direction directed to the central axis of the cylinder part 700a using, for instance, a cam and a link, and moves a rod 700d forward or backward along the central axis of the cylinder part 700a.

An end of the rod 700d is coupled with the displacement shaft 1f.

Further, the other end of the movable handle 700b is provided with a ring part 700c into which another finger of the operator Op is inserted.

According to the master grip 700 configured in this way, the operator Op inserts his/her fingers into the respective ring parts 700f and 700c, and rotates the movable handle 700b in relation to the stationary handle 700e as shown by an arrow. In this case, an opening/closing angle of the manipulation handle is defined as a rotational angle of the movable handle 700b relative to the stationary handle 700e.

Depending on the opening/closing manipulation, the rod 700b moves forward or backward along the central axis of the cylinder part 700a. Thereby, the displacement shaft 1f can be displaced forward or backward along the central axis of the cylinder part 700a.

The forward/backward displacement of the displacement shaft 1f is exactly the same as that of the displacement shaft 1f in the first embodiment of the present invention. As such, similar to the first embodiment, the opening/closing manipulation of the treatment tool 302 can be performed.

Further, the master grip 700 is an example in which the manipulation handle is pivotally supported on the manipulation unit main body and is allowed to perform the opening/ closing manipulation, and one side of the manipulation handle is fixed to the manipulation unit main body.

The master grip (manipulation unit) 710 shown in FIG. 40B is an injector type grip that removes the links 1e of the master grip 1 of the first embodiment, and includes a cylinder part (manipulation unit main body) 710a, a finger engaging part 710b, and a manipulation ring (manipulation handle) 710c in place of the grip part 1a, the casing unit 1b, and the manipulation handles 1c.

The master grip 710 is particularly suitable to manipulate a treatment tool, whose movable part performs forward/backward movement, such as a knife type monopolar treatment tool 720 shown in FIG. 40C.

The knife type monopolar treatment tool 720 is a treatment tool that includes an electrode 721 installed on a distal end thereof to be able to move forward or backward and is used to perform coagulotomy on tissues by conducting electric current to the electrode 721.

The following description will focus on differences from the first embodiment.

As in the first embodiment, the cylinder part 710a includes a force magnitude adjusting unit 3 at a distal end thereof and is provided therein with a spring holding part 1h, a spring 2, a spring coupling part 1g, and a displacement shaft 1f. The displacement shaft 1f is disposed to be able to move forward or backward along a central axis of the cylinder part 710a.

The finger engaging part 710b is a protrusion part that is formed at an end of the cylinder part 710a to engage the finger of the operator Op, for instance, when the cylinder part 710a is grasped by the finger of the operator Op.

The manipulation ring 710c is an annular manipulation handle into which the finger of the operator Op is inserted to transfer a manipulation input by the operator Op to the displacement shaft 1f, and is coupled with the displacement shaft 1f in the cylinder part 710a via a driving shaft 710d movably supported along the central axis of the cylinder part 710a.

According to the master grip 710 configured in this way, the finger of the operator Op inserted into the manipulation ring 700c moves forward or backward in relation to the finger engaging part 710b. Thereby, the displacement shaft 1f can be displaced forward or backward along the central axis of the cylinder part 710a.

For this reason, the master grip 710 can be suitably used, for instance, to displace the electrode 721 of the knife type monopolar treatment tool 720 forward or backward.

However, the master grip 710 displaces the displacement shaft 1f forward or backward, like the first embodiment. As such, similar to the first embodiment, the manipulation of the treatment tool 302 can also be performed.

Further, the master grip 710 is an example in which the manipulation handle performs the forward/backward movement rather than the opening/closing operation.

Further, all the components described in each of the embodiments and modified examples can be carried out by replacing or removing an appropriate combination thereof within the scope of the technical idea of the present invention.

For example, when the manipulation resistance is automatically adjusted, a manual adjustment mode of manually adjusting the manipulation resistance may be set.

Further, when the adjustment amount of the manipulation resistance is automatically set by, for instance, acquiring the ID information, a plurality of adjustment amount setting modes in which the adjustment amount can be input according to the preference of the operator Op may be set.

Further, for example, the fourth to seventh modified examples of the first embodiment of the present invention may be appropriately combined. In this case, the combined pieces of information (e.g., treatment tool identification information and grip identification information) are sent to the force magnitude calculation unit, and the force magnitude calculation unit calculates an optimal force magnitude based on each piece of information, and sends a driving signal corresponding to a result of the calculation to the force magnitude adjusting unit. Thus, the force magnitude is adjusted.

Further, for example, in the ninth modified example of the first embodiment of the present invention, similar to the eleventh modified example, during the operation of the master-slave manipulator 500, the time-dependent change detection unit detects whether or not the preset reaction force of the spring 2 is subjected to a time-dependent change more than an allowable limit at all times, as needed, or at fixed periods. When the time-dependent change is detected, a warning that the time-dependent change exceeds the allowable limit may be configured to be given by a sign or a warning tone caused by the display unit 201. In this case, the display unit 201 configures a time-dependent change warining unit.

Further, in this case, an adjustment mode is activated in response to the warning. Thereby, desired adjustment can be performed by a manual adjustment mechanism.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A manipulation input device comprising:
   a manipulation unit comprising:
      a manipulation unit main body; and
      manipulation handles movably supported on the manipulation unit main body;
   a manipulation resistance generator configured to generate manipulation resistance in response to a displacement amount of the manipulation handles when the manipulation handles are manipulated; and
   a force magnitude adjusting unit configured to adjust a force magnitude of the manipulation resistance relative to the displacement amount,
   wherein the force magnitude adjusting unit is configured to fix a change rate characteristic of the force magnitude of the manipulation resistance relative to the displacement amount, and to change a reference force magnitude value of the force magnitude of the manipulation resistance relative to a reference value of the displacement amount.

2. The manipulation input device according to claim 1, wherein the manipulation handles are rotatably supported on the manipulation unit main body and are installed to permit opening/closing manipulation.

3. The manipulation input device according to claim 1, wherein:
   the manipulation resistance generator includes an elastic member configured to be deformed by displacement manipulation of the manipulation handles and configured to generate the manipulation resistance; and the force magnitude adjusting unit is configured to deform the elastic member, and to adjust a deformation amount of the elastic member to change the reference force magnitude value.

4. The manipulation input device according to claim 3, wherein the force magnitude adjusting unit includes an actuator configured to change the reference force magnitude value.

5. The manipulation input device according to claim 4, further comprising a manipulation input control unit configured to control an operation of the actuator.

6. The manipulation input device according to claim 5, wherein the manipulation input control unit is configured to acquire identification information about a manipulated device from the manipulated device and to control the operation of the actuator based on the identification information.

7. The manipulation input device according to claim 5, wherein the manipulation unit includes an identification information part that is detachably installed on a manipulation input device main body and transfers identification information about the manipulation unit to the manipulation input control unit when mounted.

8. The manipulation input device according to claim 5, wherein the manipulation input control unit includes a procedure mode input unit configured to receive an input by an operator of a procedure mode to be performed by the manipulated device, and is configured to control the operation of the actuator based on the procedure mode input by the procedure mode input unit.

9. The manipulation input device according to claim 5, wherein the manipulation input control unit includes a time-dependent change detection unit configured to detect a time-dependent change of the manipulation resistance, and is configured to control the operation of the actuator to correct the time-dependent change of the manipulation resistance when the time-dependent change of the manipulation resistance is detected by the time-dependent change detection unit.

10. The manipulation input device according to claim 9, wherein the time-dependent change detection unit is configured to determine the time-dependent change of the manipulation resistance based on a number of times of manipulation of the manipulation resistance generator.

11. The manipulation input device according to claim 9, wherein the time-dependent change detection unit is configured to determine the time-dependent change of the manipulation resistance based on a manipulation time of the manipulation resistance generator.

12. The manipulation input device according to claim 9, further comprising a force detection unit configured to detect a reaction force of the manipulation resistance generator, wherein the time-dependent change detection unit is configured to determine the time-dependent change of the manipulation resistance based on a force magnitude of the reaction force of the manipulation resistance generator.

13. The manipulation input device according to claim 1, wherein the force magnitude adjusting unit includes a manual adjustment mechanism configured to manually adjust the reference force magnitude value.

14. The manipulation input device according to claim 13, further comprising:
an adjustment target setting means configured to set an adjustment target value of the reference force magnitude value; and
an adjustment detection unit configured to detect a difference of the reference force magnitude value from the adjustment target value when the manual adjustment mechanism operates, and inform of whether or not the reference force magnitude value is identical to the adjustment target value.

15. The manipulation input device according to claim 13, further comprising an adjustment detection unit configured to detect a difference of the reference force magnitude value from a preset adjustment target value when the manual adjustment mechanism operates, and inform of whether or not the reference force magnitude value is identical to the adjustment target value.

16. The manipulation input device according to claim 13, further comprising:
a time-dependent change detection unit configured to detect a time-dependent change of the manipulation resistance; and
a time-dependent change warning unit configured to give a warning when the time-dependent change of the manipulation resistance is detected by the time-dependent change detection unit.

17. The manipulation input device according to claim 16, wherein the time-dependent change detection unit is configured to determine the time-dependent change of the manipulation resistance based on a number of times of manipulation of the manipulation resistance generator.

18. The manipulation input device according to claim 16, wherein the time-dependent change detection unit is configured to determine the time-dependent change of the manipulation resistance based on a manipulation time of the manipulation resistance generator.

19. The manipulation input device according to claim 16, further comprising a force detection unit configured to detect a reaction force of the manipulation resistance generator, wherein the time-dependent change detection unit is configured to determine the time-dependent change of the manipulation resistance based on a force magnitude of the reaction force of the manipulation resistance generator.

20. A manipulation input device comprising:
a manipulation unit comprising:
a manipulation unit main body; and
manipulation handles movably supported on the manipulation unit main body;
a manipulation resistance generator configured to generate manipulation resistance in response to a displacement amount of the manipulation handles when the manipulation handles are manipulated; and
a force magnitude adjusting unit configured to adjust a force magnitude of the manipulation resistance relative to the displacement amount,
wherein the force magnitude adjusting unit is configured to change a change rate characteristic of the force magnitude of the manipulation resistance relative to the displacement amount, and thereby change a reference force magnitude value of the force magnitude of the manipulation resistance relative to a reference value of the displacement amount.

21. The manipulation input device according to claim 20, wherein the manipulation resistance generator includes an elastic member, a spring constant of which is changed depending on the displacement amount.

22. The manipulation input device according to claim 20, wherein the manipulation resistance generator includes a resistance generating actuator configured to generate a reaction force by displacement manipulation of the manipulation handles to generate the manipulation resistance and to make the reaction force adjustable.

23. A manipulator system comprising the manipulation input device according to claim 1.

* * * * *